(12) United States Patent
Kubota et al.

(10) Patent No.: US 7,375,222 B2
(45) Date of Patent: May 20, 2008

(54) 2,4,6-TRIAMINO-1,3,5-TRIAZINE DERIVATIVE

(75) Inventors: Hideki Kubota, Tsukuba (JP); Takeshi Suzuki, Tsukuba (JP); Masanori Miura, Tsukuba (JP); Eiichi Nakai, Tsukuba (JP); Kiyoshi Yahiro, Tsukuba (JP); Akira Miyake, Tsukuba (JP); Shinobu Mochizuki, Tsukuba (JP); Kazuhiro Nakatou, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 471 days.

(21) Appl. No.: 10/503,494

(22) PCT Filed: Feb. 3, 2003

(86) PCT No.: PCT/JP03/01065

§ 371 (c)(1),
(2), (4) Date: Aug. 5, 2004

(87) PCT Pub. No.: WO03/066099

PCT Pub. Date: Aug. 14, 2003

(65) Prior Publication Data

US 2006/0194803 A1 Aug. 31, 2006

(30) Foreign Application Priority Data

Feb. 5, 2002 (JP) .............................. 2002-028844

(51) Int. Cl.
| | |
|---|---|
| *C07D 251/70* | (2006.01) |
| *C07D 401/12* | (2006.01) |
| *C07D 403/12* | (2006.01) |
| *C07D 405/12* | (2006.01) |
| *C07D 409/12* | (2006.01) |
| *A61K 31/53* | (2006.01) |
| *A61P 25/28* | (2006.01) |

(52) U.S. Cl. .................. 544/198; 514/245; 544/197
(58) Field of Classification Search ................ 544/197, 544/198; 514/245
See application file for complete search history.

(56) References Cited

U.S. PATENT DOCUMENTS

| | | | |
|---|---|---|---|
| 4,742,160 A | 5/1988 | Dore et al. | |
| 4,794,135 A | 12/1988 | Wheeler et al. | |
| 5,498,701 A | 3/1996 | Pedrazzi | |
| 5,744,127 A | 4/1998 | Giuseppe et al. | |
| 5,922,122 A | 7/1999 | Takeda et al. | |
| 6,117,996 A | 9/2000 | Lowe et al. | |
| 6,123,763 A | 9/2000 | Kamikubo et al. | |
| 6,150,360 A | 11/2000 | Daeyaert et al. | |
| 6,193,960 B1 | 2/2001 | Metzger et al. | |
| 6,262,053 B1 * | 7/2001 | Uckun et al. | 514/245 |
| 6,326,168 B1 * | 12/2001 | Miyake et al. | 435/69.1 |
| 6,335,339 B1 | 1/2002 | Arenas et al. | |

FOREIGN PATENT DOCUMENTS

| | | |
|---|---|---|
| EP | 1 050 542 A1 | 8/2000 |
| GB | 951667 | 3/1964 |
| JP | 48008916 A | 2/1973 |
| JP | 61246261 A | 11/1986 |
| JP | 11-43448 A | 2/1999 |
| JP | 11158073 A | 6/1999 |
| JP | 11199796 A | 7/1999 |
| WO | WO 99/01442 A1 | 1/1999 |
| WO | 9936410 A1 | 7/1999 |
| WO | WO 99/50256 A1 | 10/1999 |
| WO | WO 00/69823 A1 | 11/2000 |
| WO | WO 00/78738 A1 | 12/2000 |
| WO | WO 01/02406 A1 | 1/2001 |
| WO | WO 01/22938 A1 | 4/2001 |
| WO | WO 01/66743 A2 | 9/2001 |
| WO | WO 03/024448 A3 | 3/2003 |
| WO | WO 03/024926 A2 | 3/2003 |

OTHER PUBLICATIONS

Donald W. Ludovici et al., "Evolution of Anti-HIV Drug Candidates Part 2: Diaryltriazine (DATA) Analogues" (2001), Bioorganic Y Medicinal Chemistry Letters, pp. 2230-2234.

A.C. Chawda et al., "Preparation and Antimicrobial Activity of 2, 4-Diarylamino-6-(α-Phenyl Sulphonyl) Benzylamino-S-Triazines" (1992), Acta Ciencia Indicia, vol. XVIII C, No.4, pp. 405-406.

P.M. Parasharya et al., "Studies on s-Triazoines: Part-XIV Preparation and Antimicrobial Activity of 2,4-Diarylamino 6-Dimethylaminoethyl-Amino s-Triazines" (1985), Acta Ciencia Indicia, vol. XI c, No.1, pp. 66-69.

(Continued)

*Primary Examiner*—Venkataraman Balasubramanian
(74) *Attorney, Agent, or Firm*—Sughrue Mion, PLLC

(57) ABSTRACT

This invention relates to an anti-dementia agent which uses a BEC 1 potassium channel inhibitor as the active ingredient.

It was proved that the BEC 1 potassium channel inhibitor has an action to improve learning disorder and is useful as a preventive or therapeutic agent for diseases, preferably dementia, in which the BEC 1 potassium channel is considered to be concerned.

Illustratively, it was confirmed by an in vivo test that the BEC 1 potassium channel inhibitor has an action to improve learning disorder.

Also, it was found that a compound having 2,4,6-triamino-1,3,5-triazine has a BEC 1 potassium channel inhibitory action.

3 Claims, No Drawings

OTHER PUBLICATIONS

W. Brandes et al., "Studies on 1,3,4-Oxadiazoles, Part-IV. Preparation of 2-Ary 1-5-(2,4-bis-P-chlorophenyl-amino-s-triazin-6-ylaminomethyl)-1,3,4-oxadiazoles" (1987), J. Indian Chem. Soc., vol. LXIV, pp. 770-771.

Lina Mehta et al., "Studies on S-Triazines Part-I: Preparation of 2,4-Diarylamino-6-N,N-Diethylaminoethylamino/N,N-Diethylamino Ethoxy-S-Triazines" (1987), J. Inst. Chemists (India), vol. 59, pp. 183-185.

K.R. Desai et al., "Synthesis of s-Triazline Derivatives" (1988), J. Indian Chem. Soc., vol. LXV, pp. 300-301.

International Search Report dated May 6, 2003.

Akira Miyake et al., "New Ether-a-go-go $K^+$Channel Family Members Localized in Human Telencephalon", (1999) The Journal of Biological Chemistry, vol. 274, No. 35, pp. 25018-25025.

"Potassium Channels and Chloride Channels" (1992) Ionic Channels of Excitable Membranes, Second Edition.

"Potassium Channels" (2002), IUPHAR, pp. 59-63.

Shun-ichi Yamaguchi et al., "Effects of anticonvulsant drugs on 4-aminopyridine-induced seizures in mice" (1992), Elsevier Science Publishers B.V., pp. 9-16.

M. Gwilt et al., "UK-68,798: A Novel, Potent and Highly Selective Class III Antiarrhythmic Agent Which Blocks Potassium Channels in Cardiac Cells" (1990), The Journal of Pharmacology and Experimental Therapeutics, vol. 256, No. 1, pp. 318-321.

Irwin B. Levitan et al., "Cell and Molecular Biology" (1991), Oxford University Press, pp. 395-423.

Sushmita, Ganguly S. et al., "s-Triazines-Part - I: 2, 4 - BIS - (2'Acetyl - Phenylamino)-6-Arylamino/Substituted Amino-s-Triazines", J. Inst. Chemists, 1996, Part 1, p. 17-18, vol. 68, Part I, Chemistry Department, Saurashtra University, India.

Desai, K.R. et al., "Synthesis and Antibacterial Activity of 2,4-BIS (4-Methoxy Anilino) -6-(N-Aryl thioureido-N'-Amino Acyl)-s-Triazine Derivatives", J. Inst. Chemists, Jan. 1989, pp. 19-20, vol. 61, Department of Chemistry, South Gujarat University, India.

Pandya, U.H. et al., "Studies on Cyanuric Cholride Derivatives Part-(III)", J. Inst. Chemists, Mar. 1981, pp. 83-84, vol. 53, University Department of Chemistry, Bhavnagar University, Bhavnagar, India.

Pandya, U.H. et al., "Studies on Cyanuric Chloride Derivatives Part (II)", J. Inst. Chemists, Mar. 1981, pp. 81-82, vol. 53, University Department of Chemistry, Bhavnagar University, Bhavnagar, India.

Rajnani, H.B. et al., "Studies on Thioureas-Part-I: Preparation and Antibacterial Activityof 2,4-Diarylamino-s-Triazin-6-yl-Aminoacyl Phenylthioureas", J. Inst. Chemists, Jul. 1977, pp. 222-224, vol. 49, No. 4, University Department of Chemistry, Saurashira University, Bhavnagar, India.

Acharya, J.N. et al., "Studies on s-Triazinyl Compounds as Potential Medicinal Agents. Part II", J. Indian Chemical Society, Feb. 1976, pp. 193-195, vol. 53, University Department of Chemistry, Saurashtra University, Bhavnagar, India.

Labrecque, G.C. et al., "Substituted Melamines as Chemosterilants of House flies", Journal of Economic Entomology, Eschile and Miller: Control of Horn Flies, Dec. 1968, pp. 1621-1632, vol. 61, No. 6, Entomology Research Division, Agr. Res. Serv., USDA.

D'Alelio, G.F. et al., "Prepraration of Some Sulfanilamide Derivatives of s-Triazine[1] "0 Sulfanilamide Derivatives of s-Triazines, J. Organic Chemistry, May 1959, pp. 643-644, vol. 24, Department of Chemistry, University of Notre Dame.

Ashley, J.N., et al. "The Search for Chemotherapeutic Amidines. Part XVI. Amidinoanilino-1,3,5-triazines and Related Compounds", J. of the Chemical Society, 1960, pp. 4525-4532.

Campbell, J. Robert et al., "Unsymmetrically Substituted Melamines", J. of Organic Chemistry, Aug. 1961, pp. 2786-2789, vol. 26, The Organic Chemicals Division, Research Department, Monsanto Chemical Co.

Desai, Vikas A. et al., "2-(4'-Fluoranilino)-4-3(3'-Trifluoromethylanilino)-6-(Arylureido)-s-Triazine As Antibacterials", J. Inst. Chemicist, Part I, 2000, pp. 35-37, vol. 72, Chemistry Department South Gujarat University, Surat-395007.

Parkekh, Hansa et la., "Optically Active s-Triazine Derivatives Part I-Preparation of D(-)-2, 4-Diarylamino-6-a-Carboxybenzylamino-s-Triazines" J. Inst. Chemists, Mar. 1975, p. 63-65, vol. XLVII, University Department of Chemistry, Saurashtra University, Bhavnagar.

Khatri, Vineeta et al., "Studies in the synthesis of 2,4,6-trichloro-1,3,5-trizine derivatives", J. Indian Chemical Society, Jan. 2003, pp. 53-54, vol. 80, Department of Chemistry, University of Rajasthan, Jaipur-302 004, India, Department of Chemistry, R.L. Saharia government P.G. College, Kaladera, jaipur-303 801, India.

Desai, P.H. et al., "Preparation of 2,4-(DI 4'Fluoroanilino)-6-(Aryl Thioureido)-s-Triazine and 2-(4'-Fluoroanilino)-4-(Phenyl Thioureido)-6-(Aryl AMINO)-s-Triazine as Antibacterials", J. Inst. Chemists, Nov. 1989, pp. 207-208, vol. 61, Department of Chemistry, South gujarat University Surat-395 007.

Unishi, Terunobu et al., "Synthesis of 2, 4-Diamino-6, 7-dihydroimidazo[1, 2-a] [1, 3, 5] triazine Derivatives", The Chemical Society of Japan, 1987, pp. 40-44, vol. 1, Department of Industrial Chemistry, Faculty of Engineering, Fukui University, Bunkyo, Fukui-shi, 910, Japan. (With English Abstract).

Hashimoto, Yoshinori et al., "Thermal Stability of Melamine Derivatives and Its Application for Gas Chromatography", Kenkyu Hokoku-Asahi Garasu Kogyo Gijutsu Shoreikai, 1985, pp. 191-200, vol. 47, Department of Industrial Chemistry Faculty of Engineering, Fukui University. (With English Abstract).

Caubere, Paul et al., "Condensations d'amines sur quelques chloro-6 diamino-2,4 triazines-1,3,5 en milieu aprotique", Bulletin De La Societe Chimique De France, 1973, pp. 2112-2115, vol. No. 6.

Yamashita, Yoshio, "Photochemical Reaction of Aqueous Solution of Sodium 4, 4'-bis(2-anilino-4-monoethanolamino-1, 3, 5-triazin-6- ylamino)-2, 2'Stilbene Disulfonate", Studies of fluorescent Whitening Agents Part IV., Yuki gosei Kagaku Kyokaishi; 1972, pp. 449-456, vol. 30, No. 5. (With English Abstract).

"Diaminio-s-triazines Melamines", Nippon Hiryogaku Zasshi, 1970, pp. 193-200, vol. 41, No. 5.

Kitajima, Hidehiko et al., "Studies on Melamine Derivatives. IX., Syntheis of N—p-Hydroxybenzoylmelamines and their Use for the Synthesis of Dyes", Yuki Gosei Kagaku Kyokaishi, 12965, pp. 1116-1122, vol. 23, No. 12. (With English Abstract).

Nestler, Von Hans et al., "Uber die Darstellung von N (s-Triazinyl)-amino-saurederivaten[1] )", Journal fur praktische Chemie, 4, Reihe, Band 22, 1963, pp. 173-185.

Matsui, Kohji et al., "Reactivity of Chloro-S-triazines. II Reaction of 2, 4-dichloro-S-arylamino-S-trazines with Aniline", Yuki Gosei Kagaku Kyokaishi, 1960, pp. 184-189, vol. 18, No. 3. (With English Abstract).

Chemical Abstract Database Search, Dated Apr. 11, 2007, including registry numbers: 500532-67-2 Registry, 415701-78-9 Registry, 354540-51-5 Registry, 332409-37-7 Registry, 32285-89-5 Registry, 32285-88-4 Registry, 885512-59-4 Registry, 849705-89-1 Registry, 793652-19-4 Registry, 792904-38-2 Registry, 792904-37-1 Registry, 792849-61-7 Registry, 792184-90-8 Registry, 791779-70-9 Registry, 791583-65-8 Registry, 790656-37-0 Registry, 790205-55-9 Registry, 790205-54-8 Registry, 788819-69-2 Registry, 785773-979- Registry, 784136-97-96 Registry, 782447-23-8 Registry, 781611-85-6 Registry, 780751-44-2 Registry, 780035-62-3 Registry, 779322-54-2 Registry, 778573-02-7 Registry, 776292-03-6 Registry, 775576-74-4 Registry, 775282-40-1 Registry, 774535-72-7 Registry, 774179-87-2 Registry, 773846-27-8 Registry, 773052-41-8 Registry, 772997-72-5 Registry, 772336-63-7 Registry, 771473-16-6 Registry, 770706-78-0 Registry, 768357-51-3 Registry, 768357-50-2 Registry, 768302-84-7 Registry, 767284-63-9 Registry, 766505-79-7 Registry, 765897-13-0 Registry, 764645-34-3 Registry, 763924-05-6 Registry, 761398-29-2 Registry, 760942-70-9 Registry, 760170-99-8 Registry, 759455-37-3 Registry, 758682-95-0 Registry, 757939-34-7 Registry, 756815-61-9 Registry, 756473-90-2 Registry, 755750-79-9 Registry,754975-21-8 Registry, 754183-24-9 Registry, 753447-12-0 Registry, 752981-32-1 Registry, 751423-47-9 Registry, 749846-29-5 Registry,749205-62-7 Registry, 748766-95-2 Registry, 748129-80-8 Registry, 748075-15-2 Registry, 747407-43-8 Registry, 742055-12-5 Registry, 741668-74-6 Registry, 740080-81-3 Registry, 739362-22-2 Registry, 738577-49-6 Registry, 736132-85-7 Registry, 734518-73-1 Registry, 727358-35-2 Registry, 724421-

07-2 Registry, 700803-55-0 Registry, 688308-58-9 Registry, 685087-34-7 Registry, 499986-17-3 Registry, 400739-51-7 Registry, 382152-28-5 Registry, 371199-71-2 Registry, 351424-95-8 Registry, 339004-35-2 Registry, 331967-99-8 Registry, 331967-97-6 Registry, 311325-73-2 Registry, 294651-23-3 Registry, 775231-17-9 Registry, 769897-79-2 Registry, 759434-64-5 Registry, 756764-40-6 Registry, 756453-21-1 Registry, 754132-12-2 Registry, 748715-76-6 Registry, 745005-53-2 Registry, 722451-61-8 Registry, 311314-43-9 HCAPLUS, 351188-66-4 HCAPLUS, 2006-410059 HCAPLUS, 885476-12-0 HCAPLUS, 2006:87910 HCAPLUS, 433689-56-6 HCAPLUS, 311314-43-9 HCAPLUS, 311781-50-7 HCAPLUS, 331968-00-4 HCAPLUS, 876741-04-7 HCAPLUS, 876741-07-0 HCAPLUS, 246860-71-9 HCAPLUS, 286860-73-1 HCAPLUS, 246860-74-2 HCAPLUS, 246860-77-5 HCAPLUS, 117488-59-2 HCAPLUS, 117488-60-5 HCAPLUS, 849705-90-4 HCAPLUS, 849705-91-5 HCAPLUS, 246860-71-9 HCAPLUS, 246860-73-1 HCAPLUS, 246860-74-2 HCAPLUS, 246860-77-5 HCAPLUS, 808735-33-3 HCAPLUS, 808735-34-4 HCAPLUS, 808735-33-3 HCAPLUS,
676358-18-2 HCAPLUS, 676360-74-0 HCAPLUS, 676358-18-2 HCAPLUS, 676360-74-0 HCAPLUS, 676360-74-0 HCAPLUS, 676358-18-2 HCAPLUS, 676360-74-0 HCAPLUS, 17654-47-6 HCAPLUS, 17654-48-7 HCAPLUS, 17654-49-8 HCAPLUS, 51349-88-3 HCAPLUS, 107274-03-3 HCAPLUS, 109002-62-2 HCAPLUS, 113310-62-6 HCAPLUS, 156126-89-5 HCAPLUS, 203192-22-7 HCAPLUS, 310457-41-1 HCAPLUS, 311314-43-9 HCAPLUS, 311788-90-6 HCAPLUS, 332150-96-6 HCAPLUS, 332409-24-2 HCAPLUS, 343350-99-2 HCAPLUS, 350477-04-2 HCAPLUS, 578009-22-0 HCAPLUS, 578009-23-1 HCAPLUS, 578009-24-2 HCAPLUS, 578009-25-3 HCAPLUS, 578009-26-4 HCAPLUS, 578009-27-5 HCAPLUS, 578009-32-2 HCAPLUS, 578009-34-4 HCAPLUS, 578009-36-6 HCAPLUS, 578009-39-9 HCAPLUS, 578009-43-5 HCAPLUS, 578009-49-1 HCAPLUS, 578009-50-4 HCAPLUS, 578009-51-5 HCAPLUS, 578009-52-6 HCAPLUS, 578009-55-9 HCAPLUS, 578009-56-0 HCAPLUS, 578009-61-7 HCAPLUS, 578010-18-1 HCAPLUS, 578010-19-2 HCAPLUS, 578010-20-5 HCAPLUS, 578010-21-6 HCAPLUS, 578001022-7 HCAPLUS, 578010-23-8 HCAPLUS, 578010-24-9 HCAPLUS, 578010-25-0 HCAPLUS, 578010-26-1 HCAPLUS, 578010-27-2 HCAPLUS, 578010-53-2 HCAPLUS, 578010-36-3 HCAPLUS, 578010-37-4 HCAPLUS, 578010-38-5 HCAPLUS, 578010-48-7 HCAPLUS, 578010-50-1 HCAPLUS, 578010-52-3 HCAPLUS, 578010-53-4 HCAPLUS, 578010-54-5 HCAPLUS, 578010-55-6 HCAPLUS, 578010-61-4 HCAPLUS, 578010-62-5 HCAPLUS, 578010-63-6 HCAPLUS, 578010-64-7 HCAPLUS, 578011-13-9 HCAPLUS, 578011-14-0 HCAPLUS, 578011-15-1 HCAPLUS, 578011-16-2 HCAPLUS, 578011-17-3 HCAPLUS, 578011-48-0 HCAPLUS, 578011-49-1 HCAPLUS, 578011-50-4 HCAPLUS, 578011-51-5 HCAPLUS, 578011-52-6 HCAPLUS, 578011-55-9 HCAPLUS, 578011-61-7 HCAPLUS, 578011-62-8 HCAPLUS, 578011-63-9 HCAPLUS, 578011-64-0 HCAPLUS, 578011-67-3 HCAPLUS, 578011-68-4 HCAPLUS, 578011-69-5 HCAPLUS, 578011-70-8 HCAPLUS, 578016-29-2 HCAPLUS, 578016-30-5 HCAPLUS, 578016-32-7 HCAPLUS, 578016-33-8 HCAPLUS, 578016-34-9 HCAPLUS, 578016-35-0 HCAPLUS, 578016-36-1 HCAPLUS, 578016-37-2 HCAPLUS, 578016-38-3 HCAPLUS, 578016-39-4 HCAPLUS, 578016-40-7 HCAPLUS, 578016-41-8 HCAPLUS, 578016-42-9 HCAPLUS, 578016-43-0 HCAPLUS, 578015-44-1 HCAPLUS, 578016-45-2 HCAPLUS, 578016-46-3 HCAPLUS, 578016-47-4 HCAPLUS, 578016-48-5 HCAPLUS, 578016-49-6 HCAPLUS, 578016-50-9 HCAPLUS, 578016-51-0 HCAPLUS, 578016-53-2 HCAPLUS, 578016-54-3 HCAPLUS, 578016-55-4 HCAPLUS, 578016-56-5 HCAPLUS, 578016-57-6 HCAPLUS, 578016-58-7 HCAPLUS,
578016-61-2 HCAPLUS, 578016-84-9 HCAPLUS, 578016-85-0 HCAPLUS, 578016-86-1 HCAPLUS, 578016-87-2 HCAPLUS, 578016-88-3 HCAPLUS, 578016-89-4 HCAPLUS, 578016-90-7 HCAPLUS, 578016-91-8 HCAPLUS, 578016-92-9 HCAPLUS, 578016-93-0 HCAPLUS, 578016-94-1 HCAPLUS, 578016-95-2 HCAPLUS, 578016-96-3 HCAPLUS, 578016-98-5 HCAPLUS, 578016-99-6 HCAPLUS, 578017-00-2 HCAPLUS, 578018-01-3 HCAPLUS, 578017-02-4 HCAPLUS, 578017-03-5 HCAPLUS, 578017-04-6 HCAPLUS, 578017-05-7 HCAPLUS, 578017-06-8 HCAPLUS, 578017-07-9 HCAPLUS, 578017-08-0 HCAPLUS, 578018-09-1 HCAPLUS, 578017-10-4 HCAPLUS, 412284-47-0 HCAPLUS, 412284-49-2 HCAPLUS, 412284-50-5 HCAPLUS, 412284-51-6 HCAPLUS, 412284-55-0 HCAPLUS, 412284-56-1 HCAPLUS, 412284-58-3 HCAPLUS, 412284-60-7 HCAPLUS, 232937-01-8 HCAPLUS, 232937-02-9 HCAPLUS, 232937-06-3 HCAPLUS, 232937-41-6 HCAPLUS, 232937-44-9 HCAPLUS, 232937-55-2 HCAPLUS, 232937-59-6 HCAPLUS, 359873-39-5 HCAPLUS, 345206-49-7 HCAPLUS, 345206-50-0 HCAPLUS, 324055-78-9 HCAPLUS, 324055-80-3 HCAPLUS, 324055-84-7 HCAPLUS, 324056-00-0 HCAPLUS, 324056-02-2 HCAPLUS, 324056-04-4 HCAPLUS, 324056-06-6 HCAPLUS, 308290-55-3 HCAPLUS, 308290-56-4 HCAPLUS, 308290-57-5 HCAPLUS, 308290-58-6 HCAPLUS, 308290-59-7 HCAPLUS, 308290-60-0 HCAPLUS, 308290-61-1 HCAPLUS, 308290-62-2 HCAPLUS, 308290-63-3 HCAPLUS, 308290-64-4 HCAPLUS, 233685-61-5 HCAPLUS, 246860-71-9 HCAPLUS, 246860-73-1 HCAPLUS, 246860-74-2 HCAPLUS, 246860-77-5 HCAPLUS, 233685-61-5 HCAPLUS, 232937-01-8 HCAPLUS, 232937-02-9 HCAPLUS, 232937-06-3 HCAPLUS, 232937-41-6 HCAPLUS, 232937-44-9 HCAPLUS, 232937-55-2 HCAPLUS, 232937-59-6 HCAPLUS, 226909-73-5 HCAPLUS, 226909-74-6 HCAPLUS, 226909-75-7 HCAPLUS, 226909-76-8 HCAPLUS, 17654-47-6 HCAPLUS, 107274-03-3 HCAPLUS, 156126-89-5 HCAPLUS, 219817-00-2 HCAPLUS, 219817-04-6 HCAPLUS, 219817-37-5 HCAPLUS, 204268-83-7 HCAPLUS, 204268-93-9 HCAPLUS, 204268-82-6 HCAPLUS, 204268-89-3 HCAPLUS, 204268-94-0 HCAPLUS, 203192-22-7 HCAPLUS, 189249-43-2 HCAPLUS, 183483-88-7 HCAPLUS, 172320-00-2 HCAPLUS, 172320-01-3 HCAPLUS, 172320-02-4 HCAPLUS, 169523-45-9 HCAPLUS, 169523-46-0 HCAPLUS, 169523-47-1 HCAPLUS, 169523-48-2 HCAPLUS, 170442-21-4 HCAPLUS, 156126-89-5 HCAPLUS, 153630-51-4 HCAPLUS, 146004-65-1 HCAPLUS, 144237-70-7 HCAPLUS, 131468-39-8 HCAPLUS, 131468-43-4 HCAPLUS, 131468-44-5 HCAPLUS, 131468-51-4 HCAPLUS, 131468-53-6 HCAPLUS, 131468-35-4 HCAPLUS, 131468-36-5 HCAPLUS, 131468-37-6 HCAPLUS, 131468-38-7 HCAPLUS, 131468-40-1 HCAPLUS, 131468-41-2 HCAPLUS, 131468-42-3 HCAPLUS,
131468-45-6 HCAPLUS, 131468-46-7 HCAPLUS, 131468-47-8 HCAPLUS, 131468-48-9 HCAPLUS, 131468-49-0 HCAPLUS, 131468-50-3 HCAPLUS, 131468-52-5 HCAPLUS, 65052-35-9 HCAPLUS, 126086-26-8 HCAPLUS, 126086-27-9 HCAPLUS, 126086-28-0 HCAPLUS, 62751-90-0 HCAPLUS, 65052-23-5 HCAPLUS, 99100-89-7 HCAPLUS, 117488-39-8 HCAPLUS, 117488-40-1 HCAPLUS, 117488-41-2 HCAPLUS, 117488-42-3 HCAPLUS, 117488-43-4 HCAPLUS, 117488-44-5 HCAPLUS, 117488-45-6 HCAPLUS, 117488-46-7 HCAPLUS, 117488-47-8 HCAPLUS, 117488-48-9 HCAPLUS, 117488-49-0 HCAPLUS, 117488-50-3 HCAPLUS, 117488-51-4 HCAPLUS, 117488-52-5 HCAPLUS, 117488-53-6 HCAPLUS, 117488-54-7 HCAPLUS, 117488-55-8 HCAPLUS, 117488-56-9 HCAPLUS, 117488-57-0 HCAPLUS, 117488-58-1 HCAPLUS, 117488-59-2 HCAPLUS, 117488-60-5 HCAPLUS, 117488-61-6 HCAPLUS, 65052-18-8 HCAPLUS, 116923-54-7 HCAPLUS, 116923-55-8 HCAPLUS, 116923-56-9 HCAPLUS, 116923-57-0 HCAPLUS, 116923-58-1 HCAPLUS, 116923-59-2 HCAPLUS, 116923-60-5 HCAPLUS, 116923-61-6 HCAPLUS, 51349-88-3 HCAPLUS, 114806-02-9 HCAPLUS, 114806-03-0 HCAPLUS, 114806-04-1 HCAPLUS, 114806-05-2 HCAPLUS, 114806-06-3 HCAPLUS, 114806-07-4 HCAPLUS, 114806-08-5 HCAPLUS, 114806-09-6 HCAPLUS, 114806-11-0 HCAPLUS, 114806-12-1 HCAPLUS, 114806-13-2 HCAPLUS, 114806-14-3 HCAPLUS, 114806-15-4 HCAPLUS, 114825-01-3 HCAPLUS, 113310-62-6 HCAPLUS, 113310-63-7 HCAPLUS, 113310-64-8 HCAPLUS, 113310-65-9 HCAPLUS, 113310-66-0 HCAPLUS, 113310-67-1 HCAPLUS, 113310-68-2 HCAPLUS, 113310-69-3 HCAPLUS, 113310-70-6 HCAPLUS, 113310-71-7 HCAPLUS, 113310-72-8 HCAPLUS, 113310-73-9 HCAPLUS, 113310-74-0 HCAPLUS, 113310-75-1 HCAPLUS, 113310-76-2 HCAPLUS, 110363-98-9 HCAPLUS, 110363-97-8 HCAPLUS, 99100-89-7 HCAPLUS, 109002-62-2 HCAPLUS, 109002-63-3 HCAPLUS, 109002-64-4 HCAPLUS, 109002-65-5 HCAPLUS, 109002-66-6 HCAPLUS, 109002-67-7 HCAPLUS, 109002-68-8 HCAPLUS, 109002-69-9 HCAPLUS, 109002-70-2

HCAPLUS, 109002-71-3 HCAPLUS, 109002-72-4 HCAPLUS, 109002-73-5 HCAPLUS, 109002-74-6 HCAPLUS, 108026-02-4 HCAPLUS, 107830-21-7 HCAPLUS, 19860-91-4 HCAPLUS, 100033-29-2 HCAPLUS, 98223-73-5 HCAPLUS, 98223-74-6 HCAPLUS, 98223-75-7 HCAPLUS, 65052-30-4 HCAPLUS, 91437-74-0 HCAPLUS, 91437-75-1 HCAPLUS, 91437-76-2 HCAPLUS, 91437-77-3 HCAPLUS, 91437-78-4 HCAPLUS, 91437-79-5 HCAPLUS, 91437-80-8 HCAPLUS, 91437-81-9 HCAPLUS, 65052-18-8 HCAPLUS, 78912-83-1 HCAPLUS, 78912-97-7 HCAPLUS, 72129-07-8 HCAPLUS, 72129-08-9 HCAPLUS,72129-09-0 HCAPLUS, 72129-11-4 HCAPLUS, 72129-12-5 HCAPLUS, 72129-15-8 HCAPLUS, 72129-16-9 HCAPLUS, 72148-27-7 HCAPLUS, 56125-37-2 HCAPLUS, 56125-40-7 HCAPLUS, 56125-41-8 HCAPLUS, 56125-42-9 HCAPLUS, 56125-43-0 HCAPLUS, 65052-30-4 HCAPLUS, 65052-31-5 HCAPLUS, 65052-32-6 HCAPLUS, 65052-33-7 HCAPLUS, 65052-34-8 HCAPLUS, 65052-35-9 HCAPLUS, 65052-36-0 HCAPLUS, 62751-85-3 HCAPLUS, 62751-86-4 HCAPLUS, 62751-87-5 HCAPLUS, 62751-88-6 HCAPLUS, 62751-89-7 HCAPLUS, 62751-90-0 HCAPLUS, 62751-91-1 HCAPLUS, 62751-92-2 HCAPLUS, 62751-93-3 HCAPLUS, 65052-16-6 HCAPLUS, 65052-17-7 HCAPUS, 65052-18-8 HCAPLUS, 65052-19-9 HCAPLUS, 65052-20-2 HCAPLUS, 65052-21-3 HCAPLUS, 65052-22-4 HCAPLUS, 65052-23-5 HCAPLUS, 65052-24-6 HCAPLUS, 65052-25-7 HCAPLUS, 65052-26-8 HCAPLUS, 65052-27-9 HCAPLUS, 65052-28-0 HCAPLUS, 64530-95-6 HCAPLUS, 64530-96-7 HCAPLUS, 64531-02-8 HCAPLUS, 64531-05-1 HCAPLUS, 64531-09-5 HCAPLUS, 64531-11-9 HCAPLUS, 62751-85-3 HCAPLUS, 62751-86-4 HCAPLUS, 62751-87-5 HCAPLUS, 62751-88-6 HCAPLUS, 62751-89-7 HCAPLUS, 62751-90-0 HCAPLUS, 62751-91-1 HCAPLUS, 62751-92-2 HCAPLUS, 62751-93-3 HCAPLUS, 62751-95-5 HCAPLUS, 62751-96-6 HCAPLUS, 62751-97-7 HCAPLUS, 62751-98-8 HCAPLUS, 62751-99-9 HCAPLUS, 62752-00-5 HCAPLUS, 62752-01-6 HCAPLUS, 62752-03-8 HCAPLUS, 60140-04-7 HCAPLUS, 60140-05-8 HCAPLUS, 60140-06-9 HCAPLUS, 60140-07-0 HCAPLUS, 60140-10-5 HCAPLUS, 60140-27-4 HCAPLUS, 60140-28-5 HCAPLUS, 58889-28-4 HCAPLUS, 57135-76-9 HCAPLUS, 57135-77-0 HCAPLUS,
57135-78-1 HCAPLUS, 57135-79-2 HCAPLUS, 57135-80-5 HCAPLUS, 57135-81-6 HCAPLUS, 57135-83-8 HCAPLUS, 57135-84-9 HCAPLUS, 56125-37-2 HCAPLUS, 56125-40-7 HCAPLUS, 56125-41-8 HCAPLUS, 56125-42-9 HCAPLUS, 56125-43-0 HCAPLUS, 56808-29-8 HCAPLUS, 56125-37-2 HCAPLUS, 56125-40-7 HCAPLUS, 56125-41-8 HCAPLUS, 56125-42-9 HCAPLUS, 56125-43-0 HCAPLUS, 51349-88-3 HCAPLUS, 17654-48-7 HCAPLUS, 36434-23-8 HCAPLUS,38331-74-7 HCAPLUS, 30360-22-6 HCAPLUS, 28053-79-4 HCAPLUS, 28053-80-7 HCAPLUS, 28053-81-8 HCAPLUS, 28053-82-9 HCAPLUS, 19523-49-0 HCAPLUS, 19860-91-4 HCAPLUS, 17139-46-7 HCAPLUS, 17139-47-8 HCAPLUS, 17233-75-9 HCAPLUS, 17654-47-6 HCAPLUS, 17654-48-7 HCAPLUS, 17654-49-8 HCAPLUS, 17654-50-1 HCAPLUS, 17654-51-2 HCAPLUS, 17774-61-7 HCAPLUS, 4948-10-1 HCAPLUS, 6827-94-7 HCAPLUS, 4839-43-4 HCAPLUS, 96969-28-7 HCAPLUS, 103837-65-6 HCAPLUS, 106504-65-8 HCAPLUS, 101896-49-5 HCAPLUS, 99100-89-7 HCAPLUS, 106572-42-3 HCAPLUS, 19860-91-4 HCAPLUS, 109568-47-0 HCAPLUS, 110058-99-6 HCAPLUS, 115122-82-2 HCAPLUS, 110441-48-0 HCAPLUS, 109731-59-1 HCAPLUS, 17654-47-6 HCAPLUS, 17654-48-7 HCAPLUS, 107274-03-3 HCAPLUS.

* cited by examiner

2,4,6-TRIAMINO-1,3,5-TRIAZINE DERIVATIVE

TECHNICAL FIELD

This invention relates to medicaments, particularly an anti-dementia agent which comprises a substance having BEC 1 potassium channel inhibitory action as the active ingredient, preferably an anti-dementia agent wherein the substance having BEC 1 potassium channel inhibitory action is a 2,4,6-triamino-1,3,5-triazine derivative or a pharmaceutically acceptable salt thereof, and a novel 2,4,6-triamino-1,3,5-triazine derivative or a pharmaceutically acceptable salt thereof.

BACKGROUND OF THE INVENTION

Potassium channel is a protein which distributes in the plasma membrane of cells and lets potassium ions selectively pass trough it and is considered to be taking an important role in controlling membrane potential of cells. Particularly, this is contributing to the neurotransmission of central and peripheral nerves, pace-making of the heart, contraction of muscles and the like by regulating frequency, persistency and the like of action potential in nerve and muscle cells.

As the classification based on the opening and closing mechanism of the channel, a voltage-dependent potassium channel, an inwardly rectifying potassium channel, a calcium-dependent potassium channel, a receptor coupling type potassium channel and the like have so far been identified. Among them, the voltage-dependent potassium channel has a property to open it when the membrane potential is depolarized. In general, potassium ions are present in a non-equilibrium state of about 5 mM in the extracellular moiety and about 150 mM in the intracellular moiety. Accordingly, when the voltage-dependent potassium channel is opened due to depolarization, potassium ions flow out from the intracellular part into the extracellular part and cause restoration (re-polarization) of membrane potential as a result. Thus, reduction of excitability of nerve and muscle calls is induced accompanied by the opening of the voltage-dependent channel [Non-patent reference 1].

Compounds capable of modifying opening of the voltage-dependent channel have a possibility to regulate various physiological phenomena by regulating excitability of nerve and muscle cells and therefore to become therapeutic drugs of various diseases.

For example, it is known that 4-aminopyridine which is an inhibitor of the A type voltage-dependent potassium channel found in nerve cells causes epilepsy by increasing excitability of nerves [Non-patent reference 3]. In addition, dofetilide which is an inhibitor of HERG potassium channel expressing in the heart, among voltage-dependent potassium channels, is used as an agent for treating arrhythmia based on its property to control excitability of cardiac muscle cells [Non-patent reference 4].

The potassium channel described as SEQ ID NO:2 in Example 1 of U.S. Pat. No. 6,326,168 (corresponding international patent publication pamphlet WO 99/37677) [Patent reference 1] (to be referred to as BEC 1 or BEC 1 potassium channel hereinafter) is a voltage-dependent potassium channel which shows an expression distribution localized to the brain. Its expression is significant particularly in the hippocampus and cerebral cortex. The hippocampus is a region whose relation to memory and learning are strongly suggested [Non-patent reference 5].

Particularly, granule cells of dentate gyrus and CA 1 and CA 3 pyramidal cells wherein BEC 1 potassium channel expresses form a neural circuit, and input of various memories is transmitted from the granule cells of dentate gyrus to the CA 3 pyramidal cell through the CA 1 pyramidal cell, via an excitatory synapse which uses glutamic acid as the neurotransmitter. It is considered that long-term changes in the long-term potentiation, long-term depression and the like synaptic transmission efficiencies found in respective synapses are deeply concerned in the memory and learning. These long-term changes are regulated by the excitation frequency and excitation strength of nerve cells. In addition, the voltage-dependent potassium channel generally has a possibility of being able to control excitability of nerve cells.

Accordingly, it is considered that BEC 1 is concerned in the formation of memory and learning via the excitability control of nerve cells, but this has not been illustratively proved.

A large number of 2,4,6-triamino-1,3,5-triazine derivatives are currently known, and their uses are disclosed as an anti-HIV agent [Non-patent reference 6], an adenosine A 3 antagonist [Patent reference 2], and antimicrobial agents [Non-patent reference 7], [Non-patent reference 8], [Non-patent reference 9] and [Patent reference 3]. Though many potassium channel inhibitors and 2,4,6-triamino-1,3,5-triazine derivatives have so far been reported [Patent reference 3] and [Non-patent reference 10], there are no reports or suggestions stating that they have BEC 1 potassium channel inhibitory action.

The object of the invention is to provide an anti-dementia agent which uses a substance having BEC 1 potassium channel inhibitory action (to be referred to as BEC 1 potassium channel inhibitor hereinafter) as the active ingredient, preferably an anti-dementia agent wherein the BEC 1 potassium channel inhibitor is a 2,4,6-triamino-1,3,5-triazine derivative or a pharmaceutically acceptable salt thereof, a novel 2,4,6-triamino-1,3,5-triazine derivative having BEC 1 potassium channel inhibitory action or a pharmaceutically acceptable salt thereof, and a medicament comprising said novel derivative or a pharmaceutically acceptable salt thereof.

The present inventors have conducted studies with the aim of achieving the above object and found as a result that a BEC 1 potassium channel inhibitor can become an anti-dementia agent. In addition, it was found unexpectedly that a compound having the 2,4,6-triamino-1,3,5-triazine structure has a BEC 1 potassium channel inhibitory action, thus resulting in the accomplishment of the invention.

[Non-Patent Reference 1]
  Hille, B. (ed), Ionic Channels of Excitable Membranes (Sinauer Associates, Sunderland, 1992)
[Non-Patent Reference 2]
  Catterall, W. A., Chandy, K. G. & Gutman G. A. (eds), The IUPHAR Compendium of Voltage-gated Ion Channels (IUPHAR Media, Leeds, UK, 2002)
[Non-Patent Reference 3]
  Yamaguchi, S. and Rogawski, M. A., *Epilepsy Res.*, 11: 9-16 (1992)
[Non-Patent Reference 4]
  Gwilt, M., Arrowsmith, J. E., Blackburn, K. J., Burges, R. A., Cross, P. E., Dalrymple, H. W. and Higgins, A. J., *J. Pharmacol. Exp. Ther.*, 256: 318-324 (1991)
[Non-Patent Reference 5]
  Levitan, I. B. and Kaczmarek L. K. (1991), The Neuron: Cell and Molecular Biology, Oxford University Press, New York, N.Y.

[Non-Patent Reference 6]
  Bioorg. Med. Chem. Lett., (2001) 11, 2229-2234
[Non-Patent Reference 7]
  Acta Cienc. Indica. Chem., (1992) 18(4), 405-406
[Non-Patent Reference 8]
  Acta Cienc. Indica. Chem., (1985) 11(1), 66-70
[Non-Patent Reference 9]
  J. Indian Chemical Society, (1987) 64(12), 770-771
[Non-Patent Reference 10]
  J. Inst. Chem. (India), (1987) 59(4), 183-185
[Patent Reference 1]
  U.S. Pat. No. 6,326,168
[Patent Reference 2]
  JP-A-11-158073
[Patent Reference 3]
  International Publication Pamphlet WO 99/1442

DISCLOSURE OF THE INVENTION

The invention relates to an anti-dementia agent which comprises a substance having BEC 1 potassium channel inhibitory action as the active ingredient.

It is preferably an anti-dementia agent wherein the substance having BEC 1 potassium channel inhibitory action is a 2,4,6-triamino-1,3,5-triazine derivative represented by a formula (I) or a pharmaceutically acceptable salt thereof

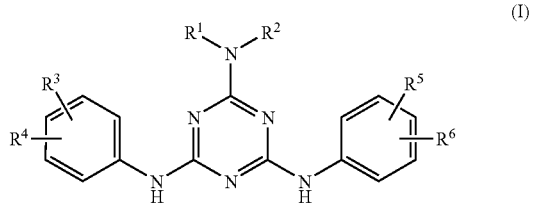

(symbols in the formula are as follows $R^1$ and $R^2$: the same or different from each other, and each represents H, OH, an alkyl-O—, an aryl-CO—, $H_2N$, an alkyl-NH which may be substituted with OH, an $(alkyl)_2N$, a hydrocarbon radical which may be substituted or a hetero ring which may be substituted, or $R^1$, $R^2$ and the adjacent N may together form a nitrogen-containing hetero ring and said ring may be substituted, $R^3$, $R^4$, $R^5$ and $R^6$: the same or different from one another, and each represents (i) H, (ii) CN, (iii) $NO_2$, (iv) a halogen, (v) a lower alkyl which may be substituted with (1) CN, (2) a halogen or (3) OH, (vi) a cycloalkyl, (vii) an aryl which may be substituted with a lower alkyl, (ix) a hetero ring which may be substituted with a lower alkyl, (x) $R^7R^8N$— ($R^7$ and $R^8$: the same or different from each other, and each represents (1) H or (2) a lower alkyl which may be substituted with an aryl or $R^9$—O—CO— ($R^9$: (1) H or a lower alkyl which may be substituted with an aryl), (xi) $R^{10}$-$T^1$- ($R^{10}$: (1) H, (2) a lower alkyl which may be substituted with an aryl, an HO—$C_{1-10}$ alkylene-O— or HO or (3) an aryl, $T^1$: O or S), or (xii) $R^{11}$-$T^2$- ($R^{11}$: (1) OH, (2) $R^7R^8N$—, (3) a lower alkyl-O—, (4) a lower alkyl, (5) an aryl or (6) a hetero ring, ($T^2$: CO or $SO_2$)), further, $R^3$, $R^4$ and the adjacent C, or $R^5$, $R^6$ and the adjacent C, may together form a hetero ring or cyclic hydrocarbon ring, and the ring may be condensed with a benzene ring).

Another embodiment of the invention is BEC 1 potassium channel described as SEQ ID NO:2 inhibitor having a 2,4,6-triamino-1,3,5-triazine derivative represented by a formula (I) or a pharmaceutically acceptable salt thereof as an ingredient.

Also, another embodiment of the invention is a 2,4,6-triamino-1,3,5-triazine derivative represented by a formula (II) or a pharmaceutically acceptable salt thereof

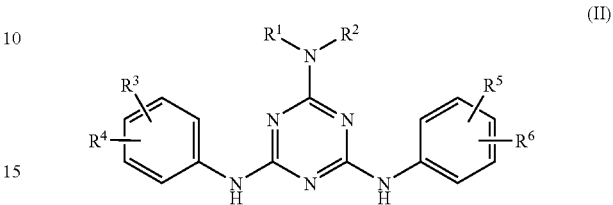

(symbols in the formula are as follows $R^1$ and $R^2$: the same or different from each other, and each represents H, OH, an alkyl-O—, an aryl-CO—, $H_2N$, an alkyl-NH which may be substituted with OH, an $(alkyl)_2N$, a hydrocarbon radical which may be substituted or a hetero ring which may be substituted, or $R^1$, $R^2$ and the adjacent N may together form a nitrogen-containing hetero ring and said ring may be substituted, $R^3$, $R^4$, $R^5$ and $R^6$: the same or different from one another, and each represents (i) H, (ii) CN, (iii) $NO_2$, (iv) a halogen, (v) a lower alkyl which may be substituted with (1) CN, (2) a halogen or (3) OH, (vi) a cycloalkyl, (vii) an aryl which may be substituted with a lower alkyl, (ix) a hetero ring which may be substituted with a lower alkyl, (x) $R^7R^8N$— ($R^7$ and $R^8$: the same or different from each other, and each represents (1) H or (2) a lower alkyl which may be substituted with an aryl or $R^9$—O—CO— ($R^9$: (1) H or a lower alkyl which may be substituted with an aryl), (xi) $R^{10}$-$T^1$- ($R^{10}$: (1) H, (2) a lower alkyl which may be substituted with an aryl, an HO—$C_{1-10}$ alkylene-O— or HO or (3) an aryl, $T^1$: O or S), or (xii) $R^{11}$-$T^2$- ($R^{11}$: (1) OH, (2) $R^7R^8N$—, (3) a lower alkyl-O—, (4) a lower alkyl, (5) an aryl or (6) a hetero ring, ($T^2$: CO or $SO_2$)), further, $R^3$, $R^4$ and the adjacent C, or $R^5$, $R^6$ and the adjacent C, may together form a hetero ring or cyclic hydrocarbon ring, and the ring may be condensed with a benzene ring), excluding a case in which $R^1$ and $R^2$ in the aforementioned formula (II) are the same or different from each other, and each represents (i) H, $NH_2$, a cyclohexyl, phenyl which may be substituted, $R^a$—$(CH_2)_2$— ($R^a$: HS, HO, $R^7R^8N$, COOH, an ethoxy, CN, morpholino or chloro), an alkyl which may be substituted with a substituent group of the following (a) to (e) ((a), HOOC, (b) an alkyl-O—CO—, (c) phenyl which may be substituted, (d) $R^7R^8$NCONHCO or (e) $R^7R^8$NCONHCO—), an alkenyl, phenyl-S—, phenyl-$SO_2$—, phenyl-NHCS— which may be substituted, phenyl-NHCO— which may be substituted, an alkyl-O—CO—, $H_2$NCS, chloro-$COCH_2$— or 1,3,4-oxadiazol-2-ylmethyl which may be substituted, or $R^1$, $R^2$ and the adjacent C together form pyrazol-1-yl, indol-1-yl, indazol-2-yl, piperidin-1-yl or morpholin-4-yl and $R^3$, $R^4$, $R^5$ and $R^6$ are the same or different from one another and each represents H, a halogen, $NO_2$, acetyl, HO, a lower alkyl-O—, HOOC—, a lower alkyl-O—CO—, $H_2NSO_2$— or a lower alkyl; the same shall apply thereinafter).

Still another embodiment of the invention is a medicament which comprises the 2,4,6-triamino-1,3,5-triazine derivative described by the aforementioned formula (II) or a pharmaceutically acceptable salt thereof.

Preferred embodiment of the invention is a 2,4,6-triamino-1,3,5-triazine derivative or a pharmaceutically acceptable salt thereof having the following substituent groups in the formula (I) or formula (II);

(1) $R^1$ and $R^2$ are different from each other and are H and a hydrocarbon radical which may be substituted, and the hydrocarbon radical is more preferably an alkyl, further preferably a hetero ring-substituted alkyl which may be substituted, (2) $R^1$ and $R^2$ are different from each other and are H and a hetero ring which may be substituted, and said hetero ring is more preferably a four- to six-membered single ring containing 1 or 2 hetero atoms selected from S and O, (3) $R^3$, $R^4$, $R^5$ and $R^6$ are H, (4) $R^3$, $R^4$, $R^5$ and $R^6$ are the same or different from one another and are H and a halogen, (5) $R^3$, $R^4$, $R^5$ and $R^6$ are the same or different from one another and are H and a lower alkyl which may be substituted with [(1) a halogen or (2) OH], (6) $R^3$, $R^4$, $R^5$ and $R^6$ are the same or different from one another and are H, a halogen and a lower alkyl which may be substituted with [(1) a halogen or (2) OH], (7) $R^3$, $R^4$, $R^5$ and $R^6$ are the same or different from one another and are H and $R^{10}$-$T^1$-, or (8) $R^3$, $R^4$, $R^5$ and $R^6$ are the same or different from one another and are H, a halogen and $R^{10}$-$T^1$-.

Particularly preferred is a 2,4,6-triamino-1,3,5-triazine derivative or a pharmaceutically acceptable salt thereof, having a combination of the aforementioned (1) or (2) with any one of (3) to (8).

Preferred compound is any one of the 2,4,6-triamino-1,3,5-triazine derivatives shown in the following table or a pharmaceutically acceptable salt thereof.

TABLE 1

(The numbers 2 to 6 in the formula above represent respective bonding positions of R3 and R5.)

| $\overset{R^1\quad R^2}{\underset{|}{N}}$ | $R^3$ | $R^5$ |
|---|---|---|
| Py-4-ylCH$_2$NH— | H | H |
| Py-3-ylCH$_2$NH— | H | H |
| Py-2-ylCH$_2$NH— | H | H |
| 2-FPy-4-ylCH$_2$NH— | H | H |
| 2-ClPy-4-ylCH$_2$NH— | H | H |
| 2-iPrPy-4-ylCH$_2$NH— | H | H |
| BzlNH— | H | H |
| 4-FPhCH$_2$NH— | H | H |
| Py-4-yl(CH$_2$)$_2$NH— | H | H |
| 2-FPy-4-ylCH$_2$NH— | H | 3,4-diF |
| 2-FPy-4-ylCH$_2$NH— | H | 4-MeO |
| 2-FPy-4-ylCH$_2$NH— | 4-Me | 4-F |
| HN-CH$_2$-furan-Me | H | H |

TABLE 1-continued (The numbers 2 to 6 in the formula above represent respective bonding positions of R3 and R5.)

| $\overset{R^1\quad R^2}{\underset{|}{N}}$ | $R^3$ | $R^5$ |
|---|---|---|
| HN-CH$_2$-thiophene | H | H |
| HN-CH$_2$-furan | H | H |
| HN-CH$_2$-furan | H | 4-Me |
| Py-4-ylCH$_2$NH— | 4-F | 4-F |
| Py-3-ylCH$_2$NH— | 4-F | 4-F |
| Py-2-ylCH$_2$NH— | 4-F | 4-F |
| BzlNH— | 4-F | 4-F |
| 4-FPhCH$_2$NH— | 4-F | 4-F |
| Py-4-yl(CH$_2$)$_2$NH— | H | H |
| HCCCH$_2$NH— | H | H |
| MeO(CH$_2$)$_2$NH— | H | H |
| MeO(CH$_2$)$_3$NH— | H | H |
| 2-FPy-4-ylCH$_2$NH— | 4-F | 4-F |
| 2-FPy-4-ylCH$_2$NH— | H | 4-F |
| 2-MePy-4-ylCH$_2$NH— | H | 4-F |
| 2-FPy-4-ylCH$_2$NH— | H | 4-Me |
| HN-CH$_2$-pyridine-CH$_2$OH | H | 4-F |
| HN-CH$_2$-furan | H | 4-F |
| HN-CH$_2$-thiazole | H | 4-F |
| HCCCH$_2$NH— | H | H |
| HO(CH$_2$)$_4$NH— | H | 4-F |
| HO(CH$_2$)$_5$NH— | H | 4-F |
| HO(CH$_2$)$_2$O(CH$_2$)$_2$NH— | H | 4-F |
| MeS(CH$_2$)$_3$NH— | H | H |
| HO(CH$_2$)$_3$NH— | H | H |
| HO(CH$_2$)$_5$NH— | H | H |
| HO(CH$_2$)$_2$O(CH$_2$)$_2$NH— | H | H |
| 2-FPy-4-ylCH$_2$NH— | 4-MeO | 4-F |
| 2-FPy-4-ylCH$_2$NH— | 4-Cl | 4-F |
| 2-FPy-4-ylCH$_2$NH— | H | 4-Cl |
| 2-FPy-4-ylCH$_2$NH— | H | 4-F |

TABLE 1-continued

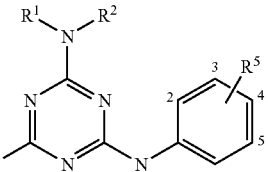

(The numbers 2 to 6 in the formula above represent respective bonding positions of R3 and R5.)

| $R^1\underset{N}{\diagdown}R^2$ | R³ | R⁵ |
|---|---|---|
| HN—CH₂-furan | 4-F | 4-F |
| HN—CH₂-(γ-butyrolactone) | H | H |
| HN—CH₂-tetrahydrofuran | H | H |
| HN—CH₂-thiazole | H | 4-F |

(Symbols in the table are as follows. Ph; phenyl, Py; pyridine, Bzl; benzyl)

A further embodiment of the invention is a method for treating dementia, which comprises administering the aforementioned BEC 1 inhibitor to a patient.

A still further embodiment is a method for preparing a medicament, particularly a pharmaceutical composition for dementia treatment use, which comprises a compound obtained by a screening method in which a compound to be tested is allowed to contact with BEC 1 potassium channel-expressed cells to identify if it inhibits said channel activity.

The symbols used hereinafter have the same meanings.

The following further describes the compound represented by the general formula (I) or (II). Unless otherwise noted, the term "lower" as used in the definition of the general formula of this specification means a straight or branched carbon chain having from 1 to 6 carbon atoms.

As the "halogen", fluorine, chlorine, bromine or iodine atom can be cited.

The "hydrocarbon radical" is a straight or branched chain hydrocarbon radical having from 1 to 15 carbon atoms, preferably from 1 to 10 carbon atoms, or a cyclic hydrocarbon radical having from 3 to 15 carbon atoms. The straight or branched chain hydrocarbon radical is an "alkyl", an "alkenyl" or an "alkynyl". Illustrative example of the "alkyl" is methyl, ethyl, isopropyl, hexyl, decyl, tetradecyl, pentadecyl or the like. The "alkenyl" is a hydrocarbon radical having at least one or more double bonds, such as vinyl, propenyl, allyl, isopropenyl, hexenyl or the like. The "alkynyl" is a hydrocarbon radical having at least one or more triple bonds, such as ethynyl, propynyl, butynyl or the like. The cyclic hydrocarbon radical is a "cycloalkyl", a "cycloalkenyl" or an "aryl". Illustrative example of the "cycloalkyl" is a monocyclic saturated ring such as cyclopropyl, cyclopentyl, cyclohexyl, cyclooctyl, cyclodecyl or the like. Said cycloalkyl may be bridged or condensed with benzene. For example, a $C_{3-10}$ cycloalkyl shown below is desirable. The "cycloalkenyl" is a hydrocarbon ring having one or more double bonds, and said cycloalkenyl may be condensed with a hetero ring, an aryl or a $C_{3-10}$ cycloalkyl. For example, a $C_{3-8}$ cycloalkenyl shown below is desirable. The "aryl" means an aromatic hydrocarbon radical including a $C_{6-14}$ aryl such as phenyl, naphthyl, anthryl or the like.

Said aryl may be condensed with a hetero ring, a $C_{3-10}$ cycloalkenyl, a $C_{3-10}$ cycloalkyl or a benzene-condensed cycloalkyl. For example, a di or tricyclic shown below is desirable.

Particularly, a di or tricyclic aryl condensed with benzene ring together with $R^3$, $R^4$ and the adjacent C, or $R^5$, $R^6$ and the adjacent C, may be substituted.

As said substituent group; oxo (=O), an aryl, an OH-aryl and a lower alkyl-O-aryl can be exemplified.

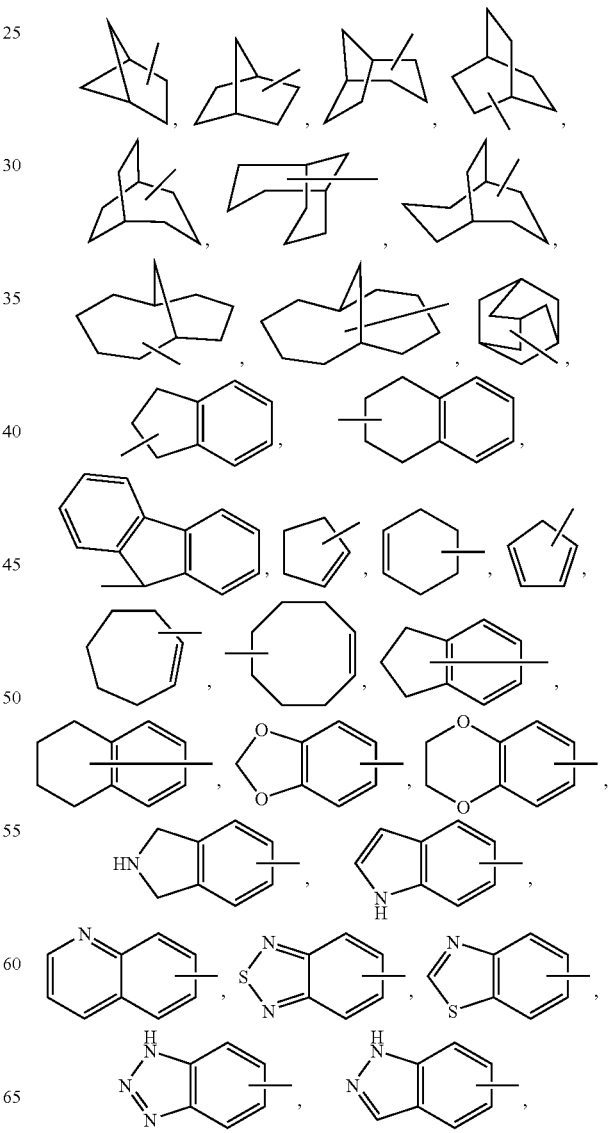

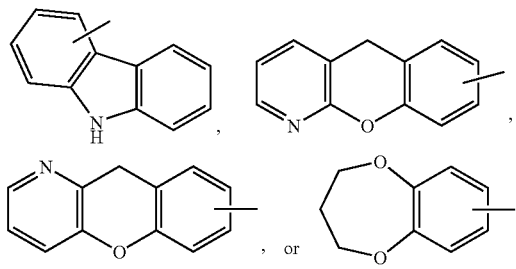
The "hetero ring" is a four- to seven-membered monocyclic, bicyclic or tricyclic aliphatic ring or aromatic ring containing from 1 to 4 hetero atoms selected from N, S and O. Said ring may be bridged or condensed with a $C_{3-10}$ cycloalkyl or a aryl. For example, the hetero rings shown in the following are preferred illustrative examples.
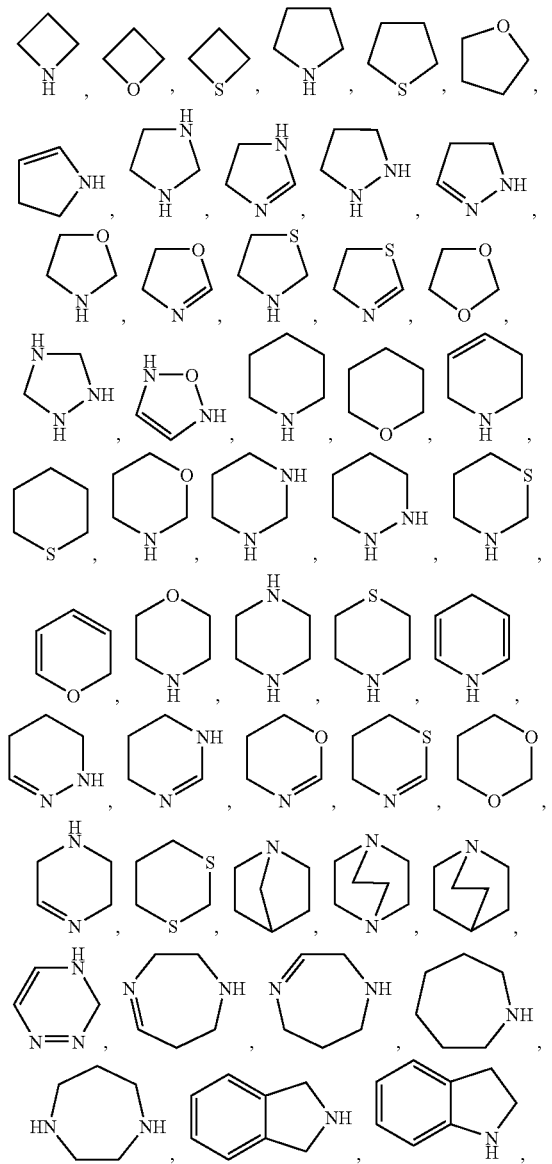
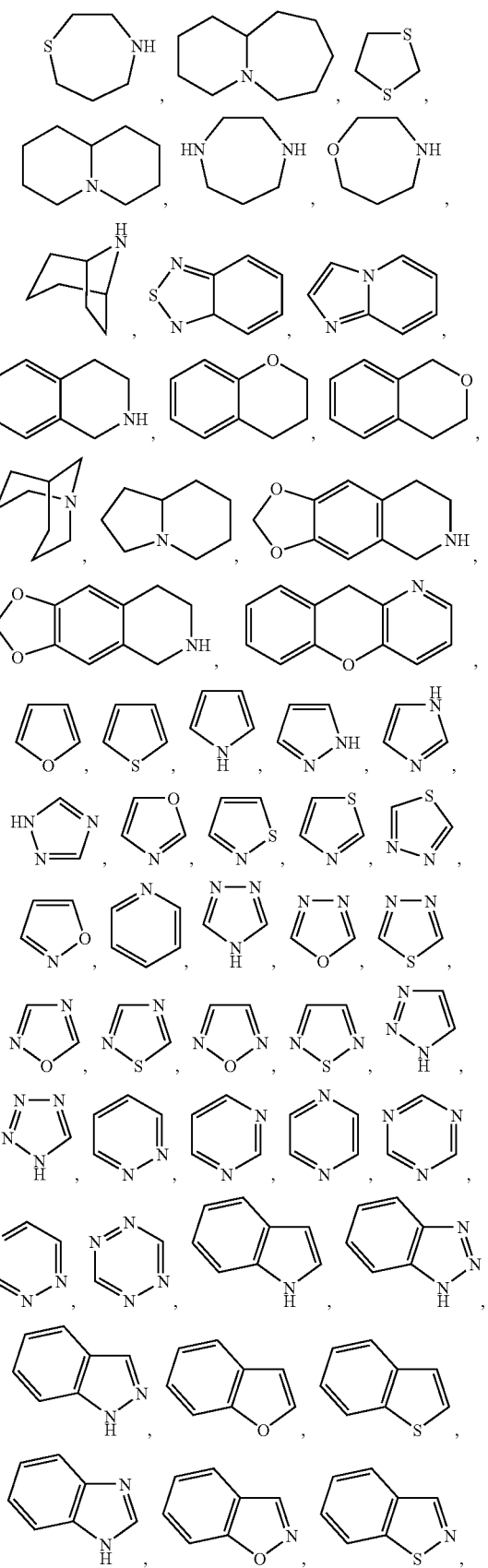

-continued

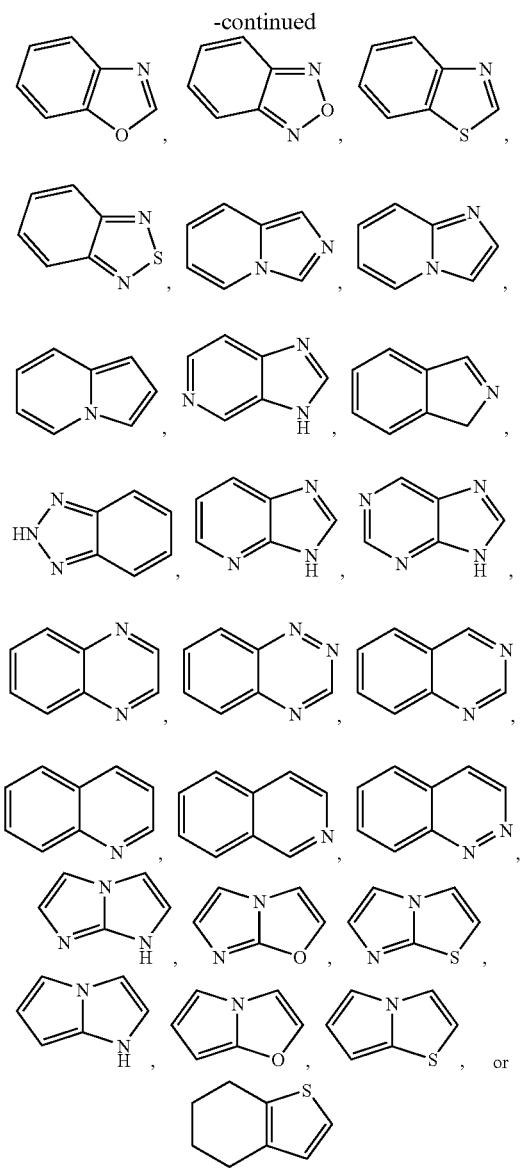

Regarding an aromatic nitrogen-containing hetero ring among the aforementioned hetero rings, a nitrogen atom on said ring may be quaternarized or form N-oxide.

The "nitrogen-containing hetero ring" is the aforementioned hetero ring having at least one nitrogen atom.

As the substituent group of the "hydrocarbon radical which may be substituted", substituent groups of the group a described in the following can preferably be exemplified.

As the substituent group of the "hetero ring which may be substituted" and "nitrogen-containing hetero ring which can be formed by $R^1$ and $R^2$ together with the adjacent N", substituent groups of the group a described in the following can preferably be exemplified.

Group a: (i) CN, (ii) $NO_2$, (iii) a halogen, (iv) $R^7R^8N$— ($R^7$ and $R^8$: the same or different from each other, and each represents (1) H, (2) a lower alkyl which may be substituted with an aryl or $R^9$—O—CO— ($R^9$: (1) H or a lower alkyl which may be substituted with an aryl), (3) an aryl which may be substituted with CN or a lower alkyl, (4) a hetero ring, (5) a lower alkyl-CO—, (6) a lower alkyl-O—CO—, (7) a cycloalkyl which may be substituted with HS— or a lower alkyl-S—, (8) an aryl-$SO_2$— which may be substituted with $NO_2$ or (9) a hetero ring-$SO_2$—), (v) $R^{10}$-T- ($R^{10}$: (1) H, (2) a lower alkyl which may be substituted with an aryl, an HO—$C_{1-10}$ alkylene-O— or HO or (3) an aryl, $T^1$: O or S), (vi) $R^{11}$-$T^2$- ($R^{11}$: (1) OH, (2) $R^7R^8N$—, (3) a lower alkyl-O—, (4) a lower alkyl, (5) an aryl or (6) a hetero ring ($T^2$: CO or $SO_2$)), (vii) a lower alkyl which may be substituted with a substituent group among the following (1) to (6) ((1) a halogen, (2) CN, (3) OH, (4) $R^{10}$CO—, (5) $R^7R^8N$— or (6) an aryl), (viii) a cycloalkyl which may be substituted with a lower alkyl, (ix) a cycloalkenyl, (x) a cycloalkynyl, (xi) an aryl which may be substituted with a substituent group among the following (1) to (5) ((1) a halogen, (2) $NO_2$, (3) $R^{12}$-$T^1$- ($R^{12}$: $R^{10}$ or a lower alkyl-aryl which may be substituted with OH, (4) $H_2NO_2S$— or (5) a lower alkyl which may be substituted with a halogen or OH), or (xii) a hetero ring which may be substituted with a substituent group among the following (1) to (9) ((1) a halogen, (2) oxo (=O), (3) $NO_2$, (4) a lower alkyl which may be substituted with [$R^7R^8N$—, $R^{10}$-$T^1$-, an aryl which may be substituted with (OH, a halogen or a lower alkyl-O—), (5) an aryl which may be substituted with a halogen, (6) OH, (7) a lower alkyl-O—, (8) $R^7R^8N$—, or (9) a hetero ring, The "BEC 1" and "BEC 1 potassium channel" mean the complete length protein represented by SEQ ID NO:2, or a fragment of said protein having the same function of said protein, or a fragment or complete length protein of said protein in which one or more amino acids may be substituted, deleted or inserted.

The "substance having BEC 1 potassium channel inhibitory action" can be obtained by subjecting compounds to be tested to a typical screening method such as the method described in U.S. Pat. No. 6,326,168.

a) Screening Method Which Uses Voltage-Clump Method

It is possible to measure channel activity of the BEC 1 potassium channel protein by the whole-cell voltage-clamp method. Cells expressing this channel protein are voltage-clamped and whole-cell current is recorded by the whole-cell voltage-clamp method. For example, a solution containing 145 mM NaCl, 5.4 mM KCl, 2 mM $CaCl_2$ and 0.8 mM $MgCl_2$ is used as the extracellular solution, and a solution containing 155 mM KCl is used as the intracellular solution (patch electrode solution). A compound and a peptide capable of modifying activity of the BEC 1 potassium channel protein can be screened by comparing outward currents generated by a depolarization stimulus, namely shifting a membrane potential from a holding potential (e.g., −70 mV) to a depolarization side (e.g., −80 mV), in the presence and absence of each drug to be tested.

b) Screening Method Which Uses Release of $Rb^+$ Ion

In general, the potassium channel can pass $Rb^+$ ion similar to $K^+$ ion, so that the channel activity can be measured using release of a radioisotope $^{86}Rb^+$ as a marker. By incubating cells expressing the novel potassium channel protein together with $^{86}RbCl$ (e.g., 18 hr, 37° C.), $^{86}Rb^+$ can be incorporated into the cells. The cells are washed with a low $K^+$ concentration physiological saline (e.g., 4.5 mM $K^+$) and then suspended in the same solution. When a high $K^+$ concentration solution (e.g., 100 mM in final concentration) is added to the cell suspension, membrane potential of the cell is depolarized and the potassium channel therefore is activated. As a result, the intracellular $^{86}Rb^+$ is released into the extracellular part, thus radioactivity of the extracellular solution can be used as a marker of the channel activity. It is possible to screen a compound and a peptide capable of modifying activity of the BEC 1 potassium channel protein, by comparing the radioactivity released into the extracellular part when the high $K^+$ concentration solution is added in the presence and absence of each drug to be tested.

c) Screening Method Which Uses a Voltage-Sensitive Dye or a Intracellular $K^+$-Detecting Dye It is possible that a voltage-sensitive dye or a intracellular $K^+$-detecting dye can optically detect a change in the potential or intracellular $K^+$ concentration accompanied by the opening of potassium channel. As the voltage-sensitive dye, RH 155, WW 781, Di-4-ANEPPS, derivatives thereof and the like can be used. In addition, a chimeric protein in which the amino acid sequence of green fluorescent protein is inserted into the C-terminal intracellular region of a Shaker type membrane voltage-dependent potassium channel can also be used in the detection of membrane potential (Siegel, M. S. and Isacoff, E. Y. (1997), *Neuron*, 19, 735-741). As the intracellular $K^+$-detecting dye, $K^+$-binding benzofuran isophthalate and the like can be used. By the use of these dyes, channel activity of the BEC 1 potassium channel can be measured and it is possible to screen a compound and a peptide capable of modifying activity of the BEC 1 potassium channel protein by comparing their changing amounts in the presence and absence of a drug to be tested.

Preferred screening method is a method for measuring BEC 1 inhibitory activity of a compound using $^{86}Rb$ ion releasing amount as the index, which is described later.

In addition, by allowing the Example 13 as a typical compound of the invention and a compound to be tested to undergo competitive BEC 1 potassium channel inhibition, a substance having said action can be obtained.

The compound to be tested may be illustratively any substance which has said inhibitory activity, and its examples include known compounds commercially available or registered in chemical file, a group of compounds obtained by combinatorial chemistry techniques, culture supernatants of microorganisms, natural components derived from plants and marine organisms, animal tissue extracts, antibodies and dominant negative proteins and the like. Also included are those in which said substances are modified with a substituent group or the like by a chemical conversion as a conventional method for those skilled in the art.

Depending on the type of groups, optical isomers (optically active substances, diastereomers and the like) are present in the compounds of the invention. Since compounds having amide bond and double bond are present in the compounds of the invention, tautomers based on the amide bond and geometrical isomers are also present. Separated or mixed forms of these isomers are included in the invention.

The compound of the invention forms a salt with an acid or a base. Examples of the salt with an acid include acid addition salts with inorganic acid such as hydrochloric acid, hydrobromic acid, hydroiodic acid, sulfuric acid, nitric acid, phosphoric acid and the like mineral acids, and with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like.

Examples of the salt with a base include salts with sodium, potassium, magnesium, calcium, aluminum and the like inorganic bases, methylamine, ethylamine, meglumine, ethanolamine and the like organic bases, or lysine, arginine, ornithine and the like basic amino acids, as well as an ammonium salt. Also, the compound of the invention can form a hydrate, solvates with ethanol and the like and polymorphism.

In addition, all of the compounds which are metabolized and converted in the living body, so-called prodrugs, are also included in the active ingredient of the invention or compound of the invention. Examples of the group which forms the prodrug of the invention include the groups described in *Prog. Med.*, 5, 2157-2161 (1985) and "Iyakuhin-no Kaihatsu (Development of Medicaments", Vol. 7 (Hirokawa Shoten, 1990), Bunshi Sekkei (Molecular Design), pp. 163-198.

(Production Methods)

The compound of the invention and a pharmaceutically acceptable salt thereof can be produced applying various conventionally known synthesis methods, making use of the characteristics based on its basic nucleus and kinds of substituent groups. For example, oxidation, reduction, amination, alkylation, amidation, sulfonamidation, esterification, urea formation and the like reactions can be carried out by referring to the conditions described in references such as "Jikken Kagaku Koza (Experimental Chemistry Series)" 4th edition, edited by The Chemical Society of Japan (1991) (published by Maruzen). In that case, depending on the kinds of functional groups, it is sometimes effective in view of production techniques to replace said functional groups by appropriate protecting groups (groups which can be easily converted into said functional groups) at the stage of the material or an intermediate. Examples of such functional groups include amino group, OH (hydroxyl group), COOH (carboxy) and the like, and examples of their protecting groups include the protecting groups described in "Protective Groups in Organic Synthesis (3rd edition)" edited by Greene and Wuts, which may be optionally selected in response to the reaction conditions. In such a method, the compound of interest can be obtained by eliminating the protecting group as occasion demands after carrying out the reaction by introducing said protecting group.

Materials of the compounds of the invention and production methods of the compounds of the invention are described in detail in the following. Though the compounds of the invention can be produced by conventionally known methods, such as the methods described in *Bull. Soc. Chim. Fr.*, 6, 2112 (1973) and the like, or modified methods thereof, typical production methods are shown in the following.

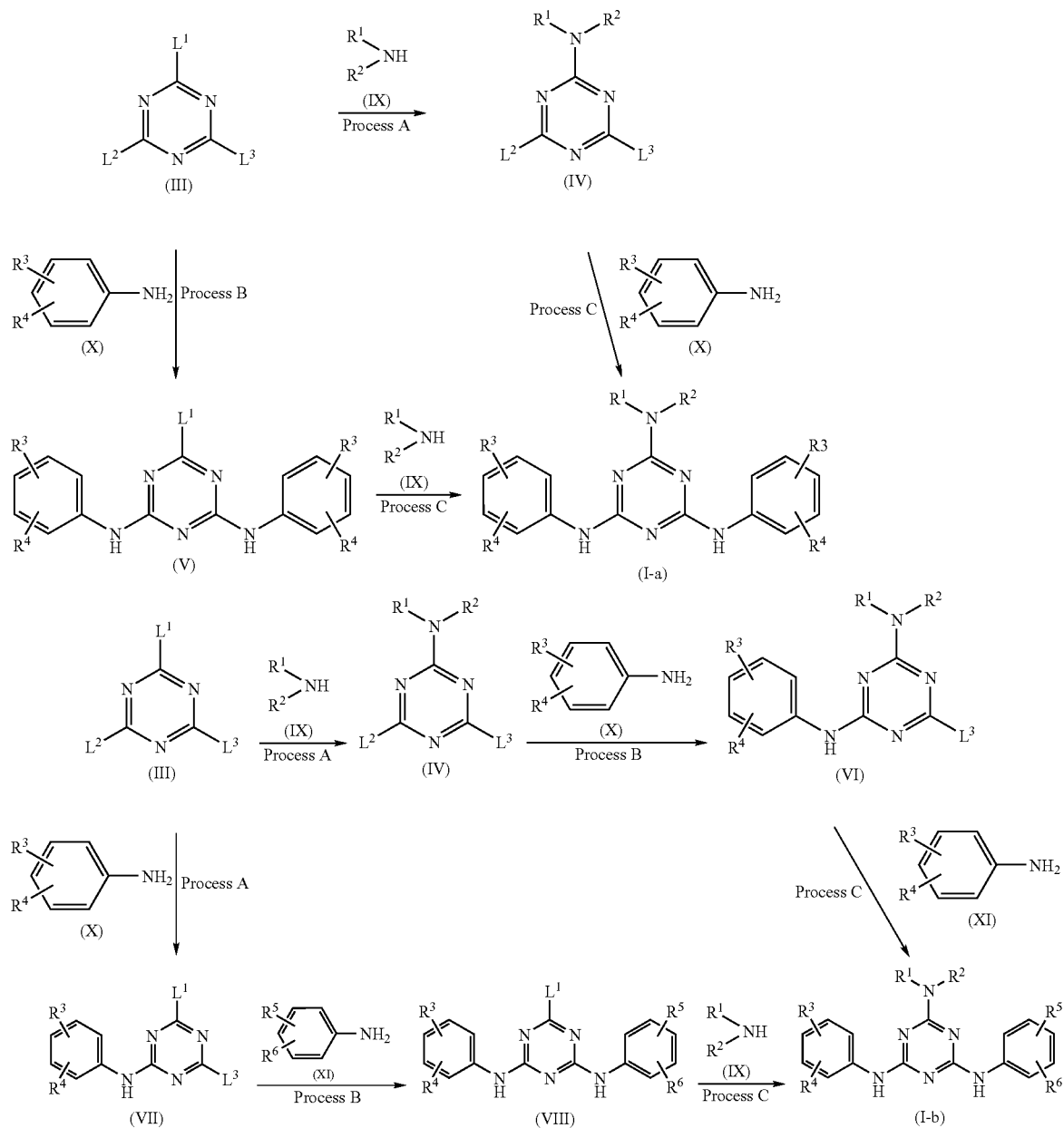

(In the formulae, $L^1$, $L^2$ and $L^3$ indicate leaving groups.)

As the leaving group, (i) a halogen, (ii) methylsulfanyl, (iii) methylsulfinyl, (iv) a $C_{1-6}$ alkanesulfonyloxy group which may be substituted with 1 to 3 halogen (e.g., methanesulfonyloxy, trifluoromethanesulfonyloxy or the like), or (v) a $C_{6-10}$ allenesulfonyloxy group which may be substituted with 1 to 4 $C_{1-6}$ alkyl or halogen (e.g., p-toluenesulfonyloxy, p-bromobenzenesufonyloxy or the like) can be exemplified.

Process A

The material compound (IV) or (VII) of the compound of the invention can be synthesized by conventionally known methods described in *Agric. Biol. Chem.*, 51, 9, 2563 (1989) and *J. Am. Chem. Soc.*, 116, 4326 (1994) or modified methods thereof.

Process B

The material compound (V), (VI) or (VIII) of the compound of the invention can be synthesized by conventionally known methods described in *J. Am. Chem. Soc.*, 116, 2382 (1994), U.S. Pat. No. 2,476,548, *J. Chem. Soc.*, 561 (1948) and *Yuki Gosei Kagaku Kyokai-shi* (Journal of the Society of Synthetic Organic Chemistry), vol. 18, p. 332 (1960) or modified methods thereof.

Process C

This Process is a method in which the compound (1-a) or (1-b) of the invention is obtained by allowing a compound (IV), (V), (VI) or (VIII) to react with an amine compound (IX) or an aniline compound (X) or (XI). The reaction is carried out under cooling to heating reflux using the compound (IV), (V), (VI) or (VIII) and the compound (IX), (X)

or (XI) at an equivalent molar ratio, or one of them in an excess amount, without a solvent or in a solvent inert to the reaction such as benzene, toluene, xylene or the like aromatic hydrocarbon, diethyl ether, tetrahydrofuran (THF), dioxane or the like ether, dichloromethane, 1,2-dichloroethane, chloroform or the like halogenated hydrocarbon, N,N-dimethylformamide (DMF), N,N-dimethylacetamide (DMA), N-methylpyrrolidone, ethyl acetate or acetonitrile. The reaction temperature can be optionally set in response to the compounds. Depending on the compounds, it is desirable in some cases to carry out the reaction in the presence of an organic base (preferably diisopropylethylamine, N-methylmorpholine, pyridine or 4-(N,N-dimethylamino)pyridine) or a metal salt base (preferably sodium hydride, potassium carbonate, sodium carbonate, sodium bicarbonate, sodium hydroxide or potassium hydroxide). In addition, depending on the compounds, it is advantageous in some cases to carry out the reaction in the absence of a base, for effecting smooth reaction.

The compound (I) of the invention can be isolated and purified by conventionally known techniques such as solvent extraction, liquid conversion, solvent partition, crystallization, recrystallization, chromatography and the like. In addition, material compound of the compound (III), (IV), (V), (VI), (VII) or (VIII) or a pharmaceutically acceptable salt thereof can be isolated and purified by the same conventionally known techniques as described in the above, but it may be directly used as the material of the subsequent step as a reaction mixture without isolation.

In this connection, the aforementioned Processes are not limited to the substituent groups in the formulae and can be broadly applied to cases in which the compounds of the invention have similar substituent groups.

The compound of the invention produced in such a manner is isolated and purified in its free form or as a pharmaceutically acceptable salt thereof.

The isolation and purification are carried out by employing usual chemical operations such as extraction, concentration, evaporation, crystallization, filtration, recrystallization, various types of chromatography and the like.

Various isomers can be separated by selecting an appropriate material compound or making use of the difference in physical property between isomers. For example, optical isomers can be made into a stereochemically pure isomer by selecting an appropriate material or by subjecting to optical resolution of racemic compound (e.g., a method in which optical resolution is carried out after converting into diastereomer salts with a general optically active base).

INDUSTRIAL APPLICABILITY

The invention relates to an anti-dementia agent which uses a BEC 1 potassium channel inhibitor as the active ingredient.

When a transgenic mouse in which the BEC 1 potassium channel is frequently expressed in the hippocampus and cerebral cortex was prepared and its behavior was analyzed, it was revealed that learning performance of said mouse was reduced in a Morris water maze learning test, a passive avoidance task and a fear conditioning, which are described later. In addition, immunohistochemical detection of the BEC 1 potassium channel using the brain of Alzheimer patients suggested that its expression is increased in nerve cells of the hippocampus and cerebral cortex. The above results suggest a possibility that increase in the expression of the BEC 1 potassium channel in the hippocampus and cerebral cortex of the Alzheimer patient is inhibiting a memory and learning-related neural transmission by reducing excitability of nerve cells.

As a result of further conducting intensive studies, it was confirmed that a BEC 1 potassium channel inhibitor, or a compound shown in Invention Example 744 as a typical compound, has an action to improve an amnesia induced by electroconvulsive shock (ECS) in a mouse passive avoidance task.

Based on the above, it was verified that the BEC 1 potassium channel inhibitor has an action to improve learning disorder and is useful as a preventive or therapeutic agent for a disease in which the BEC 1 potassium channel is considered to be concerned, preferably dementia.

The pharmaceutical composition which contains one or two or more of the BEC 1 potassium channel inhibitors or pharmaceutically acceptable salts thereof as the active ingredient is prepared using generally used pharmaceutical carriers, fillers and other additives.

The pharmaceutical carriers and fillers may be either in solid or liquid forms, and their examples include lactose, magnesium stearate, starch, talc, gelatin, agar, pectin, gum arabic, olive oil, sesame oil, cacao butter, ethylene glycol and the like and other generally used substances.

The administration may be effected in the form of either oral administration by tablets, pills, capsules, granules, powders, solutions or the like or parenteral administration by injections for intravenous injection, intramuscular injection or the like, suppositories, percutaneous preparations and the like.

The dose is optionally decided in response to each case by taking into consideration symptoms and age, sex and the like of each patient to be treated, but is usually within the range of from 1 to 1,000 mg, preferably from 50 to 200 mg, per adult per day by oral administration, or dividing the daily dose into several doses per day, or from 1 to 500 mg by parenteral administration, per day per adult, by dividing the daily dose into 1 to several doses per day, or within the range of from 1 hour to 24 hours per day by intravenous-continued administration. Since the dose varies under various conditions as described in the foregoing, a smaller dose than the aforementioned range may be sufficient enough in some cases.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium silicate. In the usual way, the composition may contain other additives than the inert diluent, such as magnesium stearate or the like lubricant, calcium cellulose glycolate or the like disintegrating agent, lactose or the like stabilizing agent and glutamic acid, aspartic acid or the like solubilization assisting agent.

If necessary, tablets or pills may be coated with a sugar coat or a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethyl alcohol. In addition to the inert diluent, this composition may also contain a moistening agent, a suspending agent and the like auxiliary agents, as well as sweeteners, flavors, aromatics and antiseptics.

The injections for parenteral administration includes aseptic aqueous or non-aqueous solutions, suspensions and emulsions. Examples of the diluent for use in the aqueous solutions and suspensions include distilled water for injection and physiological saline. Examples of the diluent for use in the non-aqueous solutions and suspensions include propylene glycol, polyethylene glycol, olive oil or the like plant oil, ethanol or the like alcohol, polysorbate 80 and the like. Such a composition may further contain additive agents such as an antiseptic, a moistening agent, an emulsifying agent, a dispersing agent, a stabilizing agent (e.g., lactose) and a solubilization assisting agent (e.g., glutamic acid or aspartic acid). These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

BEST MODE FOR CARRYING OUT THE INVENTION

EXAMPLES

Next, the invention is described further in detail based on examples, but the invention is not limited to these examples. In this connection, production methods for the starting compounds to be used in the Invention Examples are described as Reference Examples.

Unless otherwise noted, the term % as used in the following means percent by weight. Other abbreviations as used herein means as follows.

Symbols in the tables are as follows.

Ex: Invention Example Number

Ref: Reference Example Number

F: fluoro, Cl: chloro, $NO_2$: nitro, OH: hydroxy, CN: cyano, Me: methyl, Et: ethyl, Ph: phenyl, Py: pyridine, Py-2-ylCH$_2$NH: pyridin-2-ylmethylamino, Py-3-ylCH$_2$NH: pyridin-3-ylmethylamino, Py-4-ylCH$_2$NH: pyridin-4-ylmethylamino, $CF_3$: trifluoromethyl, iPr: isopropyl, Pen: pentyl, cPr: cyclopropyl, cHex: cyclohexyl, Bzl: benzyl, Bz: benzoyl, diMePhNH: dimethylphenylamino, diMeOPhNH: dimethoxyphenylamino, diClPhNH: dichlorophenylamino, diCF$_3$PhNH: ditrifluoromethylphenylamino, Ac: acetyl, AcOEt: ethyl acetate, free: free form, NMR: nuclear magnetic resonance spectrum (measured with tetramesylsilane (TMS) internal standard (indicated by ppm))

The $^1$H-NMR spectrum is expressed by chemical shift value when TMS is used as the internal standard, and the signals are indicated by the following abbreviations. s: singlet, d: doublet, t: triplet, q: quartet, br: broad, m: multiplet, m.p.: melting point [° C.] (Melting point was measured using a melting point measuring apparatus Yanako MP-S3 manufactured by Yanagimoto and shown by uncorrected value.)

MS: FAB-MS, MASS: ESI-MS, HPLC rt: HPLC retention time

Measuring apparatus: HPLC: 2790 separation module manufactured by WATERS; MS: ZMD manufactured by Micromass PDA detector: A 996 photodiode array detector manufactured by WATERS Measuring conditions: Column, WAKOSIL-2 5C18AR, 2.0 mm I.D.×30 mm Column temperature: 35° C.

Mobile phase solution A=5 mM trifluoroacetic acid aqueous solution, solution B=methanol Detection wavelength: 254 nm or 210 nm Sample input: 5 μl Flow rate: 1.2 ml/min In this connection, regarding mixing ratio of the mobile phase, the initial stage solvent condition was used as a 10% mobile phase B and increased thereafter to a 100% mobile phase B with linear gradient spending 4 minutes, and the subsequent 0.5 minute was used as a 100% mobile phase B.

Material compounds are shown in Reference Examples.

Reference Example 1

A 2.41 g portion of 2,4-dichloro-6-anilino-1,3,5-triazine was dissolved in 20 ml of acetonitrile, and 2.09 ml of diisopropylethylamine and 1.23 g of p-fluoroaniline were added thereto and stirred overnight at room temperature. The reaction solution was mixed with water and extracted with ethyl acetate, and the organic layer was washed with 1 M hydrochloric acid and saturated brine and then dried using anhydrous magnesium sulfate.

The solvent was evaporated under a reduced pressure, the thus obtained residue was applied to a silica gel column chromatography and eluted with ethyl acetate:n-hexane (1:9), and then the thus obtained crude product was crystallized from benzene, thereby obtaining 2.25 g of 6-chloro-N-(4-fluorophenyl)-N'-phenyl-1,3,5-triazine-2,4-diamine as a white solid.

The compounds of Reference Examples 2 to 5 shown in the following Table 4 were synthesized in the same manner as in Reference Example 1.

Reference Example 6

A 2.59 g portion of 4,6-dichloro-N-(4-fluorophenyl)-1,3,5-triazine was dissolved in 20 ml of acetonitrile, and 2.09 ml of diisopropylethylamine and 1.18 g of p-toluidine were added thereto and stirred overnight at room temperature. The reaction solution was mixed with water and extracted with ethyl acetate, and the organic layer was washed with 1 M hydrochloric acid and saturated brine and then dried using anhydrous magnesium sulfate. The solvent was evaporated under a reduced pressure, the thus obtained residue was applied to a silica gel column chromatography and eluted with ethyl acetate:n-hexane (1:9), and then the thus obtained crude product was crystallized from benzene, thereby obtaining 2.74 g of 6-chloro-N-(4-fluorophenyl)-N'-(4-methylphenyl)-1,3,5-triazine-2,4-diamine as a white solid.

The compounds of Reference Examples 7 to 12 shown in the following Table 4 were synthesized in the same manner as in Reference Example 6.

Invention Example 1

A 200 mg portion of 6-chloro-N,N'-diphenyl-1,3,5-triazine-2,4-diamine was dissolved in 10.0 ml of acetonitrile, and 145 mg of 4-(aminomethyl)pyridine and 0.585 ml of diisopropylethylamine were added thereto and stirred overnight at 80° C. The reaction solution was cooled down to room temperature, and then mixed with water and extracted with chloroform. The organic layer was washed with 5% citric acid and saturated brine and then dried using anhydrous magnesium sulfate. The solvent was evaporated under a reduced pressure, the thus obtained residue was applied to a silica gel column chromatography and eluted with ethyl acetate:n-hexane (2:1), and then the thus obtained crude product was crystallized from ethyl acetate/n-hexane, thereby obtaining 107 mg of N,N'-diphenyl-N''-(4-pyridylmethyl)-1,3,5-triazine-2,4,6-triamine as light red crystals.

The compounds of Invention Examples 2 to 38 and compounds of Invention Examples 740 to 815 shown in the following Tables 5 to 7 and the following Tables 28 to 35 were synthesized in the same manner as in Invention Example 1.

Invention Example 39

A 207 mg portion of (4,6-dichloro-1,3,5-triazin-2-yl)isopropylamine was dissolved in 10.0 ml of acetonitrile, and 369 mg of 4-methoxyaniline was added thereto and stirred at 80° C. for 3 days. The reaction solution was cooled down to room temperature, and then mixed with water and extracted with ethyl acetate. The organic layer was washed with 1 M hydrochloric acid aqueous solution and saturated brine and then dried using anhydrous magnesium sulfate. The solvent was evaporated under a reduced pressure, and the thus obtained residue was applied to a silica gel column chromatography and eluted with ethyl acetate:n-hexane (2:1) to obtain a clued product. This crude product was dissolved in ethyl acetate and mixed with 4 M hydrochloric acid ethyl acetate solution, the solvent was evaporated under a reduced pressure, and the thus obtained residue was crystallized from ethyl acetate, thereby obtaining 332 mg of N-isopropyl-N',N"-bis(4-methoxyphenyl)-1,3,5-triazine-1,3,5-triamine hydrochloride as colorless crystals.

The compounds of Invention Examples 40 to 44 shown in the following Table 7 were synthesized in the same manner as in Invention Example 39.

Invention Example 45

A 316 mg portion of the 6-chloro-N-(4-fluorophenyl)-N'-phenyl-1,3,5-triazine-2,4-diamine was dissolved in 10.0 ml of acetonitrile, and 0.523 ml of diisopropylethylamine and 0.170 ml of isopropylamine were added thereto and stirred overnight at 80° C. The reaction solution was cooled down to room temperature, and then mixed with water and extracted with ethyl acetate. The organic layer was washed with 5% citric acid aqueous solution and saturated brine and then dried using anhydrous magnesium sulfate. The solvent was evaporated under a reduced pressure, and the thus obtained residue was applied to a silica gel column chromatography and eluted with ethyl acetate:n-hexane (2:1) to obtain a crude product. This crude product was dissolved in ethyl acetate and mixed with 4 M hydrochloric acid ethyl acetate solution, the solvent was evaporated under a reduced pressure, and the thus obtained residue was crystallized from ethyl acetate, thereby obtaining 327 mg of N-(4-fluorophenyl)-N'-isopropyl-N"-phenyl-1,3,5-triazine-2,4,6-triamine hydrochloride as colorless crystals.

The compounds of Invention Examples 46 to 50 shown in the following Table 8 were synthesized in the same manner as in Invention Example 45.

Invention Example 51

(A Synthesis Example by Combinatorial Chemistry)

A 7.5 mg (60 μmol) portion of p-fluorobenzylamine and 52 μl of diisopropylethylamine were added to a mixed solution of 400 μl of acetonitrile and 120 μl of N-methylpyrrolidone containing 8.9 mg (30 μmol) of 6-chloro-N,N'-diphenyl-1,3,5-triazine-2,4-diamine and stirred at 80° C. for 3 hours. The reaction solution was filtered and then injected into a fractional LC-MS apparatus to collect a fraction containing the desired molecular weight. By evaporating the solvent, 6.1 mg (yield 45%) of N,N'-diphenyl-N"-(4-fluorobenzyl)-1,3,5-triazine-2,4,6-triamine was obtained. A retention time of 2.77 minutes and a purity of 93% were determined by an analytical LC-MS.

The compounds of Invention Examples 52 to 418 shown in the following Tables 9 to 18 were synthesized in the same manner as in Invention Example 51.

Invention Example 419

A 6.7 mg (60 μmol) portion of 2-fluoroaniline was added to a mixed solution of 400 μl of acetonitrile and 120 μl of N-methylpyrrolidone containing 8.9 mg (30 μmol) of 6-chloro-N,N'-diphenyl-1,3,5-triazine-2,4-diamine and stirred at 80° C. for 3 hours. The reaction solution was filtered and then injected into a fractional LC-MS apparatus to collect a fraction containing the desired molecular weight.

By evaporating the solvent, 6.0 mg (yield 54%) of N,N'-diphenyl-N"-(2-fluorophenyl)-1,3,5-triazine-2,4,6-triamine was obtained. A retention time of 3.01 minutes and a purity of 94% were determined by an analytical LC-MS.

The compounds of Invention Examples 420 to 583 shown in the following Tables 19 to 22 were synthesized in the same manner as in Invention Example 419.

Invention Example 584

A 10 mg portion of 2,6-dichloro-N-isopropyl-1,3,5-triazine-4-amine was dissolved in 600 μl of N-methyl-2-pyrrolidone, and 400 μl of 0.5 mM 2-fluoroaniline N,N-dimethylformamide solution and 26 μl of diisopropylethylamine were added thereto and stirred at 120° C. for 3 days. The reaction solution was mixed with 50 mg (4.27 mmol/g) of PS-trisamine manufactured by Algonote and further stirred at 120° C. for 7 hours. After cooling down to 50° C., the reaction solution was mixed with 50 mg (1.53 mmol/g) of PS-benzaldehyde manufactured by Algonote and further stirred at 50° C. for 16 hours. The reaction solution was cooled down to room temperature and then mixed with saturated sodium bicarbonate aqueous solution and chloroform and stirred. After filtration of the solution, the organic layer was dried using anhydrous sodium sulfate, and then the solvent was evaporated under a reduced pressure to obtain 7 mg of N,N'-di-(2-fluorophenyl)-N"-isopropyl-1,3,5-triazine-2,4,6-triamine as a brown resinous substance.

The compounds of Invention Examples 585 to 636 shown in the following Tables 23 and 24 were synthesized in the same manner as in Invention Example 584.

Invention Example 637

A 14 mg portion of 6-chloro-N-isopropyl-N'-phenyl-1,3,5-triazine-2,4-diamine was dissolved in 800 μl of N-methyl-2-pyrrolidone, and 200 μl of 0.5 mM 2-fluoroaniline N,N-dimethylformamide solution and 50 μl of 4 M hydrochloric acid/dioxane were added thereto and stirred at 80° C. for 7 hours. After cooling down the reaction solution to 60° C., 50 mg (4.27 mmol/g) of PS-trisamine and 50 mg (1.53 mmol/g) of PS-benzaldehyde both manufactured by Algonote were added to the reaction solution and further stirred at 60° C. for 16 hours. The reaction solution was cooled down to room temperature and then mixed with saturated sodium bicarbonate aqueous solution and chloroform and stirred. After filtration of the solution, the organic layer was dried using anhydrous sodium sulfate, and then the solvent was evaporated under a reduced pressure to obtain 13 mg of N-(2- fluorophenyl)-N'-isopropyl-N"-phenyl-1,3,5-triazine-2,4,6-triamine as a brown resinous substance.

The compounds of Invention Examples 638 to 739 shown in the following Tables 24 to 27 were synthesized in the same manner as in Invention Example 637.

Invention Example 816

A 565 mg portion of the N-(4-fluorophenyl)-N'-[(6-methoxypyridin-3-yl)methyl]-N"-phenyl-1,3,5-triazine-2,4,6-triamine hydrochloride synthesized in Invention Example 753 was mixed with 5 ml of 25% hydrobromic acid acetic acid solution and 1 ml of 48% hydrobromic acid aqueous solution and stirred at 80° C. for 6 hours. After evaporation of the reaction solution under a reduced pressure, the residue was mixed with ethyl acetate and sodium bicarbonate aqueous solution in that order and extracted with ethyl acetate. The organic layer was washed with saturated brine and dried using anhydrous magnesium sulfate. The solvent was evaporated under a reduced pressure, and the thus obtained residue was applied to a silica gel column chromatography and eluted with chloroform:methanol (99:1) to obtain a crude product. This crude product was dissolved in ethyl acetate and mixed with 4 M hydrochloric acid ethyl acetate solution, and the thus formed crystals were collected by filtration and dried to obtain 195 mg of 5-[({4-anilino-6-[(4-fluorophenyl)amino]-1,3,5-triazin-2-yl}amino)methyl]pyridine-2(1H)-one hydrochloride as colorless crystals.

The compounds of Invention Examples 817 and 818 shown in the following Table 35 were synthesized in the same manner as in Invention Example 816.

Invention Example 819

A 250 mg portion of the tert-butyl {6-[({4-anilino-6-[(4-fluorophenyl)amino]-1,3,5-triazin-2-yl}-)amino]methyl}pyridin-2-yl}carbamate hydrochloride synthesized in Invention Example 758 was dissolved in 10.0 ml of ethyl acetate, and 10.0 ml of 4 M hydrochloric acid ethyl acetate solution was added thereto and stirred at room temperature for 4 hours. The thus formed pale yellow crystals were collected by filtration and dried to obtain 190 mg of N-[(6-aminopyridin-2-yl)methyl]-N'-(4-fluorophenyl)-N"-phenyl-1,3,5-triazine-2,4,6-triamine hydrochloride as pale yellow crystals.

Invention Example 820

A 360 mg portion of the N-(4-fluorophenyl)-N'-{[1-(4-methoxybenzyl)-1H-1,2,4-triazol-5-yl]methyl}-N"-phenyl-1,3,5-triazine-2,4,6-triamine hydrochloride synthesized in Invention Example 767 was dissolved in 5 ml of trifluoroacetic acid and stirred at 70° C. overnight. After evaporation of the reaction solution under a reduced pressure, the residue was mixed with ethyl acetate and sodium bicarbonate aqueous solution in that order and extracted with ethyl acetate. The organic layer was washed with saturated brine and dried using anhydrous magnesium sulfate. The solvent was evaporated under a reduced pressure, and the thus obtained residue was applied to a silica gel column chromatography and eluted with chloroform:methanol (92.8) to obtain a crude product. This crude product was dissolved in ethyl acetate and mixed with 4 M hydrochloric acid ethyl acetate solution, and the thus formed crystals were collected by filtration and dried to obtain 268 mg of N-(4-fluorophenyl)-N'-phenyl-N"-(1H-1,2,4-triazol-3-yl)-1,3,5-triazine-2,4,6-triamine hydrochloride as colorless crystals.

Invention Example 821

A 678 mg portion of [(1-trityl-1H-imidazol-4-yl)methyl]amine was dissolved in 10.0 ml of acetonitrile, and 0.52 ml of diisopropylethylamine and 316 mg of the 6-chloro-N-(4-fluorophenyl)-N'-phenyl-1,3,5-triazine-2,4-diamine synthesized in Reference Example 1 were added thereto and stirred at 80° C. for 3 days. After cooling down to room temperature, the reaction solution was mixed with water and extracted with ethyl acetate. The organic layer was washed with citric acid aqueous solution and saturated brine and dried using anhydrous magnesium sulfate. The solvent was evaporated under a reduced pressure, and the thus obtained residue was applied to a silica gel column chromatography and eluted with chloroform:methanol (99:1) to obtain a crude product. This crude product was dissolved in 9 ml of acetic acid and 1 ml of water and stirred at 70° C. for 2 hours. After evaporation of the reaction solution under a reduced pressure, the residue was mixed with ethyl acetate and sodium bicarbonate aqueous solution in that order and extracted with ethyl acetate. The organic layer was washed with saturated brine and dried using anhydrous magnesium sulfate. The solvent was evaporated under a reduced pressure, and the thus obtained residue was applied to a silica gel column chromatography and eluted with chloroform:methanol (90:10) to obtain a crude product. This crued product was dissolved in ethyl acetate and mixed with 4 M hydrochloric acid ethyl acetate solution, and the thus formed crystals were collected by filtration and dried to obtain 306 mg of N-(4-fluorophenyl)-N'-(1H-imidazol-4-ylmethyl)-N"-phenyl-1,3,5-triazine-2,4,6-triamine hydrochloride as colorless crystals.

In the following, structures and physical property values of the compounds of Reference Examples and Invention Examples are shown in Tables 4 to 35.

In addition, the compounds shown in the following Tables 36 to 39 can also be synthesized in the same manner as in the aforementioned Invention Examples. The sign "No" in the tables indicates compound number.

Invention Example 822

(Test Method)
Method for Measuring BEC 1 Inhibitory Activity of Compounds Using Released Amount of $^{86}$Rb ions as the Index The channel activity of BEC 1 was measured in accordance with the method described in WO 99/37677, using amount of a radioisotope $^{86}$Rb ion released from a BEC 1-expressing cell as the index. That is, when an $^{86}$Rb ion-incorporated BEC 1-expressing cell was stimulated with 100 mM KCl, the radioactivity released from the cell was used as the channel activity of BEC 1. The $^{86}$Rb ions were incorporated into a BEC 1-stably expressing cell by culturing the cell (3 hours, 37° C.) in the presence of $^{86}$RbCl (0.5 µCi/ml), and the un-incorporated $^{86}$Rb ions were removed by washing three times with HEPES-buffered saline (pH 7.4, 2.5 mM KCl). The cells were incubated with HEPES-buffered saline containing a compound to be tested at room temperature for 15 minutes and then further incubated with 100 mM KCl-containing HEPES-buffered saline (pH 7.4) containing the compound to be tested at room temperature for 5 minutes. The extracellular medium was recovered, and then the remaining cells were lysed with 0.1 N NaOH and recovered.

The Cerenkov radioactivity of the extracellular medium and cell lysate was respectively measured, and their total was used as the total radioactivity. The released amount of $^{86}$Rb ions was expressed by the percentage of extracellular medium radioactivity based on the total radioactivity. The value obtained in the presence of the compound was used as a test value, and the value obtained in the absence of the compound as a control value and the value obtained when not stimulated with 100 mM KCl as a blank value. Inhibitory action of each compound was expressed by % inhibition, namely (control value−test value)×100/(control value−blank value), or by an IC$_{50}$ value calculated from the % inhibition. As the test results of typical compounds are shown in the following Tables 2 and 3, it was confirmed that said compounds have the BEC 1 potassium channel inhibitory action.

In this connection, as the BEC 1-expressing cell, a BEC 1-stably expressing cell prepared in accordance with the method described in WO 99/37677 using a dihydrofolate reductase (dhfr)-deficient strain of a Chinese hamster ovary cell was used.

TABLE 2

Test results

| Ex | BEC1 IC$_{50}$(μM) |
|---|---|
| 1 | 0.084 |
| 4 | 0.079 |
| 7 | 0.39 |
| 8 | 0.29 |
| 9 | 0.052 |
| 11 | 0.43 |
| 12 | 0.29 |
| 13 | 0.18 |
| 14 | 0.39 |
| 16 | 0.36 |
| 17 | 0.29 |
| 18 | 1.1 |
| 19 | 1.3 |
| 20 | 0.32 |
| 21 | 0.59 |
| 22 | 0.19 |
| 23 | 0.24 |
| 24 | 0.48 |
| 32 | 0.24 |
| 33 | 0.97 |
| 35 | 0.24 |
| 25 | 0.11 |
| 28 | 0.39 |
| 29 | 0.35 |
| 30 | 0.073 |
| 31 | 0.49 |
| 36 | 0.48 |
| 37 | 0.26 |
| 38 | 0.18 |
| 39 | 0.66 |
| 40 | 0.63 |
| 41 | 0.40 |
| 45 | 0.22 |
| 46 | 0.49 |
| 47 | 0.72 |
| 48 | 0.29 |
| 49 | 0.14 |
| 50 | 0.49 |
| 740 | 4.9 |
| 741 | 0.52 |
| 742 | 1.4 |
| 743 | 0.10 |
| 744 | 0.085 |
| 747 | 3.6 |
| 764 | 0.047 |
| 771 | 0.25 |
| 773 | 1.5 |
| 774 | 0.55 |
| 775 | 0.11 |
| 776 | 0.14 |
| 777 | 0.21 |

TABLE 2-continued

Test results

| Ex | BEC1 IC$_{50}$(μM) |
|---|---|
| 778 | 0.45 |
| 779 | 0.70 |
| 780 | 0.34 |
| 789 | 9.5 |
| 790 | 4.7 |
| 791 | 2.2 |
| 794 | 3.1 |
| 795 | 0.24 |
| 796 | 0.17 |
| 797 | 0.65 |
| 801 | 0.25 |
| 808 | 0.42 |
| 819 | 1.4 |

TABLE 3

Inhibition ratio when concentration of test compound is 3 μM

| Ex | % |
|---|---|
| 52 | 31 |
| 53 | 59 |
| 54 | 64 |
| 62 | 44 |
| 64 | 19 |
| 66 | 34 |
| 76 | 49 |
| 83 | 23 |
| 95 | 10 |
| 96 | 23 |
| 99 | 36 |
| 123 | 44 |
| 130 | 22 |
| 132 | 21 |
| 134 | 51 |
| 167 | 29 |
| 169 | 33 |
| 176 | 34 |
| 182 | 45 |
| 183 | 33 |
| 185 | 35 |
| 187 | 31 |
| 200 | 50 |
| 213 | 59 |
| 215 | 29 |
| 227 | 33 |
| 247 | 10 |
| 428 | 17 |
| 432 | 40 |
| 449 | 12 |
| 495 | 37 |
| 500 | 31 |
| 504 | 22 |
| 531 | 15 |
| 602 | 11 |
| 609 | 10 |
| 623 | 11 |
| 671 | 25 |
| 673 | 27 |
| 723 | 40 |
| 725 | 18 |

Invention Example 823

Evaluation of BEC 1 Current Inhibitory Activity by a Compound Using an Electrophysiological Technique BEC 1-expressing cells were voltage-clamped and whole-cell current was recorded by the whole-cell voltage-clamp method. A solution containing 140 mM NaCl, 5.4 mM KCl, 2 mM CaCl$_2$, 0.8 mM MgCl$_2$, 15 mM glucose and 10 mM HEPES (pH=7.4 by adding NaOH) was used as the extracellular solution, and a solution containing 125 mM KCl, 1 mM CaCl$_2$, 2 mM MgCl$_2$, 11 mM EGTA and 10 mM HEPES (pH=7.2 by adding KOH) was used as the intracellular solution (patch electrode solution).

A continuous outward current is induced by depolarizing the membrane potential from −90 mV to 0 mV. By comparing amplitude of this outward current in the absence of an agent (control value) with the current amplitude at the time of the administration of a compound to be tested (test value), % inhibition [(test value/control value)×100] was calculated.

Test Results

As a result, in the case of the compound of Invention Example 13, it showed 50% or more of inhibition at a concentration of 1 µM.

Invention Example 824

Preparation of Transgenic Mouse

<Construction of Transgene for BEC 1-Overexpressing Transgenic Mouse Preparation>

The transgene for production of a transgenic mouse overexpressing BEC 1 having the amino acid sequence described in SEQ ID NO:2 comprises a gene in which a BEC 1 cDNA (SEQ ID NO:1) with a 5' intron and poly(A) addition signal is linked to a downstream of the promoter region of α-calcium-calmodulin-dependent kinase II gene. The promoter region of α-calcium-calmodulin-dependent kinase II was obtained as two fragments having a mutually overlapping region, by PCR using a C57BL/6 mouse genomic DNA as the template. The C57BL/6 mouse genomic DNA was purified from a blood sample of the same mouse using a genomic DNA extraction kit (QIAamp DNA Blood Midi Kit, mfd. by QIAGEN). Primers were designed based on the sequence registered in a gene data base GenBank (Accession No. AJ222796). A gene fragment of 4.6 kb was obtained using an oligonucleotide comprising the nucleotide sequence represented by SEQ ID NO:3 as the forward primer and using an oligonucleotide comprising the nucleotide sequence represented by SEQ ID NO:4 as the reverse primer. An AatII recognition sequence is added to the 5' terminal side of the aforementioned forward primer. In addition, a gene fragment of 3.7 kb was obtained using an oligonucleotide comprising the nucleotide sequence represented by SEQ ID NO:5 as the forward primer and using an oligonucleotide comprising the nucleotide sequence represented by SEQ ID NO:6 as the reverse primer. A SalI recognition sequence is added to the 5' terminal side of the aforementioned reverse primer. Each PCR was carried out using a DNA polymerase (Pfu Turbo, mfd. by Stratagene) by employing a thermal denaturation at 99° C. (1 minute) and subsequent repetition of 45 cycles each comprising 99° C. (15 seconds), 58° C. (15 seconds) and 75° C. (10 minutes), or a thermal denaturation at 95° C. (1 minute) and subsequent repetition of 40 cycles each comprising 95° C. (15 seconds), 62° C. (15 seconds) and 75° C. (8 minutes), and the thus obtained gene fragment was cloned into a cloning vector (pCR-XL-TOPO plasmid, mfd. by Invitrogen). An endogenous XmaI recognizing sequence is present in the overlapping region of the 4.6 kb fragment and 3.7 kb fragment. The 4.6 kb fragment was digested with restriction enzymes AatII and XmaI, and the 3.7 kb fragment was digested with restriction enzymes XmaI and SalI. The thus obtained respective fragments were ligated and cloned into a plasmid pUC18 (mfd. by Toyobo) making use of the AatII and SalI recognition sequences. The α-calcium-calmodulin-dependent kinase II promoter region of interest was obtained by the above operation.

On the other hand, the BEC 1 cDNA (SEQ ID NO:1) was obtained as a fragment containing a 5' intron and poly(A) addition signal by PCR using a potassium channel expression vector pME-E1 (described in WO 99/37677) as the template. An oligonucleotide comprising the nucleotide sequence represented by SEQ ID NO:7 was designed as the forward primer, and an oligonucleotide comprising the nucleotide sequence represented by SEQ ID NO:8 as the reverse primer, respectively from the upstream sequence of 5' intron and downstream sequence of poly(A) addition signal.

A SalI recognition sequence was added to the aforementioned forward primer, and KpnI and NotI recognizing sequences to the reverse primer. PCR was carried out using a DNA polymerase (Pfu Turbo, mfd. by Stratagene) by employing a thermal denaturation at 96° C. (1 minute) and subsequent repetition of 30 cycles each comprising 96° C. (15 seconds), 60° C. (15 seconds) and 75° C. (8 minutes). The thus obtained 3.7 kb fragment was cloned into a cloning vector (pCR-XL-TOPO plasmid, mfd. by Invitrogen). This fragment was subcloned into a plasmid pUC18 (mfd. by Toyobo) making use of the SpeI recognition sequence and KpnI recognition sequence, and the aforementioned α-calcium-calmodulin-dependent kinase II promoter region was further subcloned into its upstream making use of the AatII recognition sequence and SalI recognition sequence. A plasmid (named pCM-E1 plasmid) having a transgene (12 kb) for use in the preparation of a BEC 1-overexpressing transgenic mouse was finally obtained by the above operation.

<Preparation and Identification of BEC 1 Over-Expression Transgenic Mouse>

The transgene (12 kb) for production of a BEC-overexpressing transgenic mouse was cut out from pCM-E1 using restriction enzymes AatII and NotI and then isolated and purified. The thus obtained gene was micro-injected into 283 fertilized eggs of F1 hybrid mice of C57BL/6 and DBA2 mice, and then the resulting fertilized eggs were transplanted into oviducts of ICR foster mother mice (Hogan, B. et al. (1986), Manipulating the mouse embryo: a laboratory manual, Plainview, N.Y.; Cold Harbor Press). The pregnant mice were allowed to undergo spontaneous delivery, and the thus obtained 81 offspring mice were subjected to the identification of transgenic mice.

In order to identify transgenic mice, PCR was carried out using genomic DNA isolated from the tail of each offspring mouse as the template. The genomic DNA was purified from the tail of each mouse using a genomic DNA extraction kit (MagExtractor—Genome—, mfd. by Toyobo). When an oligonucleotide comprising the nucleotide sequence represented by SEQ ID NO:9 is designed as the forward primer, and an oligonucleotide comprising the nucleotide sequence represented by SEQ ID NO:10 as the reverse primer, from the BEC 1 cDNA (SEQ ID NO:1), and PCR is carried out using them, a 245 bp fragment is amplified from the transgene, and a 338 bp fragment containing 93 bp intron of mouse BEC 1 from the mouse genomic DNA. PCR was carried out on the thus obtained baby-mouse genomic DNA preparations using these priers.

PCR was carried out using a DNA polymerase (AmpliTaq, mfd. by Roche) by employing a thermal denaturation at 94° C. (1 minute) and subsequent repetition of 35 cycles each comprising 94° C. (15 seconds), 60° C. (15 seconds)

and 72° C. (30 seconds). As a result, it was identified that 16 of the 81 baby mice are transgenic mice.

<Determination of BEC 1 mRNA>

In order to confirm that the introduced gene is actually functioning and BEC 1 mRNA is over-expressing, expression of BEC 1 mRNA in the brain of transgenic mouse was analyzed. In order to obtain F1 mice for brain extraction use, 11 animals among the 16 transgenic mice were crossed with C57BL/6 mice. As a result, transfer of the transgene to F1 mice was confirmed in 5 transgenic mice. The fore-brain and cerebellum were sampled from each of the thus obtained F1 transgenic mice (4-week-old) to isolate respective RNA.

Each RNA was digested with a DNase (mfd. by Promega) for the purpose of preventing contamination of genomic DNA. The number of copies of BEC 1 mRNA in the thus obtained RNA was determined by a real time PCR using PRISM 7700 (mfd. by ABI) and a fluorescence reagent SYBR Green (mfd. by Molecular Probe). A single-stranded cDNA synthesized from each RNA using a reverse transcriptase-polymerase chain reaction kit (Advantage RT-for-PCR Kit, mfd. by Clontech) was used as the template of the real time PCR. An oligonucleotide comprising the nucleotide sequence represented by SEQ ID NO:11 was designed as the forward primer, and an oligonucleotide comprising the nucleotide sequence represented by SEQ ID NO:12 as the reverse primer, from a sequence common to the transgene, human BEC 1, and rat and mouse BEC 1.

As a result of the real time PCR, over-expression of fore-brain-selective BEC 1 mRNA about 10 times larger than that of wild type was found in 3 lines (# 6-5, # 7-7 and # 9-5) among the 5 lines of transgenic mice. By selecting the line # 9-5, expressed amounts of BEC 1 mRNA in respective regions of the brain (cerebral cortex, hippocampus, corpus striatum, hypothalamus, thalamus, mid-brain, brain stem, cerebellum) of wild type mouse were compared with those of the transgenic mouse. As a result, it was confirmed that the BEC 1 mRNA over-expression in the transgenic mouse is significant in cerebral cortex, hippocampus and corpus striatum in which the expression was also found in the wild type.

Invention Example 825

<Analysis of Learning and Memory of BEC 1-Overexpressing Transgenic Mouse in a Morris Water Maze>

In order to analyze action of BEC 1 over-expression upon cognition, learning and memory of # 9-5 line transgenic mice and that of wild type mice in a Morris water maze were compared.

Male 10-week-old transgenic mice (12 animals) and wild type mice (15 animals) were used. A circular pool of 100 cm in diameter was filled with water which had been clouded using paints, and a circular platform of 10 cm in diameter was arranged at a position of 5 mm below the water. Room temperature and water temperature at the time of the test was 23° C. Swimming pattern of each mouse put into the pool was recorded and analyzed by a water maze image analyzer (NIH image, mfd. by O'Hara & CO.), and the escape latency to the platform and the time spent in each quadrant of the pool were measured. Maximum trial duration was 70 seconds, and the training was carried out 3 trials per day for 5 days. The escape latency to the platform on the first day of the training was almost the same value in both groups, but the escape latency was prolonged in the transgenic mice than the wild type mice on and after the 3rd day of the start of the training. On the final day of the training, the escape latency to the platform (average value±standard deviation) became 6.9±1.0 seconds in the wild type and 18.1±6.4 seconds in the transgenic mice, thus showing a statistically significant difference ($p<0.05$: two-way layout analysis of variance).

After completion of the training, each mouse received a single 40 seconds test with the platform had been removed, and the time of the mouse spend in the platform-existed quadrant was measured. As a result, the time spend in the platform-existed quadrant of transgenic mice was significantly shorter than that of the wild type ($p<0.01$: Student's t test).

The above results show that learning and memory on the platform position are reduced in the transgenic mice.

Invention Example 826

<Analysis of Learning and Memory of BEC 1-Overexpressing Transgenic Mouse in a Passive Evasion Test>

Female # 9-5 line transgenic mice (6 animals) and wild type mice (8 animals), 8-week-old, were used. Each mouse was put into the light compartment of a light and dark test apparatus for mice (mfd. by O'Hara & CO.), and a 60 V shock for 2 seconds was applied to the mouse when it entered the dark compartment. The mouse was again put into the light compartment 24 hours thereafter, and the entry latency into the dark compartment at this time was measured.

As a result, the entry latency of the transgenic mice was 167 seconds (median value) which was significantly short compared to the 600 seconds (median value) of the wild type mice ($p<0.05$: Wilcoxon rank sum test).

It was shown that the ability to learn the dark compartment-related electric shock is reduced in the transgenic mice.

Invention Example 827

Electricity Chorea Shock (ECS)-Induced Learning Disorder (Mouse Passive Evasion Reaction Test)

The evaluation was carried out in the following manner with reference to a report (*Eur. J. Pharmacology*, 321; 273-278, 1997).

Animals; Male ddy mice (SLC, five weeks of age at the time of the training) were used. Arranged into 31 or 32 animals per group.

<Test Procedure>

Drug Preparation

A compound to be evaluated was suspended in a solution prepared by dissolving methyl cellulose in physiological saline to a concentration of 0.5% (hereinafter, 0.5% methyl cellulose solution). The administration volume was set to 10 ml per 1 kg body weight. As a placebo of the compound to be evaluated, 10 ml of the 0.5% methyl cellulose solution per 1 kg body weight (hereinafter, vehicle) was administered.

Training (1) Mice were allowed to stand in a laboratory for 1 hour or more on the first day of the test.

(2) Each mouse was put into the light compartment of a passive avoidance task apparatus and allowed to stand for 30 seconds. Thereafter, the Guillotine door was opened. When the mouse received an electric shock (intensity 60 V, delay 1 sec, duration 3 sec) by entering into the dark compartment and then returned into the light compartment, the Guillotine door was closed to let the mouse to stand for 30 seconds in the light compartment.

(3) The mouse was removed and attached with a cornea electrode quickly (within 1 minute), and then an electroconvulsive shock (ECS, 50 Hz, interval 20 ms, duration 10 ms, amplitude 20 mA, gate 1 sec) was applied.

(4) The compound was administered intraperitoneally.

(5) Returned to the home cage.

(6) After completion of the training, allowed to stand in the laboratory for 60 minutes or more and then returned to the rearing room.

Test (24 Hours After the Training)

(1) Animals were allowed to stand in a laboratory for 1 hour or more.

(2) Each mouse was put into the light compartment and allowed to stand for 30 seconds, and then the Guillotine door was opened.

(3) A period of time until the mouse crossed a sensor in the dark compartment after opening the Guillotine door (step-through latency) was recorded. The maximum measuring time was set to 600 seconds.

(4) The step-through latency was employed as the index of the formation of learning. Effect of the compound on ECS-induced amnesia was evaluated by comparison between a step-through latency of (ECS+vehicle administration) group and a that of (ECS+evaluation compound administration) group. Data were analyzed using two-tailed steel test. P<0.05 was considered significant. When the compound described in Invention Example 744 was intraperitoneally administered, its minimum effective dose was 3 mg/kg.

As a result of the above, it was confirmed that the compound described in Invention Example 744 as a typical compound has the BEC 1 potassium channel inhibitory activity and shows the improving effect on electroconvulsive shock (ECS)-induced amnesia in the mouse passive avoidance task.

TABLE 4

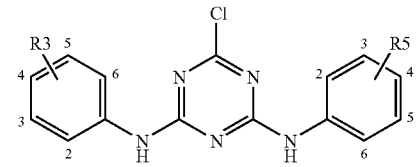

(The numbers 2 to 6 in the formula above represent respective bonding positions of $R^3$ and $R^5$.)

| Ref | $R^3$ | $R^5$ | DATA:(MS) |
|---|---|---|---|
| 1 | H | 4-F | 316($M^+$ + 1) |
| 2 | H | 4-$CF_3$ | 366($M^+$ + 1) |
| 3 | H | 3-F | 316($M^+$ + 1) |
| 4 | H | 3,4-diF | 334($M^+$ + 1) |
| 5 | H | 4-F, 3-Me | 330($M^+$ + 1) |
| 6 | 4-Me | 4-F | 330($M^+$ + 1) |
| 7 | 4-MeO | 4-F | 346($M^+$ + 1) |
| 8 | 4-Cl | 4-F | 350($M^+$ + 1) |
| 9 | 4-$CF_3$ | 4-F | 384($M^+$ + 1) |
| 10 | 3-F | 4-F | 334($M^+$ + 1) |
| 11 | 3-Me | 4-F | 330($M^+$ + 1) |
| 12 | 3-MeO | 4-F | 346($M^+$ + 1) |

TABLE 5

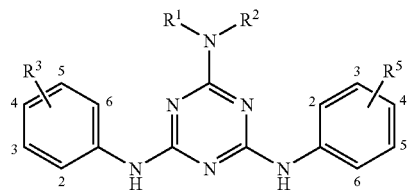

(The numbers 2 to 6 in the formula above represent respective bonding positions of $R^3$ and $R^5$.)

| Ex | $\underset{|}{R^1\diagdown N\diagup R^2}$ | $R^3$ | $R^5$ | Salt/Solvate | DATA |
|---|---|---|---|---|---|
| 1 | Py-4-yl$CH_2$NH— | H | H | free | m.p.: 159-160<br>$^1$H-NMR: 4.64(2H, d, J=6.4 Hz), 5.50-5.60(1H, m), 6.93(2H, s), 7.02-7.10(2H, m), 7.24-7.35(6H, m), 7.40-7.61(4H, m), 8.55-8.58(2H, m)/$CDCl_3$ |
| 2 | Py-3-yl$CH_2$NH— | H | H | 1.9 HCl 0.7 $H_2O$ | m.p.: 180-182<br>$^1$H-NMR: 4.75(2H, d, J=4.4 Hz), 7.04-7.20(2H, m), 7.23-7.42(4H, m), 7.43-7.80(4H, m), 8.05(1H, dd, J=5.9 Hz, 7.8 Hz), 8.33-8.67(1H, m), 8.85(1H, d, J=5.4 Hz), 8.90-9.20(2H, m)/DMSO-$d_6$ |
| 3 | Py-2-yl$CH_2$NH— | H | H | free | m.p.: 125-127<br>$^1$H-NMR: 4.75(2H, d, J=5.9 Hz), 7.04(2H, t, J=7.5 Hz), 7.14-7.16(2H, m), 7.25-7.31(4H, m), 7.36(1H, d, J=7.5 Hz), 7.50-7.58(4H, m), 7.60-7.64(1H, m), 8.02(1H, brs), 8.51(1H, d, J=4.8 Hz)/$CDCl_3$ |
| 4 | 2-FPy-4-yl$CH_2$NH— | H | H | HCl | m.p.: 202-203<br>$^1$H-NMR: 4.63(2H, s), 6.98-7.40(8H, m), 7.45-7.60(2H, m), 7.61-7.78(2H, m), 8.21(1H, d, J=5.4 Hz), 8.75(1H, brs), 10.02(1H, brs), 10.20(1H, brs)/DMSO-$d_6$ |
| 5 | 2-ClPy-4-yl$CH_2$NH— | H | H | HCl 0.1 $H_2O$ | m.p.: 201-204<br>$^1$H-NMR: 4.61(2H, s), 7.02-7.19(2H, m), 7.26(2H, t, J=7.4 Hz), 7.26-9.80(8H, m), 8.38(1H, d, J=5.4 Hz), 8.96(1H, brs), 10.21(1H, brs), 10.46(1H, brs)/DMSO-$d_6$ |

TABLE 5-continued

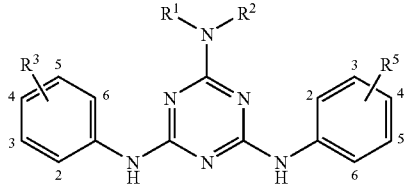

(The numbers 2 to 6 in the formula above represent respective bonding positions of R³ and R⁵.)

| Ex | $R^1\underset{|}{\overset{R^2}{N}}$ | R³ | R⁵ | Salt/Solvate | DATA |
|---|---|---|---|---|---|
| 6 | 2-iPrPy-4-ylCH₂NH— | H | H | 2 HCl | m.p.: 185-187<br>1.34(6H, d, J=6.8 Hz), 3.32-3.50(1H, m), 4.73-7.87(2H, m), 6.80-7.15 (2H, m), 7.16-7.28(2H, m), 7.30-7.40(4H, m), 7.41-7.57(2H, m), 7.61-7.78(2H, m), 7.85(1H, d, J=5.9 Hz), 8.93(1H, brs), 10.09(1H, brs), 10.34 (1H, brs)/DMSO-d₆ |
| 7 | BzlNH— | H | H | HCl 0.2 H₂O | m.p.: 178-180<br>¹H-NMR: 4.60(2H, brs), 7.05-7.10(2H, m), 7.25-7.43(8H, m), 7.53-7.75 (4H, m), 9.15(1H, brs). 10.39(1H, brs). 10.64(1H, brs)/DMSO-d₆ |
| 8 | 4-FPhCH₂NH— | H | H | HCl | m.p.:188-190<br>¹H-NMR: 4.57(2H, brs), 7.09-7.22(4H, m), 7.25-7.50(6H, m), 7.52-7.75 (4H, m), 9.14(1H, brs), 10.40(1H, brs), 10.64(1H, brs)/DMSO-d₆ |
| 9 | 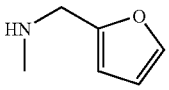 | H | H | 0.4 AcOEt | m.p.:81-83<br>¹H-NMR: 4.63(2H, d, J=5.9 Hz), 5.47-5.55(1H, m), 6.25(1H, dd, J=1.1 Hz, 3.2 Hz), 6.32(1H, dd, J=1.6 Hz, 3.2 Hz), 6.97(2H, brs), 7.05(2H, t, J=7.5 Hz), 7.27-7.34(4H, m), 7.36-7.37(1H, m), 7.50-7.62(4H, m)/CDCl₃ |
| 10 | 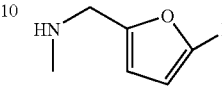 | H | H | HCl | m.p.:165-167<br>¹H-NMR: 2.25(3H, s), 4.51(2H, s), 6.02(1H, d, J=2.0 Hz), 6.15-6.35(1H, m), 7.05-7.20(2H, m), 7.25-7.45(4H, m), 7.55-7.80(4H, m), 8.87(1H, brs). 10.10-10.70(2H, m)/DMSO-d₆ |
| 11 | 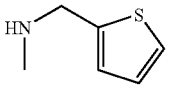 | H | H | HCl | m.p.: 188-190<br>¹H-NMR: 4.75(2H, brs), 6.97-7.02(1H, m), 7.05-7.40(3H, m), 7.44(1H, d, J=4.9 Hz), 7.58-7.78(4H, m), 9.12(1H, brs), 10.40(1H, brs), 10.58 (1H, brs)/DMSO-d |

TABLE 6

(continued from Table 5)

| | | | | | |
|---|---|---|---|---|---|
| 12 | Py-4-yl(CH₂)₂NH— | H | H | free | m.p.: 228-229<br>¹H-NMR: 2.93(2H, t, J=7 Hz), 3.69-3.74(2H, m), 5.10(1H, brs), 6.79(1H, brs), 6.88(1H, brs), 7.07(2H, t, J=7.5 Hz), 7.16(2H, d, J=5.9 Hz), 7.30-7.34(4H, m), 7.50-7.65(4H, m), 8.53-8.54(2H, m)/CDCl₃ |
| 13 | iPrNH— | H | H | free | Known compound |
| 14 | PenNH— | H | H | free | m.p.: 78-81<br>¹H-NMR: 0.91(3H, t, J=7 Hz), 1.31-1.40(4H, m), 1.56-1.63(2H, m), 3.41 (2H, q, J=7 Hz), 5.10-5.18(1H, m), 7.02-7.07(4H, m), 7.28-7.32(4H, m), 7.53-7.65(4H, m)/CDCl₃ |
| 15 | cPrCH₂NH— | H | H | HCl | m.p.: 197-199<br>¹H-NMR: 0.26-0.32(2H, m), 0.44-0.54(2H, m), 1.04-1.16(1H, m), 3.22-3.32(2H, m), 7.07-7.21(2H, m), 7.28-7.43(4H, m), 7.50-7.80(4H, m), 8.73(1H, brs), 10.10-10.90(2H, m)/DMSO-d₆ |
| 16 | HCCCH₂NH— | H | H | HCl | m. p.: 195-197<br>¹H-NMR: 3.25(1H, s), 4.16(2H, s), 7.05-7.17(2H, m), 7.28-7.40(4H, m), 7.60-7.80(4H, m), 8.65(1H, brs), 10.10-10.45(2H, m)/DMSO-d₆ |
| 17 | MeO(CH₂)₂NH— | H | H | free | m.p.: 128-129<br>¹H-NMR: 3.39(3H, s), 3.59(2H, t, J=4.3), 3.63-3.67(2H, m), 6.18(1H, brs), 7.01-7.07(3H, m), 7.19(1H, brs), 7.29-7.33(4H, m), 7.51-7.64(4H, m)/CDCl₃ |
| 18 | MeO(CH₂)₃NH— | H | H | HCl | m.p.: 154-155<br>¹H-NMR: 1.76-1.87(2H, m), 3.25(3H, s), 3.37-3.45(4H, m), 7.05-7.20 (2H, m), 7.27-7.42(4H, m), 7.50-7.80(4H, m), 8.50(1H, s), 10.10-10.64 (2H, m)/DMSO-d₆ |
| 19 | MeS(CH₂)₃NH— | H | H | HCl | m.p.: 162-163<br>1.79-1.90(2H, m), 2.06(3H, s), 2.55(2H, t, J=7.3 Hz), 3.38-3.52(2H, m), 7.06-7.20(2H, m), 7.26-7.44(4H, m), 7.53-7.82(4H, m), 8.66(1H, brs), 10.10-10.80(2H, m)/DMSO-d₆ |

TABLE 6-continued (continued from Table 5)

| | | | | | |
|---|---|---|---|---|---|
| 20 | [HN-CH2-tetrahydrofuran-2-yl] | H | H | free | m.p.: 149-150<br>$^1$H-NMR: 1.62-1.71(1H, m), 1.86-2.04(3H, m), 3.47-3.54(1H, m), 3.66-3.72(1H, m), 3.74-3.80(1H, m), 3.88-3.94(1H, m), 4.08-4.14(1H, m), 6.28(1H, brs), 7.03-7.08(3H, m), 7.28-7.37(5H, m), 7.50-7.63(4H, m)/CDCl$_3$ |
| 21 | HO(CH$_2$)$_3$NH— | H | H | HCl | m.p.: 191-192<br>$^1$H-NMR: 1.69-1.79(2H, m), 3.38-3.55(4H, m), 7.07-7.20(2H, m), 7.26-7.43(4H, m), 7.50-7.85(4H, m), 8.60(1H, brs), 10.10-10.75(2H, m)/DMSO-d$_6$ |
| 22 | HO(CH$_2$)$_5$NH— | H | H | free | m.p.: 118-119<br>$^1$H-NMR: 1.42-1.49(2H, m), 1.58-1.67(6H, m), 3.40-3.46(2H, m), 3.65(2H, t, J=6.4), 5.16(1H, s), 6.98-7.07(4H, m), 7.29-7.33(4H, m), 7.50-7.64(4H, m)/CDCl$_3$ |
| 23 | HO(CH$_2$)$_2$O(CH$_2$)$_2$NH— | H | H | HCl | m.p.: 167-169<br>$^1$H-NMR: 3.46-3.62(8H, m), 7.09-7.17(2H, m), 7.30-7.40(4H, m), 7.60-7.75(4H, m), 8.47(1H, brs), 10.15-10.70(2H, m)/DMSO-d$_6$ |
| 24 | [HN-CH2-dihydrofuran-2(3H)-one] | H | H | HCl<br>H$_2$O | m.p.: 138-140<br>$^1$H-NMR: 4.24-4.30(1H, m), 4.33-4.45(1H, m), 4.50-5.00(4H, m), 7.03-7.10(2H, m), 7.25-7.35(4H, m), 7.60-7.75(4H, m), 8.17(1H, brs), 9.70-9.95(2H, m)/DMSO-d$_6$ |
| 25 | Py-4-ylCH$_2$NH— | 4-F | 4-F | 1.8 HCl<br>H$_2$O | m.p.: 191-193<br>$^1$H-NMR: 4.80(2H, s), 6.98-7.30(6H, m), 7.31-7.95(6H, m), 8.03(2H, d, J=5.9 Hz), 8.70-9.00(3H, m), 9.75-10.95(2H, m)/DMSO-d$_6$ |
| 26 | Py-3-ylCH$_2$NH— | 4-F | 4-F | 1.8 HCl<br>0.8 H$_2$O | m.p.: 208-210<br>$^1$H-NMR: 4.62-4.84(2H, m), 4.05-7.28(4H, m), 7.33-7.83(4H, m), 8.06(1H, dd, J=5.8 Hz, 7.9 Hz), 8.57(1H, brs),<br>8.85(1H, d, J=5.9 Hz), 8.96(1H, brs), 9.77-10.85(2H, m)/DMSO-d$_6$ |

TABLE 7

(continued from Table 6)

| | | | | | |
|---|---|---|---|---|---|
| 27 | Py-2-ylCH$_2$NH— | 4-F | 4-F | 2 HCl | m.p.: 175-176<br>$^1$H-NMR: 4.88(2H, d, J=4.9 Hz), 7.00-7.29(4H, m), 7.30-7.98(6H, m), 8.43(1H, t, J=7.8 Hz), 8.62(1H, brs), 8.82(1H, d, J=5.4 Hz), 9.70-10.40(2H, m)/DMSO-d$_6$ |
| 28 | BzlNH— | 4-F | 4-F | HCl<br>0.7 H$_2$O | m.p.: 176-178<br>$^1$H-NMR: 4.57(2H, brs), 7.08-7.31(5H, m), 7.32-7.42(4H, m), 7.46-7.77(4H, m), 9.06(1H, brs), 10.33(1H, brs), 10.59(1H, brs)/DMSO-d$_6$ |
| 29 | 4-FPhCH$_2$NH— | 4-F | 4-F | HCl | m.p.: 166-167<br>$^1$H-NMR: 4.54(2H, brs), 7.08-7.26(6H, m), 7.32-7.48(2H, m), 7.50-7.80(4H, m), 8.92(1H, brs), 9.85-10.75(2H, m)/DMSO-d$_6$ |
| 30 | [HN-CH2-furan-2-yl] | 4-F | 4-F | HCl | m.p.: 179-180<br>$^1$H-NMR: 4.55(2H, s), 6.26-6.47(2H, m), 7.10-7.24(4H, m), 7.51-7.79(5H, m), 8.65(1H, brs), 9.80-10.55(2H, m)/DMSO-d$_6$ |
| 31 | [HN-CH2-thiophen-2-yl] | 4-F | 4-F | HCl | m.p.: 180-182<br>$^1$H-NMR: 4.73(2H, brs), 6.94-7.02(1H, m), 7.05-7.26(5H, m), 7.43(1H, d, J=4.9 Hz), 7.52-7.78(4H, m), 8.97(1H, brs), 10.10-10.72(2H, m)/DMSO-d$_6$ |
| 32 | iPrNH— | 4-F | 4-F | HCl | m.p.: 186-188<br>$^1$H-NMR: 1.21(6H, d, J=6.4 Hz), 3.97-4.33(1H, m), 7.10-7.30(4H, m), 7.43-7.87(4H, m), 8.58(1H, brs), 9.98-11.03(2H, m)/DMSO-d$_6$ |
| 33 | PenNH— | 4-F | 4-F | HCl<br>H$_2$O | m.p.: 170-171<br>$^1$H-NMR: 0.88(3H, t, J=6.9 Hz), 1.20-1.40(4H, m), 1.45-1.65(2H, m), 3.34(2H, s), 7.08-7.30(4H, m), 7.45-7.85(4H, m), 8.61(1H, brs), 9.90-11.00(2H, m)/DMSO-d$_6$ |
| 34 | cPrCH$_2$NH— | 4-F | 4-F | HCl<br>0.7 H$_2$O | m.p.: 184-186<br>$^1$H-NMR: 0.20-0.36(2H, m), 0.40-0.57(2H, m), 0.98-1.21(1H, m), 3.36(2H, s), 7.07-7.30(4H, m), 7.35-7.85(4H, m), 8.79(1H, brs), 10.45(1H, brs), 10.71(1H, brs)/DMSO-d$_6$ |
| 35 | MeO(CH$_2$)$_2$NH— | 4-F | 4-F | HCl | m.p.: 175-176<br>$^1$H-NMR: 3.29(3H, s), 3.48-3.56(4H, m), 7.11-7.26(4H, m), 7.46-7.78(4H, m), 8.54(1H, brs), 10.20-10.80(2H, m)/DMSO-d$_6$ |

TABLE 7-continued (continued from Table 6)

| # | R | X | Y | Salt | Properties |
|---|---|---|---|------|------------|
| 36 | (tetrahydrofuran-2-ylmethyl)NH— | 4-F | 4-F | HCl | m.p.: 171-174<br>1.4 H$_2$O $^1$H-NMR: 1.51-1.65(1H, m), 1.73-2.04(3H, m), 3.30-3.52(2H, m), 3.58-3.80(1H, m), 3.82-3.87(1H, m), 3.95-4.07(1H, m), 7.09-7.28 (4H, m), 7.46-7.81(4H, m), 8.60(1H, brs), 9.95-11.00(2H, m)/DMSO-d$_6$ |
| 37 | HO(CH$_2$)$_5$NH— | 4-F | 4-F | HCl | m.p.: 162-163<br>$^1$H-NMR: 1.29-1.40(2H, m), 1.40-1.50(2H, m), 1.51-1.63(2H, m), 3.29-3.44(4H, m), 7.03-7.27(4H, m), 7.52-7.79(4H, m), 8.62(1H, brs), 10.20-10.76(2H, m)/DMSO-d$_6$ |
| 38 | HO(CH$_2$)$_2$O(CH$_2$)$_2$NH | 4-F | 4-F | HCl | m.p.: 151-152<br>$^1$H-NMR: 3.40-3.67(8H, m), 7.10-7.28(4H, m), 7.36-7.90(4H, m), 8.65(1H, brs), 9.95-11.05(2H, m)/DMSO-d$_6$ |
| 39 | iPrNH— | 4-MeO | 4-MeO | HCl | m.p.: 188-190<br>$^1$H-NMR: 1.21(6H, d, J=5.8Hz), 3.75(6H, s), 6.77-7.05(4H, m), 7.30-7.67(4H, m), 8.70(1H, brs), 9.75-11.15(2H, m)/DMSO-d$_6$ |
| 40 | iPrNH— | 3-MeO | 3-MeO | HCl | m.p.: 180-182<br>$^1$H-NMR: 1.23(6H, d, J=6.8 Hz), 3.74(6H, s), 4.10-4.23(1H, m), 6.64-6.81(2H, m), 7.10-7.52(6H, m), 8.65(1H,brs), 10.00-11.05(2H, m)/DMSO-d$_6$ |

TABLE 8

(continued from Table 7)

| # | R | X | Y | Salt | Properties |
|---|---|---|---|------|------------|
| 42 | iPrNH— | 4-NO$_2$ | 4-NO$_2$ | 0.1 AcOEt | m.p.: 287-288<br>$^1$H-NMR: 1.22(6H, d, J=6.9 Hz), 4.14-4.26(1H, m), 7.48(1H, d, J=7.8 Hz), 8.06-8.23(8H, m), 9.88(1H, s), 10.00(1H, s)/DMSO-d$_6$ |
| 43 | iPrNH— | 4-CF$_3$ | 4-CF$_3$ | AcOEt | m.p.: 176-177<br>$^1$H-NMR: 1.20(6H, d, J=6.9 Hz), 4.12-4.23(1H, m), 7.23(1H, d, J=7.9 Hz), 7.55-7.65(4H, m), 8.05(4H, d, J=7.8 Hz), 9.45(1H, s), 9.59(1H, s)/DMSO-d$_6$ |
| 44 | iPrNH— | 4-CN | 4-CN | 0.4 AcOEt | m.p.: 241-242<br>$^1$H-NMR: 1.20(6H, d, J=6.8 Hz), 4.11-4.24(1H, m), 7.36(1H, d, J=8.3 Hz), 7.66-7.76(4H, m), 7.98-8.10(4H, m), 9.62(1H, s), 9.73(1H, s)/DMSO-d$_6$ |
| 45 | iPrNH— | H | 4-F | HCl | m.p.: 205-206<br>$^1$H-NMR: 1.22(6H, d, J=6.4 Hz), 4.02-4.28(1H, m), 7.07-7.27(3H, m), 7.29-7.45(2H, m), 7.46-7.85(4H, m), 8.75(1H, brs), 10.10-11.25(2H, m)/DMSO-d$_6$ |
| 46 | iPrNH— | H | 4-Cl | HCl | m.p.: 201-203<br>$^1$H-NMR: 1.22(6H, d, J=6.4 Hz), 4.00-4.30(1H, m), 7.08-7.23(1H, m), 7.32-7.47(4H, m), 7.52-7.85(4H, m), 8.69(1H, brs), 10.15-11.15(2H, m)/DMSO-d$_6$ |
| 47 | iPrNH— | H | 4-Me | 1.5 HCl | m.p.: 194-195<br>$^1$H-NMR: 1.22(6H, d, J=6.4 Hz), 2.30(3H, s), 4.00-4.32(1H, m), 7.06-7.26(3H, m), 7.27-7.84(6H, m), 8.82(1H, brs), 10.55(1H, brs), 10.94(1H, brs)/DMSO-d$_6$ |
| 48 | iPrNH— | H | 4-MeO | 1.2 HCl 0.2 H$_2$O | m.p.: 174-177<br>$^1$H-NMR: 1.22(6H, d, J=6.3 Hz), 3.76(3H, s), 4.00-4.25(1H, m), 6.85-7.05(2H, m), 7.06-7.22(1H, m), 7.25-7.80(6H, m), 8.77(1H, brs), 9.90-11.20(2H, m)/DMSO-d$_6$ |
| 49 | iPrNH— | H | 4-CF$_3$ | HCl | m.p.: 198-200<br>$^1$H-NMR: 1.24(6H, d, J=6.3 Hz), 4.06-4.26(1H, m), 7.07-7.22(1H, m), 7.32-7.45(2H, m), 7.69(4H, d, J=8.3 Hz), 7.86-8.04(2H, m), 8.63(1H, brs), 10.17-11.15(2H, m)/DMSO-d$_6$ |
| 50 | iPrNH— | H | 3-Me | HCl 0.1 H$_2$O | m.p.: 182-184<br>MS: 335(M$^+$ +1)<br>$^1$H-NMR: 1.23(6H, d, J=6.3 Hz), 2.31(3H, s), 4.00-4.30(1H, m), 6.88-7.05(1H, m), 7.05-7.80(8H, m), 8.61(1H, brs), 9.90-11.05(2H, m)/DMSO-d$_6$ |

Compound of Example 41

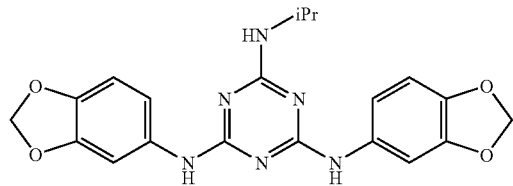

DATA
1 HCl
m.p.: 184-186 ¹H-NMR: 1.20 (6H, d, J=6.8 Hz), 3.85-4.40 (1H, m), 6.02 (4H, s), 6.77-7.07 (4H, m), 7.10-7.55 (2H, m), 8.55 (1H, brs), 9.85-10.85 (2H, m)/DMSO-$d_6$

TABLE 9

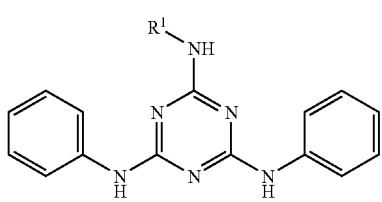

| Ex | $R^1$ | MASS | HPLC rt(min) |
|---|---|---|---|
| 51 | 4-FPhCH$_2$— | 387 | 2.77 |
| 52 | Me | 293 | 2.26 |
| 53 | Et | 307 | 2.40 |
| 54 | Pr | 321 | 2.57 |
| 55 | iPr | 321 | 2.56 |
| 56 | Bu | 335 | 2.75 |
| 57 | iBu | 349 | 2.91 |
| 58 | Pen | 349 | 2.93 |
| 59 | 1-Me-Hex | 377 | 3.18 |
| 60 | 1-Pr-Bu | 377 | 3.12 |
| 61 | Tetradecyl | 475 | 4.02 |
| 62 | cPr | 319 | 2.41 |
| 63 | Bzl—N⟨azetidinyl⟩—Me | 424 | 2.13 |
| 64 | cPen | 347 | 2.76 |
| 65 | cyclopentyl-NMe$_2$, Me | 390 | 2.12 |
| 66 | cyclopentyl-SMe, Me | 393 | 2.84 |
| 67 | cyclopentyl-SPh, Me | 455 | 3.16 |
| 68 | cyclopentyl-pyrrolidinyl, Me | 416 | 2.16 |
| 69 | cyclopentyl-piperidinyl, Me | 430 | 2.20 |
| 70 | cyclopentyl-N-Me-piperazinyl, Me | 445 | 2.15 |
| 71 | cyclopentyl-morpholinyl, Me | 432 | 2.10 |
| 72 | γ-butyrolactone-Me | 363 | 2.17 |
| 73 | Bzl—N⟨pyrrolidinyl⟩-Me (R) | 438 | 2.38 |
| 74 | Bzl—N⟨pyrrolidinyl⟩-Me (S) | 438 | 2.38 |
| 75 | 4-NO$_2$PhCH$_2$O(CO)—N⟨pyrrolidinyl⟩-Me | 527 | 2.93 |
| 76 | tetrahydrofuranyl-SMe, Me | 395 | 2.63 |
| 77 | tetrahydrofuranyl-pyrrolidinyl, Me | 418 | 1.99 |

TABLE 9-continued
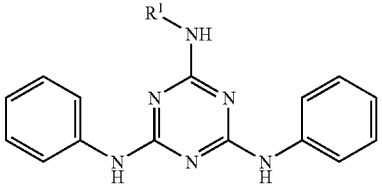
| Ex | R¹ | MASS | HPLC rt(min) |
|---|---|---|---|
| 78 | 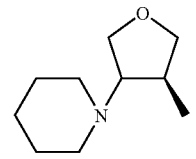 | 432 | 2.09 |
| 79 | 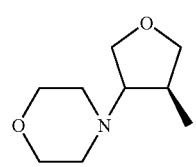 | 447 | 1.99 |
| 80 | 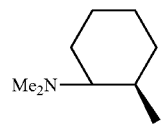 | 434 | 1.99 |
| 81 | cHex | 361 | 2.91 |
| 82 | 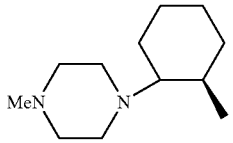 | 404 | 2.27 |
TABLE 10
(continued from Table 9)
| Ex | R¹ | MASS | HPLC rt(min) |
|---|---|---|---|
| 83 | 2-HOcHex | 377 | 2.55 |
| 84 | 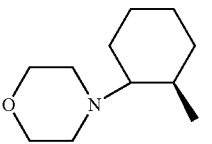 | 430 | 2.27 |
| 85 | 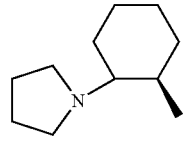 | 444 | 2.35 |
| 86 | 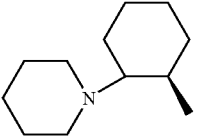 | 459 | 2.30 |
| 87 | | 446 | 2.28 |
| 88 | | 377 | 2.35 |
| 89 | | 417 | 3.42 |
| 90 | | 403 | 3.31 |
| 91 | | 402 | 2.25 |
| 92 | | 452 | 2.25 |
| 93 | | 434 | 2.74 |
| 94 | cHep | 375 | 3.03 |
| 95 | | 390 | 2.37 |
| 96 | | 390 | 2.36 |
| 97 | cOct | 389 | 3.16 |
| 98 | | 350 | 2.09 |
| 99 | EtO—CO(Me)CH— | 379 | 2.66 |

TABLE 10-continued
(continued from Table 9)
| Ex | R¹ | MASS | HPLC rt(min) |
|---|---|---|---|
| 100 | 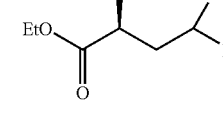 | 389 | 3.15 |
| 101 | Me₂N-CH₂-CH(Me)- | 364 | 2.01 |
| 102 | 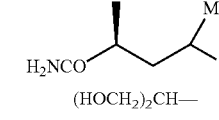 | 390 | 2.00 |
| 103 | 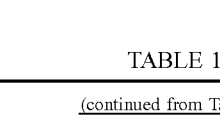 | 438 | 2.26 |
| 104 | 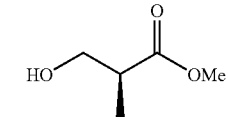 | 404 | 2.08 |
| 105 | 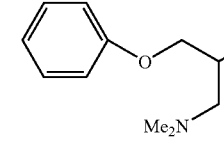 | 452 | 2.37 |
| 106 | 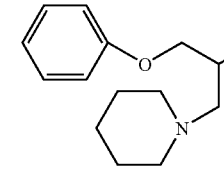 | 419 | 1.98 |
| 107 | 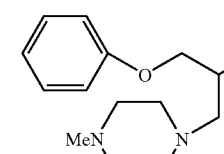 | 481 | 2.48 |
| 108 | 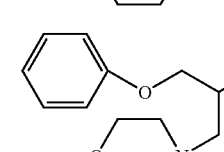 | 499 | 2.55 |
| 109 | 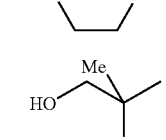 | 482 | 2.09 |
| 110 | 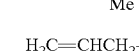 | 495 | 2.34 |
| 111 | 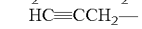 | 406 | 2.00 |
| 112 | HO-CH₂-CH(Me)- | 337 | 2.24 |
| 113 | Et₂N-CH₂CH₂CH₂-CH(Me)- | 420 | 2.09 |
TABLE 10-continued
(continued from Table 9)
| Ex | R¹ | MASS | HPLC rt(min) |
|---|---|---|---|
| 114 | EtO₂C-CH(Me)-CH₂-CH(Me)₂ | 421 | 3.13 |
| 115 | H₂NCO-CH(Me)-CH₂-CH(Me)₂ | 392 | 2.69 |
| 116 | (HOCH₂)₂CH— | 353 | 2.01 |
TABLE 11
(continued from Table 10)
| Ex | R¹ | MASS | HPLC rt(min) |
|---|---|---|---|
| 117 | HO-CH₂-CH(Me)-CO-OMe | 381 | 2.27 |
| 118 | PhO-CH₂-CH(Me)-CH₂-NMe₂ | 456 | 2.63 |
| 119 | PhO-CH₂-CH(Me)-CH₂-piperidinyl | 496 | 2.65 |
| 120 | PhO-CH₂-CH(Me)-CH₂-(N-methylpiperazinyl) | 511 | 2.54 |
| 121 | PhO-CH₂-CH(Me)-CH₂-morpholinyl | 498 | 2.60 |
| 122 | HO-CH₂-C(Me)₂- | 351 | 2.39 |
| 123 | H₂C=CHCH₂— | 319 | 2.48 |
| 124 | HC≡CCH₂— | 317 | 2.39 |

TABLE 11-continued (continued from Table 10)

| Ex | R¹ | MASS | HPLC rt(min) |
|---|---|---|---|
| 125 | (2-nitrobenzenesulfonamide, sec-butyl) | 521 | 2.59 |
| 126 | 2-HOPr | 337 | 2.22 |
| 127 | HOCH$_2$(HO)CHCH$_2$— | 353 | 2.06 |
| 128 | Me$_2$NCH$_2$(Me)$_2$CCH$_2$— | 392 | 1.97 |
| 129 | HOCH$_2$(Me)$_2$CCH$_2$— | 365 | 2.45 |
| 130 | H$_2$NCOCH$_2$— | 336 | 2.01 |
| 131 | 4-NCPhNHCOCH$_2$— | 437 | 2.50 |
| 132 | EtO$_2$CCH$_2$— | 365 | 2.50 |
| 133 | tBuO$_2$CCH$_2$— | 393 | 2.80 |
| 134 | cPr—CH$_2$— | 333 | 2.60 |
| 135 | (N-ethyl-2-ethylpyrrolidine) | 390 | 1.95 |
| 136 | (2-ethyltetrahydrofuran) | 363 | 2.43 |
| 137 | (dimethylbicyclic) | 415 | 3.34 |
| 138 | (4-fluorobenzyl-2-ethylmorpholine) | 486 | 2.39 |
| 139 | Et$_2$N(CH$_2$)$_2$— | 378 | 1.91 |
| 140 | iPr$_2$N(CH$_2$)$_2$— | 406 | 2.06 |
| 141 | (N-propylpyrrolidine) | 376 | 1.88 |
| 142 | (N-propylisoindoline) | 424 | 2.16 |
| 143 | (N-methyl-2-propylpyrrolidine) | 390 | 1.88 |
| 144 | (N-propylpiperidine) | 390 | 1.97 |

TABLE 11-continued (continued from Table 10)

| Ex | R¹ | MASS | HPLC rt(min) |
|---|---|---|---|
| 145 | (N-propylmorpholine) | 392 | 1.86 |
| 146 | AcNH(CH$_2$)$_2$— | 364 | 2.15 |
| 147 | Et(3-MePh)N(CH$_2$)$_2$— | 440 | 2.65 |
| 148 | MeO(CH$_2$)$_2$— | 337 | 2.32 |
| 149 | HO(CH$_2$)$_2$O(CH$_2$)$_2$— | 367 | 2.18 |
| 150 | EtO$_2$C(CH$_2$)$_3$— | 393 | 2.62 |
| 151 | Me$_2$N(CH$_2$)$_3$— | 364 | 1.84 |
| 152 | Et$_2$N(CH$_2$)$_3$— | 392 | 1.91 |
| 153 | (N-butylpyrrolidine) | 390 | 1.93 |
| 154 | (N-butyl-2-pyrrolidinone) | 404 | 2.29 |

TABLE 12

(continued from Table 11)

| Ex | R¹ | MASS | HPLC rt(min) |
|---|---|---|---|
| 155 | (N-butyl-2-methylpiperidine) | 418 | 2.02 |
| 156 | (N-butyl-4-methylpiperazine) | 419 | 1.83 |
| 157 | (N-butylmorpholine) | 406 | 1.89 |
| 158 | HO(CH$_2$)$_3$— | 337 | 2.18 |
| 159 | MeO(CH$_2$)$_3$— | 351 | 2.43 |
| 160 | MeS(CH$_2$)$_3$— | 367 | 2.65 |
| 161 | HO(CH$_2$)$_5$— | 365 | 2.36 |
| 162 | iBu | 335 | 2.73 |
| 163 | 2-MecHex | 375 | 3.01 |
| 164 | (1-cyclohexylethyl) | 389 | 3.15 |
| 165 | Me$_2$N(CH$_2$)$_2$— | 350 | 1.85 |
| 166 | PhSO$_2$(CH$_2$)$_2$— | 447 | 2.53 |
| 167 | EtO$_2$C(CH$_2$)$_3$— | 393 | 2.65 |
| 168 | Bzl | 369 | 2.70 |
| 169 | 2-FPhCH$_2$— | 387 | 2.75 |
| 170 | 2-ClPhCH$_2$— | 403 | 2.90 |
| 171 | 2-BrPhCH$_2$— | 448 | 2.95 |
| 172 | 2-CF$_3$PhCH$_2$— | 437 | 3.02 |

TABLE 12-continued
(continued from Table 11)
| Ex | R¹ | MASS | HPLC rt(min) |
|---|---|---|---|
| 173 | 2-MePhCH₂— | 383 | 2.85 |
| 174 | 2-MeOPhCH₂— | 399 | 2.74 |
| 175 | 2-(2-HOCH₂PhS)PhCH₂— | 507 | 2.92 |
| 176 | 3-FPhCH₂— | 387 | 2.78 |
| 177 | 3-ClPhCH₂— | 403 | 2.94 |
| 178 | 3-IPhCH₂— | 495 | 3.03 |
| 179 | 3-O₂NPhCH₂— | 414 | 2.71 |
| 180 | 3-CF₃PhCH₂— | 437 | 3.03 |
| 181 | 3-MeOPhCH₂— | 399 | 2.71 |
| 182 | 4-ClPhCH₂— | 403 | 2.94 |
| 183 | 4-BrPhCH₂— | 448 | 2.99 |
| 184 | 4-CF₃PhCH₂— | 437 | 3.04 |
| 185 | 4-MePhCH₂— | 383 | 2.86 |
| 186 | 4-tBuPhCH₂— | 425 | 3.21 |
| 187 | 4-MeOPhCH₂— | 399 | 2.67 |
| 188 | 2,3-diMeOPhCH₂— | 429 | 2.67 |
| 189 | 2,4-diMeOPhCH₂— | 429 | 2.73 |
| 190 | 2,6-diFPhCH₂— | 405 | 2.76 |
| 191 | 3,4-diClPhCH₂— | 438 | 3.14 |
| 192 | 2,6-diHOPhCH₂— | 401 | 2.24 |
| 193 | 3,5-diMeOPhCH₂— | 429 | 2.73 |
| 194 | 2,4,6-triMeOPhCH₂— | 459 | 2.83 |
| 195 | 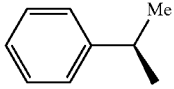 | 383 | 2.81 |
| 196 | 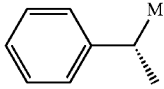 | 383 | 2.80 |
| 197 | Ph₂CH— | 445 | 3.14 |
| 198 | 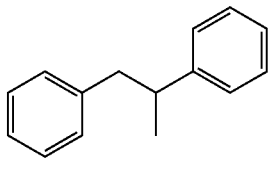 | 459 | 3.15 |
| 199 | 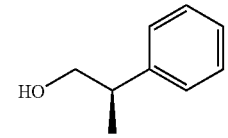 | 399 | 2.54 |
| 200 | 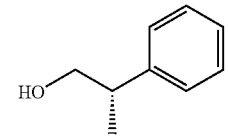 | 399 | 2.54 |
| 201 | 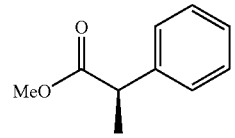 | 427 | 2.85 |
| 202 | 4-MeOPh(cPr)CH— | 439 | 2.89 |
TABLE 13
(continued from Table 12)
| Ex | R¹ | MASS | HPLC rt(min) |
|---|---|---|---|
| 203 | 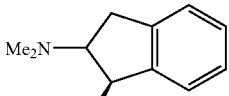 | 438 | 2.46 |
| 204 | 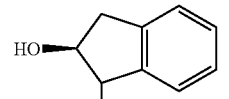 | 411 | 2.66 |
| 205 | 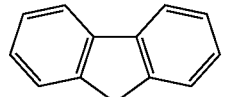 | 443 | 3.23 |
| 206 | 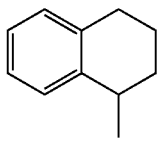 | 409 | 3.02 |
| 207 | 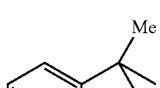 | 397 | 2.86 |
| 208 | 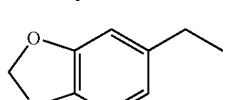 | 413 | 2.66 |
| 209 | 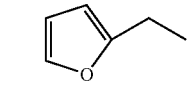 | 359 | 2.54 |
| 210 | 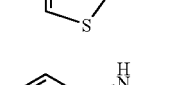 | 375 | 2.66 |
| 211 | 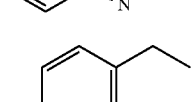 | 409 | 2.19 |
| 212 | 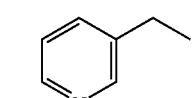 | 370 | 2.00 |
| 213 | 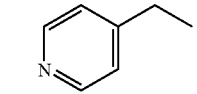 | 370 | 1.89 |
| 214 |  | 370 | 1.82 |

TABLE 13-continued (continued from Table 12)

| Ex | R¹ | MASS | HPLC rt(min) |
|---|---|---|---|
| 215 | 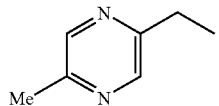 | 385 | 2.28 |
| 216 | Ph(CH₂)₂— | 383 | 2.81 |
| 217 | 2-FPh(CH₂)₂— | 401 | 2.82 |
| 218 | 2-MePh(CH₂)₂— | 397 | 2.93 |
| 219 | 2-MeOPh(CH₂)₂ | 413 | 2.84 |
| 220 | 3-FPh(CH₂)₂ | 401 | 2.85 |
| 221 | 3-ClPh(CH₂)2 | 417 | 3.00 |
| 222 | 3-MePh(CH₂)₂— | 397 | 2.95 |
| 223 | 3-HOPh(CH₂)₂— | 399 | 2.48 |
| 224 | 3-MeOPh(CH₂)₂— | 413 | 2.77 |
| 225 | 4-FPh(CH₂)₂— | 401 | 2.85 |
| 226 | 4-ClPh(CH₂)₂— | 417 | 3.01 |
| 227 | 4-O₂NPh(CH₂)₂— | 428 | 2.76 |
| 228 | 4-MePh(CH₂)₂— | 397 | 2.97 |
| 229 | 4-HOPh(CH₂)₂— | 399 | 2.41 |
| 230 | 4-MeOPh(CH₂)₂— | 413 | 2.76 |
| 231 | 4-PhOPh(CH₂)₂— | 475 | 3.18 |
| 232 | 4-H₂NSO₂Ph(CH₂)₂— | 462 | 2.25 |
| 233 | 2,4-di-ClPh(CH₂)₂— | 452 | 3.19 |
| 234 | 2,5-di-MeOPh(CH₂)₂— | 443 | 2.79 |
| 235 | 3,4-di-ClPh(CH₂)₂— | 452 | 3.17 |
| 236 | 3-Br-4-MeOPh | 492 | 2.90 |
| 237 | 4-HO-3-MeOPh | 429 | 2.43 |
| 238 | 3,4-di-MeOPh | 443 | 2.59 |

TABLE 14

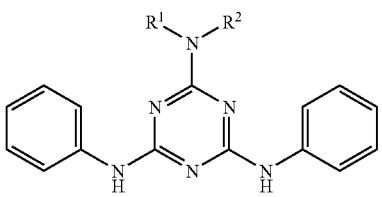

| Ex | R¹ | R² | MASS | HPLC rt(min) |
|---|---|---|---|---|
| 239 | 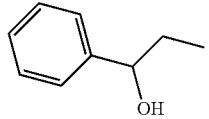 | H | 426 | 2.60 |
| 240 | 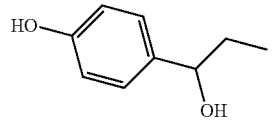 | H | 441 | 2.86 |
| 241 | 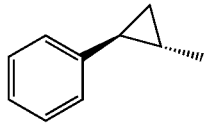 | H | 431 | 3.07 |
| 242 | 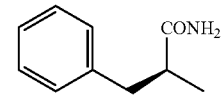 | H | 506 | 2.34 |

TABLE 14-continued

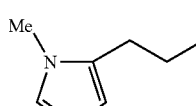

| Ex | R¹ | R² | MASS | HPLC rt(min) |
|---|---|---|---|---|
| 243 | 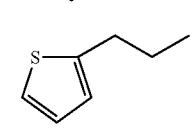 | H | 399 | 2.57 |
| 244 |  | H | 415 | 2.18 |
| 245 | 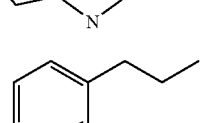 | H | 395 | 2.94 |
| 246 | 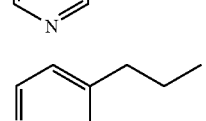 | H | 386 | 2.58 |
| 247 |  | H | 389 | 2.74 |
| 248 | 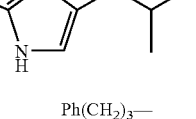 | H | 422 | 2.68 |
| 249 | 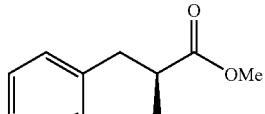 | H | 384 | 1.81 |
| 250 | 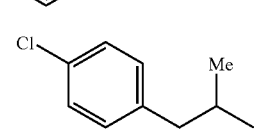 | H | 384 | 1.85 |
| 251 | 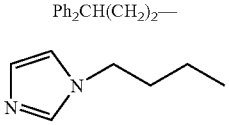 | H | 494 | 2.95 |
| 252 | Ph(CH₂)₃— | H | 397 | 2.92 |
| 253 | Ph₂CH(CH₂)₂— | H | 473 | 3.16 |
| 254 | 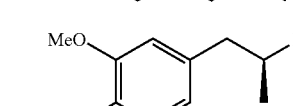 | H | 387 | 1.78 |

TABLE 14-continued

Structure: 4,6-dianilino-1,3,5-triazine with NR¹R² at 2-position

| Ex | R¹ | R² | MASS | HPLC rt(min) |
|---|---|---|---|---|
| 255 | Ph(CH₂)₄— | H | 411 | 3.05 |
| 256 | 3-PhOPhCH₂— | H | 461 | 3.13 |
| 257 | 1,1-bis(4-methoxyphenyl)ethyl | H | 505 | 3.08 |
| 258 | 1-methylindanyl | H | 395 | 2.92 |
| 259 | 1-(1-naphthyl)ethyl | H | 433 | 3.05 |
| 260 | (5-bromothien-2-yl)methyl (ethyl) | H | 454 | 3.00 |
| 261 | imidazo[2,1-b]thiazol-6-ylethyl | H | 415 | 2.08 |
| 262 | 5-chloro-1H-benzimidazol-2-ylethyl | H | 443 | 2.57 |
| 263 | 5-methoxy-1H-benzimidazol-2-ylethyl | H | 439 | 2.36 |
| 264 | 2-ClPh(CH₂)₂— | H | 417 | 2.95 |
| 265 | 1-phenyl-1-(NMe₂)propyl | H | 426 | 2.18 |
| 266 | 1-phenyl-1-(pyrrolidin-1-yl)propyl | H | 452 | 2.16 |
| 267 | 1-phenyl-1-(morpholin-4-yl)propyl | H | 468 | 2.15 |
| 268 | (1-methyl-5-nitroimidazol-2-yl)propyl | H | 432 | 2.33 |
| 269 | 1H-benzimidazol-2-ylpropyl | H | 423 | 2.20 |
| 270 | Me | Me | 307 | 2.41 |
| 271 | Bzl | Me | 383 | 3.08 |
| 272 | NCCH₂— | Me | 332 | 2.59 |
| 273 | EtO₂CCH₂— | Me | 379 | 2.72 |
| 274 | Ph(CH₂)₂— | Me | 397 | 3.14 |

TABLE 15

(continued from Table 14)

| Ex | R¹ | R² | MASS | HPLC rt(min) |
|---|---|---|---|---|
| 275 | 3,4-dimethoxyphenethyl | Me | 457 | 2.84 |

TABLE 15-continued (continued from Table 14)

| Ex | R¹ | R² | MASS | HPLC rt(min) |
|---|---|---|---|---|
| 276 | Me | Et₂N(CH₂)₂— | 392 | 1.87 |
| 277 | Me | (2-SMe-cyclopentyl)N(Me)propyl | 464 | 2.28 |
| 278 | Me | 3-MeS-4-Me-tetrahydrofuran | 409 | 2.81 |
| 279 | cHex | Me | 375 | 3.19 |
| 280 | Me | 2-(pyrrolidin-1-yl)-1-methylcyclohexyl | 444 | 2.38 |
| 281 | Me | 2-(morpholin-4-yl)-1-methylcyclohexyl | 460 | 2.35 |
| 282 | Me | 2-(Me₂N)-1-methylcyclohexyl | 416 | 2.33 |
| 283 | 1-MeN-piperidin-4-yl | Me | 390 | 1.84 |
| 284 | Et | Et | 335 | 2.87 |
| 285 | iPr | Et | 349 | 2.92 |
| 286 | Bzl | Et | 397 | 3.21 |
| 287 | Et₂N(CH₂)₂— | Et | 406 | 2.06 |
| 288 | HO(CH₂)₂— | Et | 351 | 2.31 |
| 289 | cHex | Et | 389 | 3.34 |
| 290 | H₂C=CHCH₂— | 2-(Me₂N)-1-methylcyclohexyl | 444 | 2.60 |
| 291 | Bzl | iPr | 411 | 3.28 |
| 292 | MeO(CH₂)— | iPr | 379 | 2.84 |

TABLE 15-continued (continued from Table 14)

| Ex | R¹ | R² | MASS | HPLC rt(min) |
|---|---|---|---|---|
| 293 | HO(CH₂)₂— | HO(CH₂)₂— | 367 | 1.98 |
| 294 | MeO(CH₂)₂— | MeO(CH₂)₂— | 395 | 2.61 |
| 295 | MeO(CH₂)₂— | (3-methylthio-tetrahydrofuran-4-yl) | 451 | 3.13 |
| 296 | MeO(CH₂)₂— | (2-dimethylamino-cyclohexyl) | 462 | 2.48 |
| 297 | Bu | Bu | 391 | 3.45 |
| 298 | cHex | cHex | 443 | 3.71 |
| 299 | EtO₂CCH₂— | EtO₂CCH₂— | 451 | 2.92 |
| 300 | Bzl | NC(CH₂)₃— | 422 | 3.06 |
| 301 | Bzl | HO(CH₂)₂— | 413 | 2.80 |
| 302 | Bzl | EtO₂CCH₂— | 455 | 3.28 |
| 303 | Bzl | EtO₂C(CH₂)₂— | 469 | 3.28 |
| 304 | Bzl | Bzl | 459 | 3.55 |
| 305 | (2,3-dihydro-1,4-benzodioxin-6-yl)ethyl | cHep | 523 | 3.55 |
| 306 | Me | Pr | 335 | 2.84 |
| 307 | 1-(thiophen-2-yl)ethyl | Me | 403 | 3.17 |
| 308 | 1-phenylethyl | (3-methylquinuclidinyl) | 492 | 2.59 |
| 309 | secBu | secBu | 391 | 3.43 |
| 310 | Pr | Pr | 363 | 3.17 |
| 311 | Pr | Et | 349 | 2.98 |
| 312 | 3,4-dimethoxyphenylpropyl | Me | 457 | 2.84 |
| 313 | 1-benzyl-3-methylpyrrolidin-3-yl | Me | 452 | 0.80 |
| 314 | Me | Me₂N(CH₂)₂— | 364 | 1.40 |

TABLE 16

Structure: 1,3,5-triazine with two PhNH- substituents and one NR¹R² substituent (where R¹-N-R² forms a ring as indicated).

| Ex | R¹R²N- | MASS | HPLC rt(min) |
|---|---|---|---|
| 315 | 3-hydroxy-1-methylazetidin-1-yl (HO-azetidine-N-Me) | 335 | 2.22 |
| 316 | 3-(piperidin-1-yl)azetidin-N-Me | 402 | 2.11 |
| 317 | 3-(4-methylpiperazin-1-yl)azetidin-N-Me | 417 | 2.08 |
| 318 | 3-[4-(2-hydroxyethyl)piperazin-1-yl]azetidin-N-Me | 447 | 2.04 |
| 319 | 3-morpholinoazetidin-N-Me | 404 | 2.12 |
| 320 | pyrrolidin-1-yl (N-Me) | 333 | 2.63 |
| 321 | (2S)-2-(methoxymethyl)pyrrolidin-N-Me | 377 | 2.71 |
| 322 | (S)-methyl pyrrolidine-2-carboxylate-N-Me | 391 | 2.71 |
| 323 | 2-acetamidopyrrolidin-N-Me | 390 | 2.23 |
| 324 | 3-(Boc-amino)pyrrolidin-N-Me | 448 | 2.88 |
| 325 | (3R)-3-hydroxypyrrolidin-N-Me | 349 | 2.22 |
| 326 | 3-hydroxypyrrolidin-N-Me | 349 | 2.23 |
| 327 | methyl 4-hydroxy-1-methylpyrrolidine-3-carboxylate | 407 | 2.27 |
| 328 | 2-methylisoindolin-2-yl | 381 | 3.35 |
| 329 | piperidin-1-yl (N-Me) | 347 | 2.90 |
| 330 | 2-(hydroxymethyl)-1-methylpiperidine | 377 | 2.57 |
| 331 | 2-(2-hydroxyethyl)-1-methylpiperidine | 391 | 2.68 |
| 332 | 1-methylpiperidine-3-carboxamide | 390 | 2.29 |
| 333 | ethyl 1-methylpiperidine-3-carboxylate | 419 | 2.99 |
| 334 | 3-hydroxy-1-methylpiperidine | 363 | 2.38 |
| 335 | 3-(hydroxymethyl)-1-methylpiperidine | 377 | 2.46 |

TABLE 16-continued
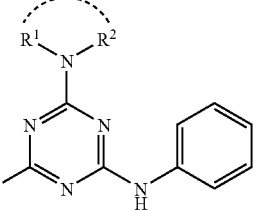
| Ex | | MASS | HPLC rt(min) |
|---|---|---|---|
| 336 | 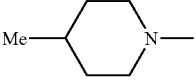 | 361 | 3.12 |
| 337 | 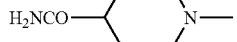 | 390 | 2.18 |
| 338 | 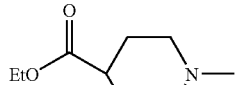 | 419 | 2.95 |
| 339 | 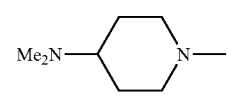 | 390 | 1.98 |
| 340 | 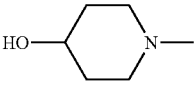 | 363 | 2.32 |
| 341 | 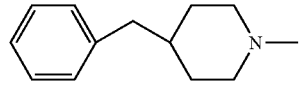 | 437 | 3.50 |
| 342 | 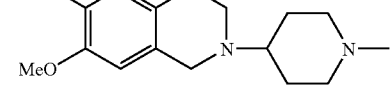 | 538 | 221 |
| 343 | 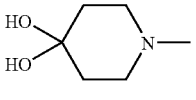 | 379 | 2.47 |
| 344 | 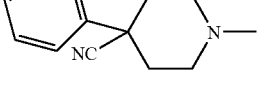 | 448 | 3.28 |
| 345 | 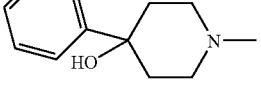 | 439 | 2.93 |
| 346 | 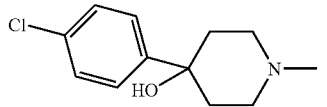 | 473 | 3.16 |
TABLE 16-continued
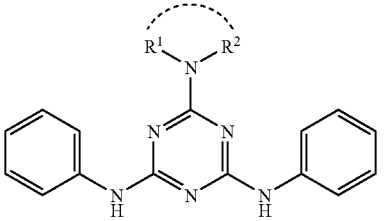
| Ex | | MASS | HPLC rt(min) |
|---|---|---|---|
| 347 |  | 453 | 3.01 |
| 348 | 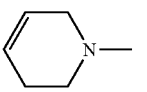 | 345 | 2.93 |
| 349 | 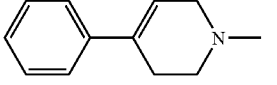 | 421 | 3.50 |
| 350 | 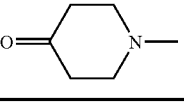 | 361 | 2.46 |
TABLE 17
(continued from Table 16)
| Ex | | MASS | HPLC rt(min) |
|---|---|---|---|
| 351 | 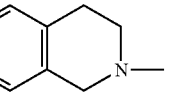 | 395 | 3.35 |
| 352 | 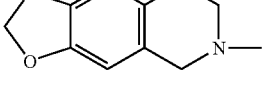 | 439 | 3.31 |
| 353 | 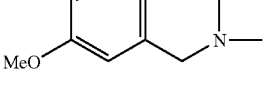 | 455 | 3.02 |
| 354 | 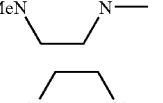 | 362 | 2.00 |
| 355 | 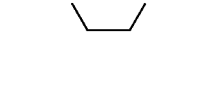 | 390 | 2.08 |

TABLE 17-continued (continued from Table 16)

| Ex | R¹R²N- structure | MASS | HPLC rt(min) |
|---|---|---|---|
| 356 | HOCH2-piperazine-N-Me | 376 | 2.36 |
| 357 | EtOC(O)-piperazine-N-Me | 420 | 2.95 |
| 358 | 2-furoyl-piperazine-N-Me | 442 | 2.76 |
| 359 | iPrNHC(O)CH2-piperazine-N-Me | 447 | 2.25 |
| 360 | MeOCH2CH2-piperazine-N-Me | 406 | 2.10 |
| 361 | HOCH2CH2OCH2CH2-piperazine-N-Me | 436 | 2.03 |
| 362 | HOCH2CH2CH2-piperazine-N-Me | 406 | 2.02 |
| 363 | 2-oxocyclopentyl-piperazine-N-Me | 432 | 2.12 |
| 364 | 2-thioxocyclopentyl-piperazine-N-Me | 462 | 2.41 |
| 365 | 4-(Me2N)-tetrahydrofuran-3-yl-piperazine-N-Me | 461 | 2.02 |
| 366 | 4-thioxo-tetrahydrofuran-3-yl-piperazine-N-Me | 464 | 2.33 |
| 367 | 2-oxocyclohexyl-piperazine-N-Me | 446 | 2.24 |
| 368 | phenyl-piperazine-N-Me | 424 | 3.27 |
| 369 | 2-F-phenyl-piperazine-N-Me | 442 | 3.39 |
| 370 | 2-Cl-phenyl-piperazine-N-Me | 458 | 3.57 |
| 371 | 2-Me-phenyl-piperazine-N-Me | 438 | 3.58 |
| 372 | 2-OMe-phenyl-piperazine-N-Me | 454 | 3.09 |
| 373 | 3-Cl-phenyl-piperazine-N-Me | 458 | 3.57 |
| 374 | 3-CF3-phenyl-piperazine-N-Me | 492 | 3.57 |
| 375 | 3-Me-phenyl-piperazine-N-Me | 438 | 3.37 |
| 376 | 3-OMe-phenyl-piperazine-N-Me | 454 | 3.26 |

TABLE 17-continued
(continued from Table 16)
| Ex | | MASS | HPLC rt(min) |
|---|---|---|---|
| 377 |  | 442 | 3.29 |
| 378 | 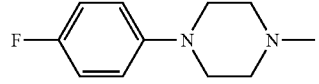 | 454 | 3.01 |
| 379 | 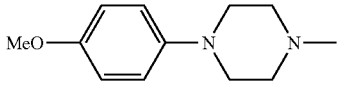 | 463 | 2.91 |
| 380 | 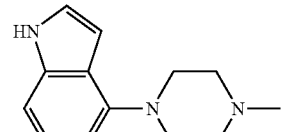 | 438 | 2.37 |
| 381 | 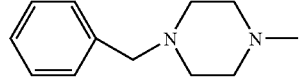 | 482 | 2.36 |
| 382 | 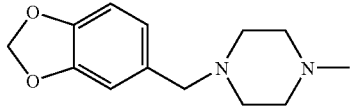 | 514 | 2.99 |
| 383 | 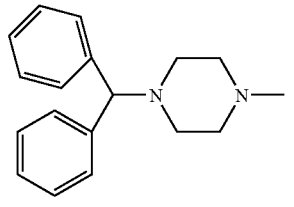 | 425 | 2.23 |
| 384 | 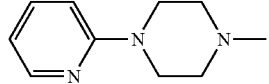 | 349 | 2.56 |
TABLE 18
(continued from Table 17)
| Ex | | MASS | HPLC rt(min) |
|---|---|---|---|
| 385 | 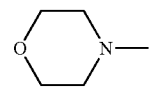 | 377 | 3.00 |
TABLE 18-continued
(continued from Table 17)
| Ex | | MASS | HPLC rt(min) |
|---|---|---|---|
| 386 |  | 365 | 2.97 |
| 387 | 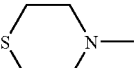 | 361 | 3.04 |
| 388 | 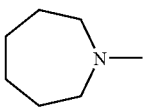 | 376 | 1.97 |
| 389 | 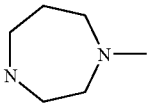 | 409 | 3.15 |
| 390 | 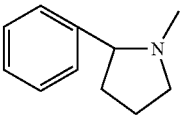 | 423 | 3.30 |
| 391 | 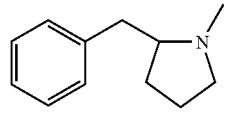 | 409 | 3.22 |
| 392 | 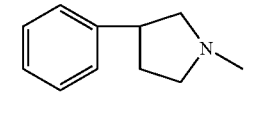 | 423 | 3.26 |
| 393 | 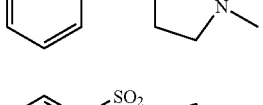 | 473 | 2.71 |
| 394 | 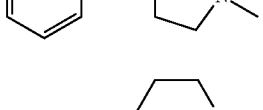 | 391 | 2.56 |
| 395 | 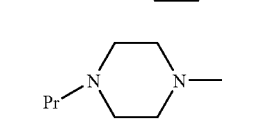 | 390 | 2.13 |
| 396 | 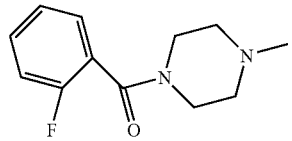 | 470 | 2.95 |

TABLE 18-continued (continued from Table 17)

| Ex | R¹,R² structure | MASS | HPLC rt(min) |
|---|---|---|---|
| 397 |  3-F-C6H4-C(O)-N(piperazine)-Me | 470 | 2.97 |
| 398 | 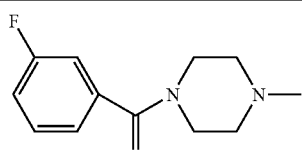 4-F-C6H4-C(O)-N(piperazine)-Me | 470 | 2.95 |
| 399 | 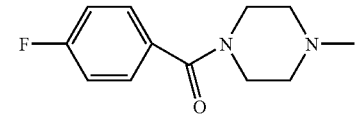 3,4,5-(MeO)3-C6H2-C(O)-N(piperazine)-Me | 542 | 2.84 |
| 400 | HO-CH2CH2-N(piperazine)-Me | 392 | 2.01 |
| 401 | HO-CH2-CH(OH)-CH2-N(piperazine)-Me | 422 | 1.98 |
| 402 | MeO-(CH2)3-N(piperazine)-Me | 420 | 2.11 |
| 403 | quinazolin-4-yl-N(piperazine)-Me | 476 | 2.37 |
| 404 | 2-MeO-C6H4-CH2-N(piperazine)-Me | 468 | 2.42 |
| 405 | 3-MeO-C6H4-CH2-N(piperazine)-Me | 468 | 2.46 |
| 406 | 4-Cl-C6H4-CH2-N(piperazine)-Me | 472 | 2.58 |
| 407 | 4-MeO-C6H4-CH2-N(piperazine)-Me | 468 | 2.40 |
| 408 | furan-2-yl-CH2-N(piperazine)-Me | 428 | 2.30 |
| 409 | pyridin-2-yl-CH2-N(piperazine)-Me | 439 | 2.18 |
| 410 | pyridin-4-yl-CH2-N(piperazine)-Me | 439 | 2.05 |
| 411 | EtO2C-CH2-(3-oxopiperazin-2-yl)-N-Me | 448 | 2.75 |
| 412 | H2NC(O)-pyrrolidin-2-yl-N-Me | 376 | 2.09 |
| 413 | Et-N(piperazine)-Me | 376 | 2.04 |
| 414 | MeO-CH2CH2-N(piperazine)-Me | 406 | 2.10 |
| 415 | HO-(CH2)3-N(piperazine)-Me | 406 | 2.01 |
| 416 | HO-CH2CH2-N(piperazine)-Me | 391 | 2.55 |
| 417 | 3-(hydroxymethyl)-2-methyl-1,2,3,4-tetrahydroisoquinolin-2-yl | 425 | 3.00 |
| 418 | 4-(hydroxymethyl)-1-methylpiperidin-1-yl | 377 | 2.41 |

TABLE 19

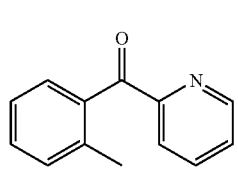

| Ex | R¹ | MASS | HPLC rt(min) |
|---|---|---|---|
| 419 | 2-FPh | 373 | 3.01 |
| 420 | Ph | 355 | 2.86 |
| 421 | 2-ClPh | 389 | 3.23 |
| 422 | 2-BrPh | 434 | 3.25 |
| 423 | 2-MeOPh | 385 | 2.93 |
| 424 | 2-MePh | 369 | 2.84 |
| 425 | 2-EtPh | 383 | 2.98 |
| 426 | 2-PrPh | 397 | 3.15 |
| 427 | 2-iPrPh | 397 | 3.08 |
| 428 | 2-MeSPh | 401 | 3.08 |
| 429 | 2-NCPh | 380 | 2.84 |
| 430 | 2-H₂NCOPh | 398 | 2.83 |
| 431 | 2-HOPh | 371 | 2.64 |
| 432 | 2-HO(CH₂)₂Ph | 399 | 2.59 |
| 433 | 2-EtOPh | 399 | 3.12 |
| 434 | 2-AcPh | 397 | 3.22 |
| 435 | 2-EtO₂CPh | 427 | 3.54 |
| 436 | 2-PhPh | 431 | 3.22 |
| 437 | 2-BzPh | 459 | 3.39 |
| 438 | 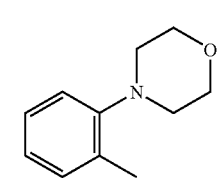 | 460 | 2.85 |
| 439 | 2-PhOPh | 447 | 3.39 |
| 440 | 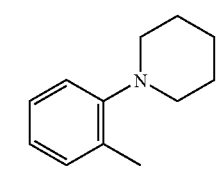 | 440 | 3.10 |
| 441 | 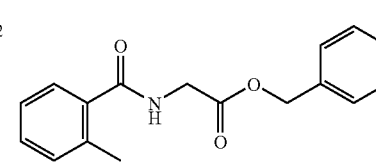 | 438 | 2.84 |
| 442 | 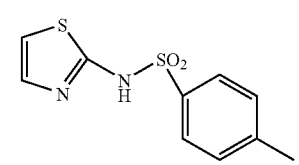 | 546 | 3.15 |
| 443 | 3-FPh | 373 | 3.09 |
| 444 | 3-ClPh | 389 | 3.25 |
| 445 | 3-BrPh | 434 | 3.30 |
| 446 | 3-EtO₂CPh | 427 | 3.18 |
| 447 | 3-MeOPh | 385 | 2.91 |
| 448 | 3-MeSPh | 401 | 3.12 |
| 449 | 3-O₂NPh | 400 | 3.12 |
| 450 | 3-AcPh | 397 | 2.89 |
| 451 | 3-NCPh | 380 | 2.93 |
| 452 | 3-CF₃Ph | 423 | 3.34 |
| 453 | 3-HOPh | 371 | 2.52 |

TABLE 19-continued

| Ex | R¹ | MASS | HPLC rt(min) |
|---|---|---|---|
| 454 | 3-H₂NCOPh | 398 | 2.49 |
| 455 | 3-MeO₂CPh | 413 | 3.05 |
| 456 | 3-HOCH₂Ph | 385 | 2.53 |
| 457 | 3-PhOPh | 447 | 3.41 |
| 458 | 3-BzPh | 459 | 3.25 |
| 459 | 3-PhCH₂OPh | 461 | 3.37 |
| 460 | 4-Ph | 373 | 2.94 |
| 461 | 4-ClPh | 389 | 3.24 |
| 462 | 4-BrPh | 434 | 3.31 |
| 463 | 4-MeOPh | 385 | 2.74 |
| 464 | 4-F₃CPh | 423 | 3.38 |
| 465 | 4-AcPh | 397 | 2.92 |
| 466 | 4-MeO₂CPh | 413 | 3.08 |
| 467 | 4-BuO₂CPh | 455 | 3.50 |
| 468 | 4-O₂NPh | 400 | 3.20 |
| 469 | 4-H₂NSO₂Ph | 434 | 2.50 |
| 470 | 4-PrPh | 397 | 3.30 |
| 471 | 4-iPrPh | 397 | 3.27 |
| 472 | 4-tBuPh | 411 | 3.38 |
| 473 | 4-Me₂NPh | 398 | 2.25 |
| 474 | 4-Et₂NPh | 426 | 2.31 |
| 475 | 4-MeSPh | 401 | 3.09 |
| 476 | 4-HepPH | 453 | 3.83 |
| 477 | 4-HOPh | 371 | 2.37 |
| 478 | 4-H₂NCOPh | 398 | 2.51 |
| 479 | 4-NCPh | 380 | 3.01 |
| 480 | 4-AcNHPh | 412 | 2.46 |

TABLE 20

(continued from Table 19)

| Ex | R¹ | MASS | HPLC rt(min) |
|---|---|---|---|
| 481 | 4-EtO₂CPh | 427 | 3.22 |
| 482 | 4-EtO₂CCH₂Ph | 441 | 2.97 |
| 483 | 4-NCCH₂Ph | 394 | 2.67 |
| 484 | 4-HexPh | 439 | 3.72 |
| 485 | 4-secBuPh | 411 | 3.42 |
| 486 | 4-PhOPh | 447 | 3.33 |
| 487 | 4-BzPh | 459 | 3.29 |
| 488 | 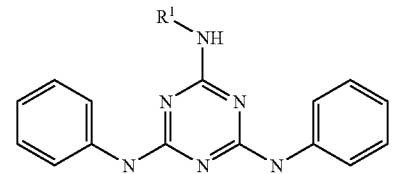 | 517 | 2.58 |
| 489 | 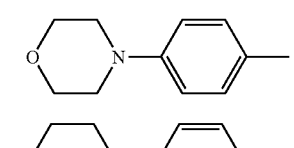 | 440 | 2.61 |
| 490 | 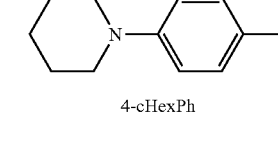 | 438 | 2.30 |
| 491 | 4-cHexPh | 437 | 3.61 |

TABLE 20-continued (continued from Table 19)

| Ex | R¹ | MASS | HPLC rt(min) |
|---|---|---|---|
| 492 | (6-Me-benzothiazol-2-yl)-4-methylphenyl | 502 | 3.82 |
| 493 | 1-(1,2,4-triazol-1-yl)-4-methylphenyl | 422 | 2.75 |
| 494 | 2,3-di-FPh | 391 | 3.15 |
| 495 | 3-HO-2-MePh | 385 | 2.46 |
| 496 | 2,4-di-ClPh | 424 | 3.58 |
| 497 | 4-HO-2-O₂NPh | 416 | 2.83 |
| 498 | 5-HO-2-Me-4-(MeOC(O))Ph | 429 | 2.83 |
| 499 | 3-Cl-5-MePh | 403 | 3.19 |
| 500 | 4-HO-2-MePh | 385 | 2.43 |
| 501 | 2-Me-3-(Cl-benzoyl)Ph | 493 | 3.65 |
| 502 | 4-MeO-2-Me-5-(Et₂NSO₂)Ph | 520 | 3.20 |
| 503 | 2,5-di-MePh | 383 | 3.00 |
| 504 | 2-Me-5-O₂NPh | 414 | 3.05 |
| 505 | 2-HO-5-tPenPh | 441 | 3.30 |
| 506 | 3,4-di-ClPh | 424 | 3.51 |
| 507 | 3-HO-4-O₂NPh | 416 | 2.95 |
| 508 | 3-F-4-MePh | 387 | 3.21 |
| 509 | 2-HO-3-(Et₂NCH₂)-5-MePh | 456 | 2.08 |
| 510 | 4-F-3-O₂NPh | 418 | 3.13 |
| 511 | 3-Cl-4-HOPh | 405 | 2.63 |
| 512 | 3,5-di-F₃CPh | 491 | 3.70 |
| 513 | 3,5-diMeOPh | 415 | 2.96 |
| 514 | 1-naphthyl | 405 | 3.00 |
| 515 | 2-HO-naphthyl | 421 | 2.83 |
| 516 | 6-HO-naphthyl | 421 | 2.63 |
| 517 | 7-HO-naphthyl | 421 | 2.70 |
| 518 | (H₂NSO₂)-naphthyl | 484 | 2.45 |
| 519 | Br-naphthyl | 484 | 3.40 |
| 520 | 3-HO-naphthyl | 421 | 3.10 |
| 521 | 4-HO-naphthyl | 421 | 3.13 |
| 522 | HO-naphthyl | 421 | 2.85 |

TABLE 21

(continued from Table 20)

| Ex | R¹ | MASS | HPLC rt(min) |
|---|---|---|---|
| 523 | quinolinyl | 406 | 3.24 |

TABLE 21-continued
(continued from Table 20)
| Ex | R¹ | MASS | HPLC rt(min) |
|---|---|---|---|
| 524 | 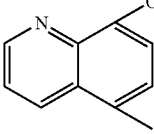 | 422 | 2.18 |
| 525 | 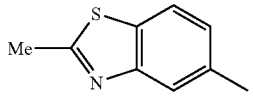 | 426 | 2.98 |
| 526 | 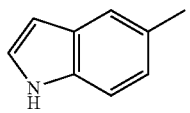 | 394 | 2.53 |
| 527 | 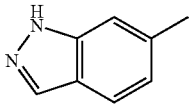 | 395 | 2.64 |
| 528 | 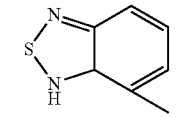 | 413 | 3.43 |
| 529 | 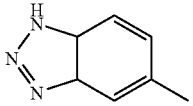 | 396 | 2.57 |
| 530 | 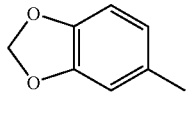 | 399 | 2.78 |
| 531 | 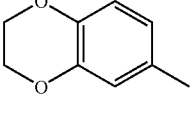 | 413 | 2.73 |
| 532 | 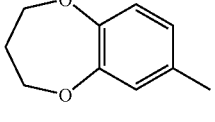 | 427 | 2.83 |
| 533 | 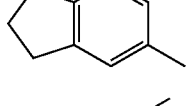 | 395 | 3.17 |
| 534 | 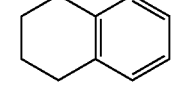 | 409 | 3.15 |
| 535 | 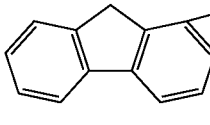 | 443 | 3.42 |
| 536 | 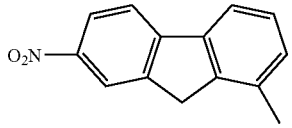 | 488 | 3.43 |
| 537 | 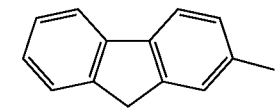 | 443 | 3.49 |
| 538 | 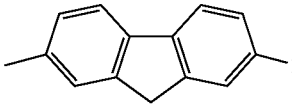 | 522 | 3.82 |
| 539 | 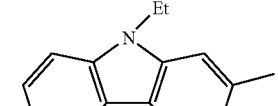 | 472 | 3.26 |
| 540 | 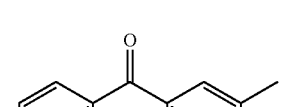 | 474 | 3.20 |
| 541 | 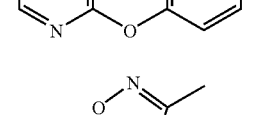 | 346 | 2.83 |
| 542 | 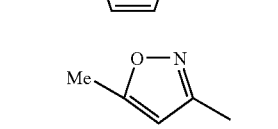 | 360 | 2.41 |
| 543 | 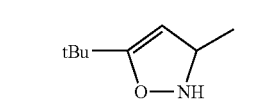 | 402 | 2.70 |
| 544 | 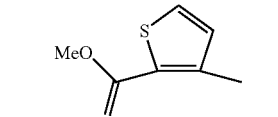 | 419 | 3.39 |
| 545 | 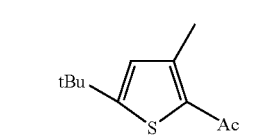 | 459 | 3.72 |
| 546 |  | 487 | 4.01 |

TABLE 21-continued
(continued from Table 20)
| Ex | R¹ | MASS | HPLC rt(min) |
|---|---|---|---|
| 547 | 2-thiazolyl | 362 | 2.49 |
| 548 | 2-benzimidazolyl | 395 | 2.83 |
| 549 | 1,3,4-thiadiazol-2-yl | 363 | 2.40 |
| 550 | 5-(ethylthio)-1,3,4-thiadiazol-2-yl | 423 | 2.69 |
| 551 | ethyl 3-methyl-1H-pyrazole-4-carboxylate | 417 | 3.27 |
| 552 | 3-methyl-1H-pyrazol-5-yl | 345 | 2.36 |
| 553 | 4-cyano-3-methyl-1H-pyrazol-5-yl | 370 | 2.86 |
| 554 | 3-methyl-5-(thiophen-2-yl)-1H-pyrazol-5-yl | 427 | 2.98 |
| 555 | 5-(furan-2-yl)-3-methyl-1H-pyrazol-5-yl | 411 | 2.86 |
TABLE 22
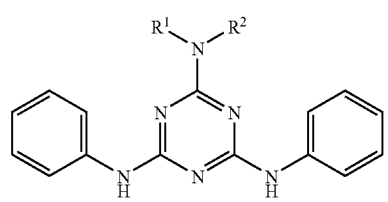
| Ex | R¹ | R² | MASS | HPLC rt(min) |
|---|---|---|---|---|
| 556 | 2-pyridyl | H | 356 | 2.42 |
| 557 | 3-(pentyloxy)-2-pyridyl | H | 442 | 2.91 |
| 558 | 3-hydroxy-2-pyridyl | H | 372 | 2.51 |

TABLE 22-continued

| Ex | R¹ | R² | MASS | HPLC rt(min) |
|---|---|---|---|---|
| 559 | 2-methyl-3-(benzyloxy)pyridin-yl | H | 462 | 2.79 |
| 560 | pyridin-3-yl | H | 356 | 2.35 |
| 561 | 2-methoxy-5-methylpyridin-yl | H | 386 | 2.76 |
| 562 | pyridin-4-yl | H | 356 | 2.41 |
| 563 | pyrimidin-2-yl | H | 357 | 2.28 |
| 564 | 3,5,6-trimethyl-2,3-dihydro-1,2,4-triazin-yl | H | 386 | 2.33 |
| 565 | quinolin-3-yl | H | 406 | 2.93 |
| 566 | 4-benzoylpyridin-3-yl | H | 460 | 2.69 |
| 567 | 4-benzoylpyridazin-yl | H | 461 | 2.57 |
| 568 | 3-MePh | Me | 383 | 3.19 |
| 569 | 1-methylindolin-yl | H | 381 | 3.56 |

TABLE 22-continued
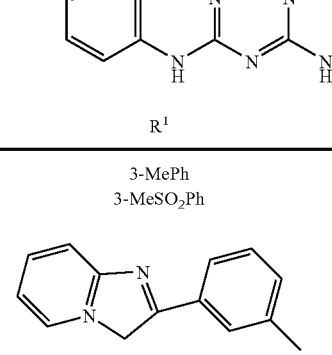
| Ex | R¹ | R² | MASS | HPLC rt(min) |
|---|---|---|---|---|
| 570 | 3-MePh | H | 369 | 3.10 |
| 571 | 3-MeSO₂Ph | H | 433 | 2.79 |
| 572 | 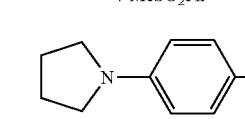 | H | 471 | 2.52 |
| 573 | 4-MeSO₂Ph | H | 433 | 2.80 |
| 574 | 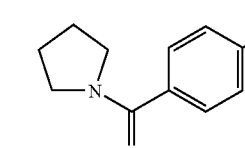 | H | 424 | 2.86 |
| 575 | 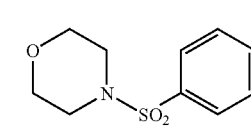 | H | 452 | 2.91 |
| 576 | 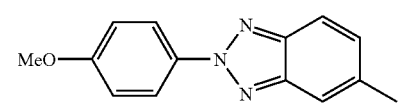 | H | 504 | 2.96 |
| 577 | 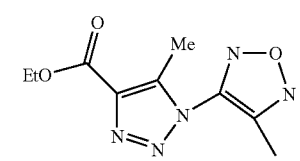 | H | 502 | 3.68 |
| 578 | 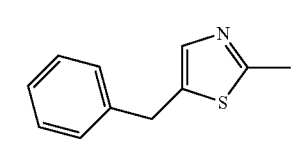 | H | 500 | 1.82 |
| 579 | 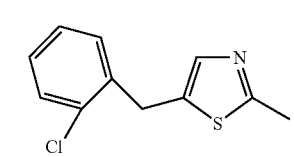 | H | 452 | 2.99 |
| 580 | 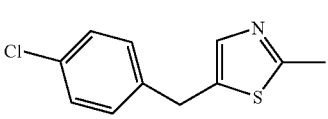 | H | 487 | 3.07 |
| 581 |  | H | 487 | 3.10 |

TABLE 22-continued

| Ex | R¹ | R² | MASS | HPLC rt(min) |
|---|---|---|---|---|
| 582 | 4-Me-C6H4-CH2-(2-methylthiazol-5-yl) | H | 466 | 3.09 |
| 583 | 2-methyl-7-oxo-4,5,6,7-tetrahydrobenzo[b]thiophene-3-carboxylic acid ethyl ester | H | 501 | 2.08 |

TABLE 23

| Ex | R³/R⁴ substituted ArNH— | R⁵/R⁶ substituted ArNH— | MASS | HPLC rt(min) |
|---|---|---|---|---|
| 584 | 2-FPhNH— | 2-FPhNH— | 357 | 2.68 |
| 585 | 2-EtPhNH— | 2-EtPhNH— | 377 | 2.85 |
| 586 | 2-PrPhNH— | 2-PrPhNH— | 405 | 3.06 |
| 587 | 2-MeSPhNH— | 2-MeSPhNH— | 413 | 2.88 |
| 588 | 2-HO(CH2)2PhNH | 2-HO(CH2)2PhNH | 409 | 2.13 |
| 589 | 2-PhPhH | 2-PhPhH | 473 | 3.1 |
| 590 | 2-(pyrrol-1-yl)PhNH | 2-(pyrrol-1-yl)PhNH | 451 | 2.88 |
| 591 | 2-(morpholin-4-yl)PhNH | 2-(morpholin-4-yl)PhNH | 491 | 2.84 |
| 592 | 3-FPhNH— | 3-FPhNH— | 357 | 2.84 |
| 593 | 3-BrPhNH— | 3-BrPhNH— | 479 | 2.84 |
| 594 | 3-MeOPhNH— | 3-MeOPhNH— | 381 | 2.61 |
| 595 | 3-MeSPhNH— | 3-MeSPhNH— | 413 | 2.93 |
| 596 | 3-AcPhNH— | 3-AcPhNH— | 405 | 2.41 |
| 597 | 3-PhOPh | 3-PhOPh | 505 | 3.47 |
| 598 | 3-BzPhNH— | 3-BzPhNH— | 529 | 3.22 |

TABLE 23-continued
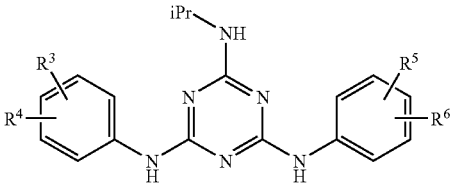
| Ex | R3/R4 | R5/R6 | MASS | HPLC rt(min) |
|---|---|---|---|---|
| 599 | 3-BzlOPhNH— | 3-BzlOPhNH— | 533 | 3.38 |
| 600 | 4-FPhNH— | 4-FPhNH— | 357 | 2.62 |
| 601 | 4-ClPhNH— | 4-ClPhNH— | 389 | 3.15 |
| 602 | 4-BrPhNH— | 4-BrPhNH— | 479 | 3.26 |
| 603 | 4-MeOPhNH— | 4-MeOPhNH— | 381 | 2.42 |
| 604 | 4-PrPhNH— | 4-PrPhNH— | 405 | 3.32 |
| 605 | 4-iPrPhNH— | 4-iPrPhNH— | 405 | 3.25 |
| 606 | 4-tBuPhNH— | 4-tBuPhNH— | 433 | 3.43 |
| 607 | 4-Me$_2$NPhNH— | 4-Me$_2$NPhNH— | 407 | 1.45 |
| 608 | 4-Et$_2$NPhNH— | 4-Et$_2$NPhNH— | 463 | 1.58 |
| 609 | 4-MeSPhNH— | 4-MeSPhNH— | 413 | 2.9 |
| 610 | 4-PhOPhNH— | 4-PhOPhNH— | 505 | 3.31 |
| 611 | 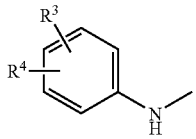 | | 491 | 2.18 |
| 612 | 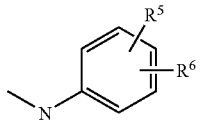 | | 487 | 1.59 |
| 613 | 4-cHexPhNH— | 4-cHexPhNH— | 485 | 3.71 |
| 614 | 2,5-diMePhNH— | 2,5-diMePhNH— | 377 | 2.9 |
| 615 | 3,4-diMeOPhNH | 3,4-diMeOPhNH | 441 | 2.16 |
| 616 | 3-F-4-MePhNH— | 3-F-4-MePhNH— | 385 | 3.1 |
| 617 | 3,5-diMeOPhNH | 3,5-diMeOPhNH | 441 | 2.68 |
| 618 | 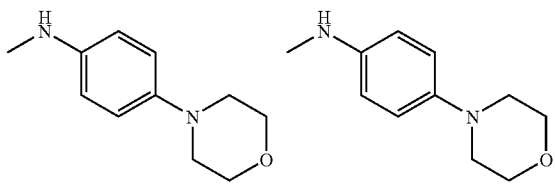 | | 421 | 2.86 |
| 619 | 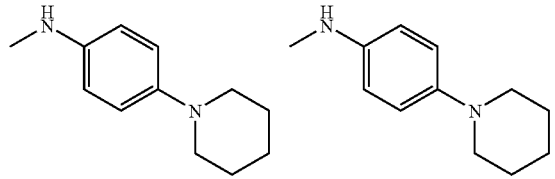 | | 423 | 1.76 |
| 620 | 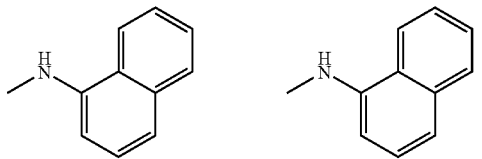 | | 463 | 2.68 |

TABLE 23-continued

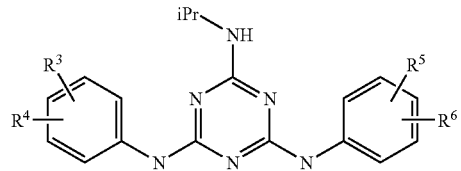

| Ex | R³/R⁴ group | R⁵/R⁶ group | MASS | HPLC rt(min) |
|---|---|---|---|---|
| 621 | 5-methylamino-1H-indole | 5-methylamino-1H-indole | 399 | 2.26 |
| 622 | methylamino-benzo[1,3]dioxole | methylamino-benzo[1,3]dioxole | 409 | 2.37 |

TABLE 24

(continued from Table 23)

| Ex | R³/R⁴ group | R⁵/R⁶ group | MASS | HPLC rt(min) |
|---|---|---|---|---|
| 623 | methylamino-2,3-dihydro-benzo[1,4]dioxine | methylamino-2,3-dihydro-benzo[1,4]dioxine | 437 | 2.35 |
| 624 | methylamino-3,4-dihydro-2H-benzo[b][1,4]dioxepine | methylamino-3,4-dihydro-2H-benzo[b][1,4]dioxepine | 465 | 2.48 |
| 625 | methylamino-indane | methylamino-indane | 401 | 3.11 |
| 626 | methylamino-tetrahydronaphthalene | methylamino-tetrahydronaphthalene | 429 | 3.12 |

TABLE 24-continued (continued from Table 23)

| Ex | R³/R⁴-phenyl-NH group | R⁵/R⁶-phenyl-NH group | MASS | HPLC rt(min) |
|---|---|---|---|---|
| 627 | 4-(methylamino)-2,1,3-benzoxadiazole | 4-(methylamino)-2,1,3-benzoxadiazole | 405 | 3.42 |
| 628 | 1-(methylamino)-9H-fluorene | 1-(methylamino)-9H-fluorene | 497 | 3.5 |
| 629 | 2-(methylamino)-9H-fluorene | 2-(methylamino)-9H-fluorene | 497 | 3.61 |
| 630 | 9-ethyl-3-(methylamino)carbazole | 9-ethyl-3-(methylamino)carbazole | 555 | 3.38 |
| 631 | 5-(methylamino)-2-(4-methoxyphenyl)-2H-benzotriazole | 5-(methylamino)-2-(4-methoxyphenyl)-2H-benzotriazole | 615 | 3.83 |
| 632 | 3-MePhNH— | 3-MePhNH— | 349 | 2.89 |
| 633 | 3-(imidazo[1,2-a]pyridin-2-yl)phenyl-NH(Me) | 3-(imidazo[1,2-a]pyridin-2-yl)phenyl-NH(Me) | 553 | 1.87 |
| 634 | 4-(morpholinosulfonyl)phenyl-NH(Me) | 4-(morpholinosulfonyl)phenyl-NH(Me) | 619 | 2.57 |
| 635 | 4-(pyrrolidin-1-yl)phenyl-NH(Me) | 4-(pyrrolidin-1-yl)phenyl-NH(Me) | 458 | 3.11 |

TABLE 24-continued (continued from Table 23)

| Ex | [R³/R⁴-aryl-NH-Me] | [R⁵/R⁶-aryl-NH-Me] | MASS | HPLC rt(min) |
|---|---|---|---|---|
| 636 | 4-(pyrrolidin-1-ylcarbonyl)-PhNHMe | 4-(pyrrolidin-1-ylcarbonyl)-PhNHMe | 515 | 2.37 |
| 637 | 2-FPhNH— | PhNH— | 339 | 2.54 |
| 638 | 2-ClPhNH— | PhNH— | 355 | 2.72 |
| 639 | 2-BrPhNH— | PhNH— | 399 | 2.74 |
| 640 | 2-NO₂PhNH— | PhNH— | 366 | 2.88 |
| 641 | 2-MeOPhNH— | PhNH— | 351 | 2.54 |
| 642 | 2-MePhNH— | PhNH— | 335 | 2.54 |
| 643 | 2-EtPhNH— | PhNH— | 349 | 2.66 |
| 644 | 2-PrPhNH— | PhNH— | 363 | 2.83 |
| 645 | 2-iPrPhNH— | PhNH— | 363 | 2.8 |
| 646 | 2-tBuPhNH— | PhNH— | 377 | 2.86 |
| 647 | 2-MeSPhNH— | PhNH— | 367 | 2.62 |
| 648 | 2-HO(CH₂)₂PhNH— | PhNH— | 365 | 2.31 |
| 649 | 2-AcPhNH— | PhNH— | 363 | 2.69 |
| 650 | 2-PhPhNH— | PhNH— | 397 | 2.83 |
| 651 | 2-BzPhNH— | PhNH— | 425 | 2.91 |
| 652 | 2-(pyridin-2-ylcarbonyl)-PhNH— | PhNH— | 426 | 2.41 |
| 653 | 2-H₂NCOPhNH— | PhNH— | 413 | 2.99 |
| 654 | 2-(1H-indol-2-yl)-PhNH— | PhNH— | 436 | 2.85 |
| 655 | 2-(1H-pyrrol-1-yl)-PhNH— | PhNH— | 386 | 2.72 |

TABLE 25
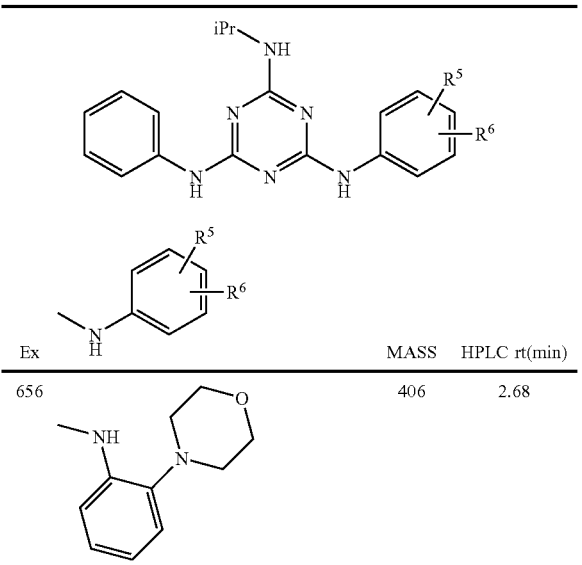
| Ex | | MASS | HPLC rt(min) |
|---|---|---|---|
| 656 | | 406 | 2.68 |
| 657 | | 404 | 2.8 |
| 658 | 3-FPhNH— | 339 | 2.68 |
| 659 | 3-ClPhNH— | 355 | 2.85 |
| 660 | 3-BrPhNH— | 399 | 2.9 |
| 661 | 3-MeOPhNH— | 351 | 2.54 |
| 662 | 3-MeSPhNH— | 367 | 2.74 |
| 663 | 3-NO$_2$PhNH— | 366 | 2.7 |
| 664 | 3-AcPhNH— | 363 | 2.44 |
| 665 | 3-CNPhNH— | 345 | 2.5 |
| 666 | 3-CF$_3$PhNH— | 389 | 2.98 |
| 667 | 3-H$_2$NCOPhNH— | 364 | 2.08 |
| 668 | 3-PhOPhNH— | 413 | 3.05 |
| 669 | 3-BzPhNH— | 425 | 2.86 |
| 670 | 3-BzlOPhNH— | 427 | 3.03 |
| 671 | 4-FPhNH— | 339 | 2.59 |
| 672 | 4-ClPhNH— | 355 | 2.83 |
| 673 | 4-BrPhNH— | 399 | 2.89 |
| 674 | 4-MeOPhNH— | 351 | 2.47 |
| 675 | 4-CF$_3$PhNH— | 389 | 3.05 |
| 676 | 4-AcPhNH— | 363 | 2.5 |
| 677 | 4-NO$_2$PhNH— | 366 | 2.82 |
| 678 | 4-H$_2$NSO$_2$PhNH— | 400 | 2.04 |
| 679 | 4-PrPhNH— | 363 | 3 |
| 680 | 4-iPrPhNH— | 363 | 2.97 |
| 681 | 4-tBuPhNH— | 377 | 3.07 |
| 682 | 4-Me$_2$NPhNH— | 364 | 1.94 |
| 683 | 4-Et$_2$NPhNH— | 392 | 1.96 |
| 684 | 4-MeSPhNH— | 367 | 2.72 |
| 685 | 4-H$_2$NCOPhNH— | 364 | 2.07 |
| 686 | 4-CNPhNH— | 346 | 2.59 |
| 687 | 4-AcNHPhNH— | 378 | 2.16 |
| 688 | 4-CNCH$_2$PhNH— | 360 | 2.29 |
| 689 | 4-PhOPhNH— | 413 | 3.02 |
| 690 | 4-BzPhNH— | 425 | 2.95 |
TABLE 25-continued
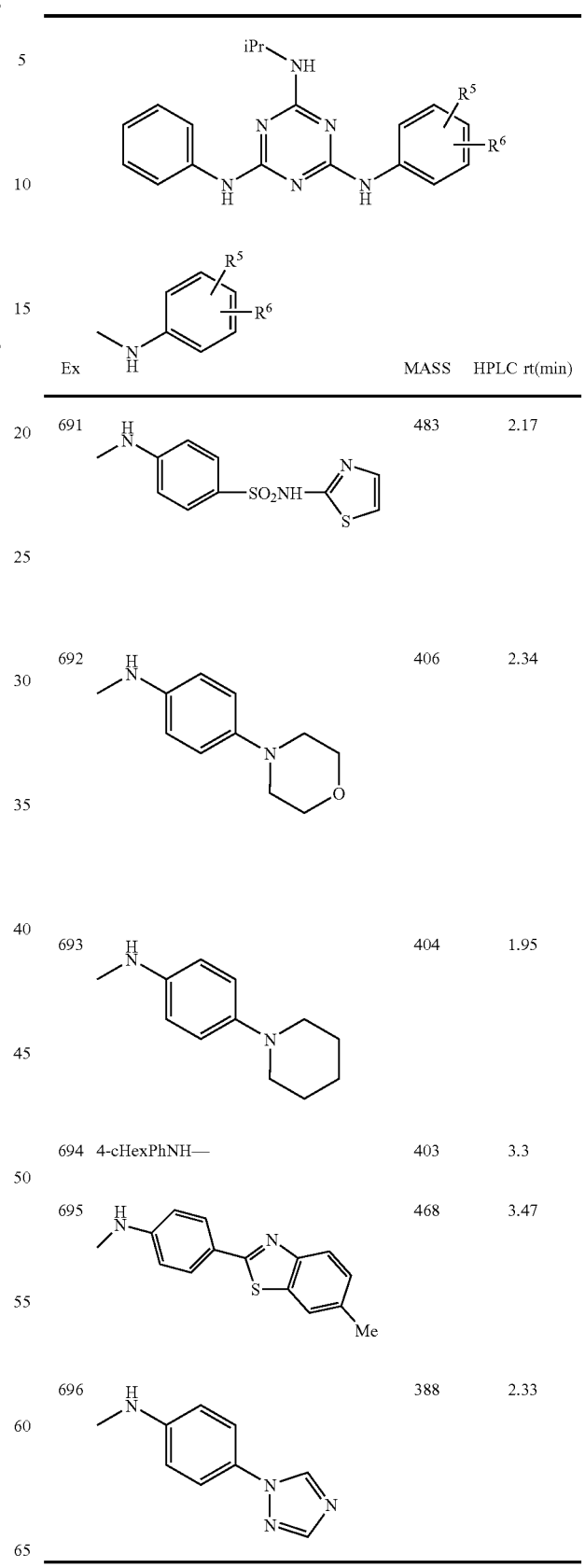
| Ex | | MASS | HPLC rt(min) |
|---|---|---|---|
| 691 | | 483 | 2.17 |
| 692 | | 406 | 2.34 |
| 693 | | 404 | 1.95 |
| 694 | 4-cHexPhNH— | 403 | 3.3 |
| 695 | | 468 | 3.47 |
| 696 | | 388 | 2.33 |

TABLE 26

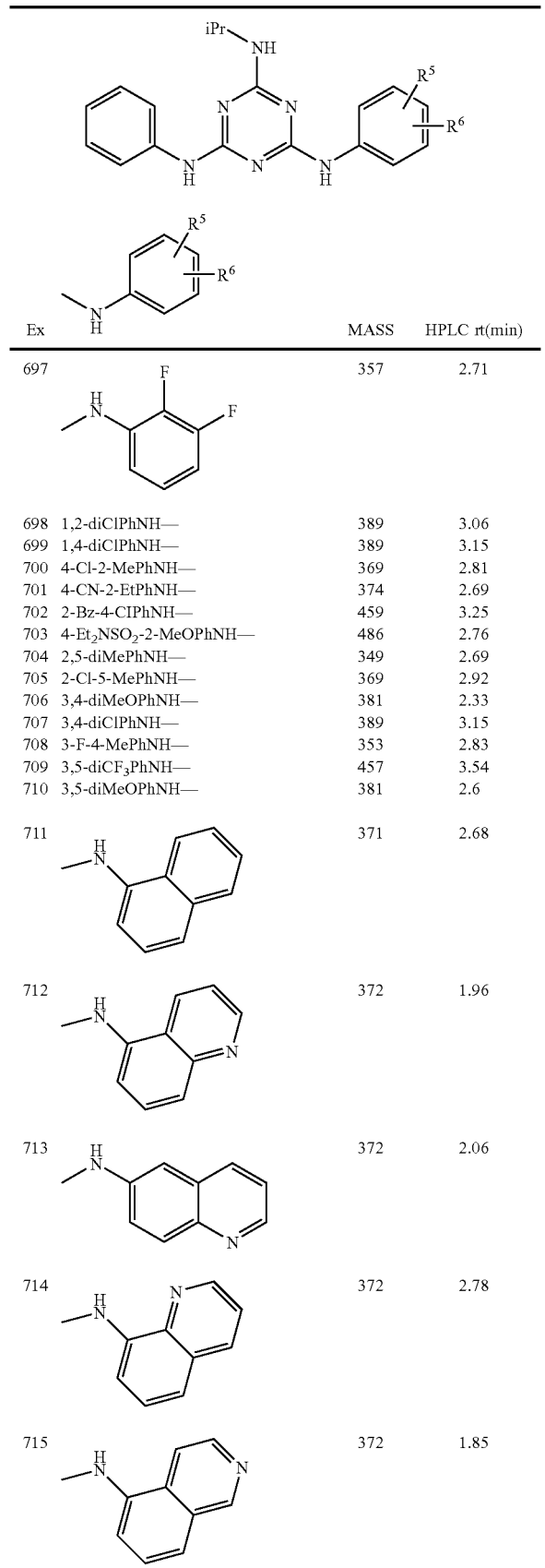

| Ex | | MASS | HPLC rt(min) |
|---|---|---|---|
| 697 | (2,3-diF-PhNH-Me) | 357 | 2.71 |
| 698 | 1,2-diClPhNH— | 389 | 3.06 |
| 699 | 1,4-diClPhNH— | 389 | 3.15 |
| 700 | 4-Cl-2-MePhNH— | 369 | 2.81 |
| 701 | 4-CN-2-EtPhNH— | 374 | 2.69 |
| 702 | 2-Bz-4-ClPhNH— | 459 | 3.25 |
| 703 | 4-Et$_2$NSO$_2$-2-MeOPhNH— | 486 | 2.76 |
| 704 | 2,5-diMePhNH— | 349 | 2.69 |
| 705 | 2-Cl-5-MePhNH— | 369 | 2.92 |
| 706 | 3,4-diMeOPhNH— | 381 | 2.33 |
| 707 | 3,4-diClPhNH— | 389 | 3.15 |
| 708 | 3-F-4-MePhNH— | 353 | 2.83 |
| 709 | 3,5-diCF$_3$PhNH— | 457 | 3.54 |
| 710 | 3,5-diMeOPhNH— | 381 | 2.6 |
| 711 | (1-naphthyl-NHMe) | 371 | 2.68 |
| 712 | (5-quinolinyl-NHMe) | 372 | 1.96 |
| 713 | (6-quinolinyl-NHMe) | 372 | 2.06 |
| 714 | (8-quinolinyl-NHMe) | 372 | 2.78 |
| 715 | (5-isoquinolinyl-NHMe) | 372 | 1.85 |

TABLE 26-continued

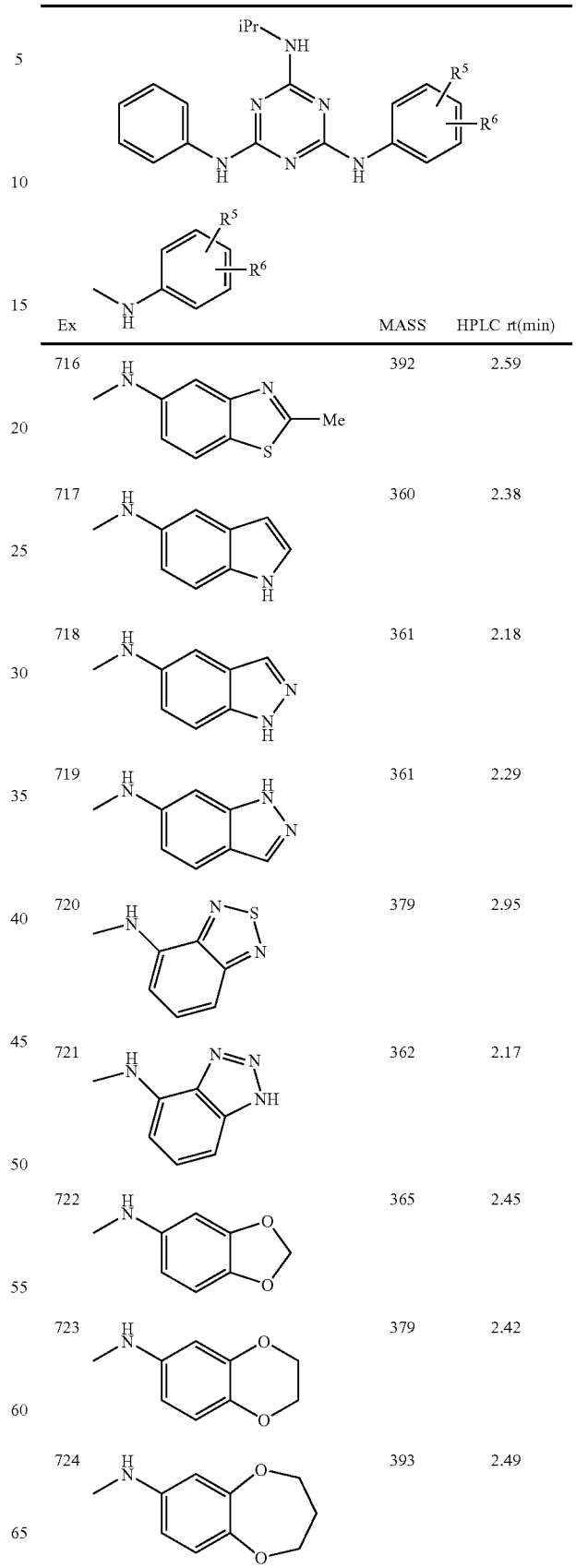

| Ex | | MASS | HPLC rt(min) |
|---|---|---|---|
| 716 | (2-Me-benzothiazol-5-yl-NHMe) | 392 | 2.59 |
| 717 | (indol-5-yl-NHMe) | 360 | 2.38 |
| 718 | (indazol-5-yl-NHMe) | 361 | 2.18 |
| 719 | (indazol-6-yl-NHMe) | 361 | 2.29 |
| 720 | (benzothiadiazol-4-yl-NHMe) | 379 | 2.95 |
| 721 | (benzotriazol-4-yl-NHMe) | 362 | 2.17 |
| 722 | (benzodioxol-5-yl-NHMe) | 365 | 2.45 |
| 723 | (benzodioxin-6-yl-NHMe) | 379 | 2.42 |
| 724 | (benzodioxepin-7-yl-NHMe) | 393 | 2.49 |

TABLE 26-continued
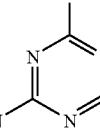
| Ex | | MASS | HPLC rt(min) |
|---|---|---|---|
| 725 | 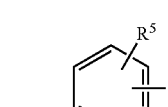 | 361 | 2.86 |
| 726 | 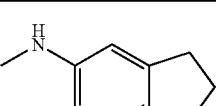 | 375 | 2.85 |
TABLE 27
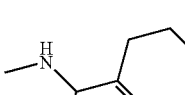
| Ex | | MASS | HPLC rt(min) |
|---|---|---|---|
| 727 | | 390 | 2.44 |
| 728 | | 451 | 3.31 |

TABLE 27-continued

[Structure: triazine core with iPr-NH, phenyl-NH, and NH-aryl(R5,R6) substituents]

[Substituent structure: MeNH-aryl(R5,R6)]

| Ex | | MASS | HPLC rt(min) |
|---|---|---|---|
| 729 | [MeNH-fluorenyl, 1-position] | 409 | 2.98 |
| 730 | [MeNH-fluorenyl, 2-position] | 409 | 3.06 |
| 731 | [MeNH-(9-ethylcarbazolyl)] | 438 | 2.96 |
| 732 | [MeNH-chromeno-pyridinone] | 440 | 2.67 |
| 733 | [MeNH-benzotriazolyl-(4-OMe-phenyl)] | 468 | 3.16 |
| 734 | 3-MePhNH— | 335 | 2.61 |
| 735 | [MeNH-phenyl-imidazo[1,2-a]pyridine] | 437 | 2.02 |
| 736 | [MeNH-phenyl-pyrrolidinyl] | 390 | 2.57 |

TABLE 27-continued

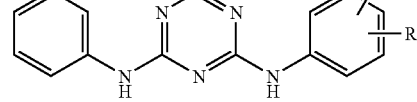

| Ex | | MASS | HPLC rt(min) |
|---|---|---|---|
| 737 | (4-pyrrolidinylcarbonyl-phenyl)methylamino | 418 | 2.37 |
| 738 | (4-morpholinylcarbonyl-phenyl)methylamino | 434 | 2.18 |
| 739 | (4-morpholinylsulfonyl-phenyl)methylamino | 470 | 2.41 |

TABLE 28

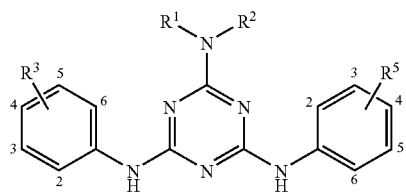

(The numbers 2 to 6 in the formula above represent respective bonding positions of R³ and R⁵.)

| Ex | $R^1\text{-}N\text{-}R^2$ | R³ | R⁵ | Salt/Solvate | DATA |
|---|---|---|---|---|---|
| 740 | N-methyl-2-(pyridin-4-yl N-oxide)ethylamino | H | H | 2HCl 0.4H₂O | m.p.: 161-162<br>¹H-NMR: 3.00-3.20 (2H, m), 3.60-3.80 (2H, m), 7.13-7.20 (2H, m), 7.30-7.45 (4H, m), 7.55-7.90 (6H, m), 8.35-9.00 (3H, m), 10.45-11.00 (2H, m)/DMSO-d₆ |
| 741 | N-methyl-(tetrahydropyran-4-yl)methylamino | H | H | HCl 0.2H₂O | m.p.: 191-193<br>¹H-NMR: 1.15-1.30 (2H, m), 1.55-1.75 (2H, m), 1.80-1.95 (1H, ; m), 3.20-3.35 (4H, m), 3.80-3.92 (2H, m), 7.08-7.22 (2H, m), 7.28-7.44 (4H, m), 7.50-7.85 (4H, m), 8.87 (1H, brs), 10.00-11.05 (2H, m)/DMSO-d₆ |

TABLE 28-continued (The numbers 2 to 6 in the formula above represent respective bonding positions of $R^3$ and $R^5$.)

| Ex | $R^1R^2N-$ | $R^3$ | $R^5$ | Salt/Solvate | DATA |
|---|---|---|---|---|---|
| 742 | (Me)CH-(CH2)3-C(Me)2-OH, N-Me | H | H | HCl | m.p.: 112-113<br>$^1$H-NMR: 1.06 (6H, s), 1.20 (3H, d, J=6.3 Hz), 1.27-1.65 (6H, m), 3.95-4.25 (1H, m), 7.10-7.21 (2H, m), 7.30-7.48 (4H, m), 7.50-7.80 (4H, m), 8.79 (1H, s), 10.20-11.25 (2H, m)/DMSO-d$_6$ |
| 743 | N-Me-CH2-(2-F-pyridin-4-yl) | 4-F | 4-F | HCl | m.p.: 191-192<br>$^1$H-NMR: 4.62 (2H, brs), 7.00-7.38 (6H, m), 7.40-7.80 (4H, m), 8.25 (1H, d, J=4.8 Hz), 8.82 (1H, brs), 9.95-10.40 (2H, m)/DMSO-d$_6$ |
| 744 | N-Me-CH2-(2-F-pyridin-4-yl) | H | 4-F | HCl | m.p.: 175-177<br>$^1$H-NMR: 4.63 (2H, brs), 7.00-7.40 (7H, m), 7.42-7.80 (4H, m), 8.21 (1H, d, J=5.6 Hz), 8.77 (1H, brs), 9.84-10.44 (2H, m)/DMSO-d$_6$ |
| 745 | N-Me-CH2-(2-Me-pyridin-4-yl) | H | 4-F | 2HCl<br>1H$_2$O<br>0.2AcOEt | m.p.: 175-177<br>$^1$H-NMR: 2.74 (3H, s), 4.76 (2H, brs), 6.96-7.15 (2H, m), 7.15-7.29 (2H, m), 7.36 (1H, t, J=7.9 Hz), 7.47 (2H, brs), 7.71 (2H, brs), 7.83 (1H, d, J=6.0 Hz), 7.88 (1H, s), 8.72 (1H, d, J=6.0 Hz), 8.90 (1H, brs), 10.07 (1H, brs), 10.31 (1H, brs)/DMSO-d$_6$ |
| 746 | N-Me-CH2-(2-CH2OH-pyridin-4-yl) | H | 4-F | 2HCl<br>1H$_2$O<br>0.1AcOEt | m.p.: 188-190<br>$^1$H-NMR: 4.81 (2H, brs), 4.89 (2H, s), 6.97-7.16 (2H, m), 7.16-7.30 (2H, m), 7.31-7.40 (1H, m), 7.45 (2H, brs), 7.71 (2H, brs), 7.90 (1H, d, J=5.9 Hz), 8.00 (1H, s), 8.76 (1H, d, J=5.9 Hz), 9.06 (1H, brs), 10.19 (1H, brs), 10.49 (1H, brs)/DMSO-d$_6$ |
| 747 | N-Me-CH2-(2-NH2-pyridin-4-yl) | H | 4-F | 2.1HCl<br>1.5H$_2$O | m.p.: 164-199<br>$^1$H-NMR: 4.55 (2H, brs), 6.85 (1H, d, J=6.9 Hz), 6.93 (1H, s), 6.98-7.15 (2H, m), 7.15-7.30 (2H, m), 7.30-7.40 (1H, m), 7.53 (2H, brs), 7.71 (2H, brs), 7.95 (1H, d, J=6.9 Hz), 8.14 (2H, brs), 8.80 (1H, brs), 10.09 (1H, brs), 10.30 (1H, brs), 13.91 (1H, brs)/DMSO-d$_6$ |

TABLE 29

(continued from Table 28)

| 748 | N-Me-CH2-(2-NHMe-pyridin-4-yl) | H | 4-F | 1.9HCl<br>1.5H$_2$O | m.p.: 153-155<br>$^1$H-NMR: 2.95 (3H, d, J=4.4 Hz), 4.55 (2H, brs), 6.84 (1H, d, J=6.8 Hz), 6.98 (1H, s), 6.92-7.13 (3H, m), 7.13-7.22 (1H, m), 7.22-7.29 (1H, m), 7.29-7.38 (1H, m), 7.56 (2H, brs), 7.72 (2H, brs), 7.99 (1H, d, J=6.8 Hz), 8.65 (1H, brs), 8.99 (1H, brs), 9.95 (1H, brs), 10.11 (1H, brs), 13.60 (1H, brs)/DMSO-d$_6$ |
| 749 | N-Me-CH2-(2-NHEt-pyridin-4-yl) | H | 4-F | 1.9HCl<br>1.5H$_2$O | m.p.: 149-151<br>$^1$H-NMR: 1.18 (3H, t, J=7.3 Hz), 3.28-3.46 (2H, m), 4.54 (2H, brs), 6.83 (1H, d, J=6.3 Hz), 6.90-7.13 (3H, m), 7.13-7.29 (2H, m), 7.29-7.39 (1H, m), 7.56 (2H, brs), 7.72 (2H, brs), 7.87 (1H, d, J=6.3 Hz), 8.56 (1H, brs), 8.90 (1H, brs), 9.89 (1H, brs), 10.12 (1H, brs), 13.59 (1H, brs)/DMSO-d$_6$ |
| 750 | N-Me-CH2-(2-NHPr-pyridin-4-yl) | H | 4-F | 2HCl<br>1.5H$_2$O | m.p.: 149-150<br>$^1$H-NMR: 0.92 (3H, t, J=7.4 Hz), 1.50-1.66 (2H, m), 3.23-3.40 (2H, m), 4.54 (2H, brs), 6.82 (1H, d, J=6.9 Hz), 6.94-7.14 (3H, m), 7.14-7.29 (2H, m), 7.29-7.40 (1H, m), 7.56 (2H, brs), 7.72 (2H, brs), 7.82-7.92 (1H, m), 8.60 (1H, brs), 8.94 (1H, brs), 9.94 (1H, brs), 10.07 (1H, brs), 13.62 (1H, brs)/DMSO-d$_6$ |

TABLE 29-continued (continued from Table 28)

| No. | Structure | | | Salt | Data |
|---|---|---|---|---|---|
| 751 | HN-CH2-pyridyl-OEt (4-OEt) | H | 4-F | 1.9HCl 0.5H$_2$O | m.p.: 155-157<br>$^1$H-NMR: 1.31 (3H, t, J=6.8 Hz), 4.31 (2H, q, J=6.8 Hz), 4.59 (2H, brs), 6.87 (1H, s), 7.03 (1H, d, J=5.2 Hz), 7.07-7.33 (4H, m), 7.33-7.43 (1H, m), 7.50 (2H, brs), 7.67 (2H, brs), 8.14 (1H, d, J=5.2 Hz), 9.29 (1H, brs), 10.47 (1H, brs), 10.83 (1H, brs)/DMSO-d$_6$ |
| 752 | HN-CH2-pyridyl-OMe | H | 4-F | 1.9HCl 1.1H$_2$O | m.p.: 145-147<br>$^1$H-NMR: 3.87 (3H, s), 4.58 (2H, brs), 6.89 (1H, brs), 6.97-7.34 (5H, m), 7.34-7.43 (1H, m), 7.50 (2H, brs), 7.67 (2H, brs), 8.16 (1H, d, J=5.4 Hz), 9.32 (1H, brs), 10.50 (1H, brs), 10.86 (1H, brs)/DMSO-d$_6$ |
| 753 | HN-CH2-pyridyl-OMe | H | 4-F | free 0.1H$_2$O | m.p.: 134-136<br>$^1$H-NMR: 3.82 (3H, s), 4.44 (2H, d, J=6.3 Hz), 6.79 (1H, d, J=6.9 Hz), 6.94 (1H, t, J=7.4 Hz), 7.03-7.18 (2H, m), 7.20-7.30 (2H, m), 7.60 (1H, brs), 7.66-7.87 (6H, m), 8.16 (1H, s), 8.98-9.26 (2H, m)/DMSO-d$_6$ |
| 754 | HN-CH2-pyridyl-F | H | 4-F | 1.8HCl 0.4H$_2$O | m.p.: 112-114<br>$^1$H-NMR: 4.63 (2H, brs), 7.00-7.33 (4H, m), 7.33-7.90 (7H, m), 8.00 (1H, dd, J=7.8 Hz, 15.6 Hz), 9.36 (1H, brs), 10.52 (1H, brs), 10.97 (1H, brs)/DMSO-d$_6$ |
| 755 | HN-CH2-pyridyl-Me | H | 4-F | 2HCl H$_2$O | m.p.: 139-140<br>$^1$H-NMR: 2.80 (3H, s), 4.96 (2H, d, J=4.9 Hz), 6.97-7.24 (3H, m), 7.24-7.32 (1H, m), 7.32-7.41 (1H, m), 7.41-7.60 (2H, m), 7.60-7.88 (4H, m), 8.36 (1H, t, J=6.5 Hz), 8.89 (1H, brs), 10.19 (1H, brs), 10.45 (1H, brs)/DMSO-d$_6$ |
| 756 | HN-CH2-pyridyl-Me (4-Me) | H | 4-F | 2HCl H$_2$O 0.3AcOEt | m.p.: 147-148<br>$^1$H-NMR: 2.56 (3H, s), 4.90 (2H, d, J=5.4 Hz), 6.79-7.30 (4H, m), 7.30-7.41 (1H, m), 7.41-7.81 (5H, m), 7.85 (1H, s), 8.71 (1H, d, J=5.8 Hz), 8.89 (1H, brs), 10.25 (1H, brs), 10.46 (1H, brs)/DMSO-d$_6$ |

TABLE 30

(continued from Table 29)

| No. | Structure | | | Salt | Data |
|---|---|---|---|---|---|
| 757 | HN-CH2-pyridyl-CH2OH | H | 4-F | 1.95HCl | m.p.: 146-148<br>$^1$H-NMR: 4.79 (2H, s), 4.81 (2H, s), 6.90-7.28 (4H, m), 7.28-7.39 (1H, m), 7.40-7.80 (6H, m), 8.15-8.33 (1H, m), 7.95 (1H, brs), 8.48 (1H, brs), 9.85 (1H, brs), 9.98 (1H, brs)/DMSO-d$_6$ |
| 758 | HN-CH2-pyridyl-NHBoc | H | 4-F | 2HCl 0.5H$_2$O | m.p.: 160-162<br>$^1$H-NMR: 1.45 (9H, s), 4.57 (2H, brs), 6.96-7.32 (6H, m), 7.32-7.57 (3H, m), 7.67 (2H, d, J=7.8 Hz), 7.80 (1H, t, J=7.5 Hz), 9.18 (1H, brs), 9.94 (1H, brs), 10.47 (1H, brs), 10.86 (1H, brs)/DMSO-d$_6$ |
| 759 | HN-CH2-pyridyl-OMe | H | 4-F | 1.9HCl 0.9H$_2$O 0.1AcOEt | m.p.: 120-122<br>$^1$H-NMR: 3.87 (3H, s), 4.60 (2H, brs), 6.75 (1H, d, J=7.8 Hz), 6.90-7.35 (5H, m), 7.40 (1H, t, J=7.4 Hz), 7.50 (2H, brs), 7.61-7.80 (3H, m), 9.34 (1H, brs), 10.59 (1H, brs), 11.00 (1H, brs)/DMSO-d$_6$ |
| 760 | HN-CH2-pyridyl-OiPr | H | 4-F | 2.4HCl H$_2$O | m.p.: 152-154<br>$^1$H=NMR: 1.33 (2H, d, J=6.3 Hz), 4.60 (2H, brs), 5.23 (1H, hep, J=6.3 Hz), 6.65 (1H, d, J=8.3 Hz), 6.95 (1H, d, J=6.9 Hz), 7.01-7.33 (4H, m), 7.33-7.58 (3H, m), 7.58-7.80 (3H, m), 9.22 (1H, brs), 10.53 (1H, brs), 10.87 (1H, brs)/DMSO-d$_6$ |
| 761 | HN-CH2-pyrimidyl | H | 4-F | 2HCl 0.3H$_2$O 0.1AcOEt | m.p.: 161-163<br>$^1$H-NMR: 4.79 (2H, brs), 7.00-7.45 (6H, m), 7.48 (2H, brs), 7.71 (2H, brs), 8.86 (2H, d, J=4.9 Hz), 9.54 (1H, brs), 10.57 (1H, brs), 11.17 (1H, brs)/DMSO-d$_6$ |

TABLE 30-continued (continued from Table 29)

| 762 | [structure: HN(Me)CH2-pyrimidine-2-NH2] | H | 4-F | 1.95HCl 1.5H$_2$O | m.p.: 158-160<br>$^1$H-NMR: 4.57 (2H, brs), 6.97 (1H, d, J=6.4 Hz), 7.01-7.32 (4H, m), 7.32-7.42 (1H, m), 7.71 (2H, brs), 7.95 (2H, brs), 8.41 (1H, d, J=6.4 Hz), 8.53 (2H, brs), 8.84 (1H, brs), 10.13 (1H, brs), 10.40 (1H, brs)/DMSO-d$_6$ |
| --- | --- | --- | --- | --- | --- |
| 763 | [structure: HN(Me)CH2-C6H4-CH2OH (meta)] | H | 4-F | HCl | m.p.: 140-141<br>$^1$H-NMR: 4.49 (2H, s), 4.58 (2H, brs), 7.04-7.27 (5H, m), 7.27-7.42 (4H, m), 7.59 (2H, brs), 7.66 (2H, brs), 9.00 (1H, brs), 10.30 (1H, brs), 10.52 (1H, brs)/DMSO-d$_6$ |
| 764 | [structure: HN(Me)CH2-furan-2-yl] | H | 4-F | HCl 0.5H$_2$O | m p.: 144-148<br>$^1$H-NMR: 4.57 (2H, brs), 6.26-6.48 (2H, m), 7.05-7.20 (3H, m), 7.30-7.40 (2H, m), 7.50-7.80 (5H, m), 8.79 (1H, brs), 9.95-10.70 (2H, m)/DMSO-d$_6$ |
| 765 | [structure: HN(Me)CH2-thiazol-4-yl] | H | 4-F | 1.9HCl H$_2$O | m.p.: 124-125<br>$^1$H-NMR: 4.74 (2H, brs), 7.04-7.28 (3H, m), 7.28-7.45 (2H, m), 7.45-8.00 (5H, m), 9.17 (1H, s), 9.40 (1H, brs), 10.64 (1H, brs), 11.06 (1H, brs)/DMSO-d$_6$ |
| 766 | [structure: HN(Me)CH2-thiazol-2-yl] | H | 4-F | 2HCl | m.p.: 122-123<br>$^1$H-NMR: 4.86 (2H, brs), 7.00-7.17 (2H, m), 7.17-7.24 (1H, m), 7.24-7.32 (1H, m), 7.32-7.42 (1H, m), 7.57 (2H, brs), 7.62-7.76 (3H, m), 7.80 (1H, d, J=3.4 Hz), 9.02 (1H, brs), 10.20 (1H, brs), 10.39 (1H, brs)/DMSO-d$_6$ |
| 767 | [structure: HN(Me)CH2-triazole-N-CH2-C6H4-OMe] | H | 4-F | free | m.p.: 214-215<br>$^1$H-NMR: 3.69 (3H, s), 4.69 (2H, d, J=6.4 Hz), 5.35 (2H, s), 6.84 (2H, d, J=8.5 Hz), 6.90-6.98 (1H, m), 6.98-7.13 (3H, m), 7.18 (2H, d, J=8.5 Hz), 7.77 (2H, brs), 7.87 (1H, s), 9.09 (1H, s), 9.13 (1H, s)/DMSO-d$_5$ |

TABLE 31

(continued from Table 30)

| 768 | [structure: HN(Me)CH2-tetrazole] | H | 4-F | HCl | m.p.: 209-211<br>$^1$H-NMR: 4.86 (2H, brs), 6.95-7.17 (3H, m), 7.17-7.30 (2H, m), 7.30-7.40 (1H, m), 7.49 (2H, brs), 7.69 (2H, brs), 8.76 (1H, brs), 10.15 (1H, brs), 10.36 (1H, brs)/DMSO-d$_6$ |
| --- | --- | --- | --- | --- | --- |
| 769 | [structure: HN(Me)CH2-benzothiazol-2-yl] | H | 4-F | 1.8HCl 0.4H$_2$O | m.p.: 212-214<br>$^1$H-NMR: 4.99 (2H, brs), 6.92-7.33 (4H, m), 7.33-7.47 (2H, m), 7.47-7.60 (3H, m), 7.69 (2H, brs), 8.01 (1H, d, J=7.9 Hz), 8.09 (1H, d, J=7.9 Hz), 9.38 (1H, brs), 10.38 (1H, brs), 10.68 (1H, brs)/DMSO-d$_6$ |
| 770 | [structure: HN(Me)CH2-CN] | H | 4-F | HCl 0.5H$_2$O | mp.: 160-162<br>$^1$H-NMR: 4.35 (2H, d, J=4.9 Hz), 7.02-7.10 (1H, m), 7.16 (2H, t, J=7.8 Hz), 7.32 (2H, t, J=7.8 Hz), 7.72 (4H, brs), 8.28 (1H, brs), 9.93 (2H, brs),/DMSO-d$_6$ |
| 771 | MeO(CH$_2$)$_2$NH— | H | 4-F | HCl | m.p.: 179-181<br>$^1$H-NMR: 3.29 (3H, s), 3.40-3.60 (4H, m), 7.10-7.25 (3H, m), 7.26-7.42 (2H, m), 7.50-7.84 (4H, m), 8.60 (1H, brs), 10.15-11.00 (2H, m)/DMSO-d$_6$ |
| 772 | [structure: HN(Me)CH2-1,3-dioxolan-2-yl] | H | 4-F | 1.3HCl 0.2H$_2$O | m.p.: 160-162<br>$^1$H-NMR: 3.56 (2H, s), 3.77-3.90 (2H, m), 3.90-4.05 (2H, m), 5.06 (1H, s), 7.07-7.27 (3H, m), 7.27-7.44 (2H, m), 7.64 (4H, brs), 8.73 (1H, brs), 10.47 (1H, brs), 10.77 (1H, brs)/DMSO-d$_6$ |
| 773 | HO(CH$_2$)$_2$NH— | H | 4-F | HCl | m.p.: 209-211<br>$^1$H-NMR 3.38-3.48 (2H, m), 3.58 (2H, t, J=5.4 Hz), 4.16 (1H, brs), 7.05-7.26 (3H, m), 7.27-7.43 (2H, m), 7.48-7.80 (4H, m), 8.45 (1H, brs), 10.05-10.75 (2H, m)/DMSO-d$_6$ |

TABLE 31-continued (continued from Table 30)

| 774 | HO(CH$_2$)$_3$NH— | H | 4-F | HCl 0.1H$_2$O | m.p.: 188-189<br>$^1$H-NMR: 1.65-1.80 (2H, m), 3.37-3.56 (4H, m), 4.15 (1H, brs), 7.05-7.26 (3H, m), 7.27-7.43 (2H, m), 7.45-7.85 (4H, m), 8.57 (1H, brs), 10.05-10.75 (2H, m)/DMSO-d$_6$ |
|---|---|---|---|---|---|
| 775 | HO(CH$_2$)$_4$NH— | H | 4-F | HCl | m.p.: 185-186<br>$^1$H-NMR: 1.43-1.53 (2H, m), 1.55-1.65 (2H, m), 3.30-3.48 (4H, m), 4.04 (1H, brs), 7.05-7.26 (3H, m), 7.27-7.42 (2H, m), 7.50-7.80 (4H, m), 8.58 (1H, brs), 9.95-10.75 (2H, m)/DMSO-d$_6$ |
| 776 | HO(CH$_2$)$_5$NH— | H | 4-F | HCl | m.p.: 178-180<br>$^1$H-NMR: 1.34-1.50 (4H, m), 1.53-1.60 (2H, m), 3.30-3.42 (4H, m), 4.00 (1H, brs), 7.07-7.24 (3H, m), 7.33-7.40 (2H, m), 7.50-7.80 (4H, m), 8.58 (1H, brs), 10.05-10.75 (2H, m)/DMSO-d$_6$ |
| 777 | HO(CH$_2$)$_2$O(CH$_2$)$_2$NH— | H | 4-F | HCl | m.p.: 141-142<br>$^1$H-NMR: 3.43-3.60 (8H, m), 3.92 (1H, brs), 7.05-7.25 (3H, m), 7.27-7.43 (2H, m), 7.50-7.80 (4H, m), 8.37 (1H, brs), 9.95-10.60 (2H, m)/DMSO-d$_6$ |
| 778 | ![structure: HN-CH(Me)-CH$_2$OH, (S)] | H | 4-F | HCl | m.p.: 192-194<br>$^1$H-NMR: 1.17 (3H, d, J=6.9 Hz), 3.47 (2H, d, J=5.4 Hz), 4.07 (1H, brs), 7.05-7.28 (3H, m), 7.28-7.45 (2H, m), 7.66 (4H, brs), 8.56 (1H, brs), 10.45 (1H, brs), 10.84 (1H, brs)/DMSO-d$_6$ |
| 779 | ![structure: HN-CH(Me)-CH$_2$OH, (R)] | H | 4-F | HCl | m.p.: 193-195<br>$^1$H-NMR: 1.17 (3H, d, J=6.9 Hz), 3.47 (2H, d, J=5.4 Hz), 4.07 (1H, brs), 7.05-7.28 (3H, m), 7.28-7.45 (2H, m), 7.66 (4H, brs), 8.53 (1H, brs), 10.43 (1H, brs), 10.80 (1H, brs)/DMSO-d$_5$ |

TABLE 32

(continued from Table 31)

| 780 | ![structure: HN-CH(Et)-CH$_2$OH] | H | 4-F | HCl | m.p.: 199-201<br>$^1$H-NMR: 0.92 (3M, d, J=7.2 Hz), 1.42-1.58 (1H, m), 1.58-1.74 (1H, m), 3.50 (2H, d, J=5.4 Hz), 3.91 (1H, brs), 7.05-7.28 (3M, m), 7.28-7.45 (2H, m), 7.66 (4H, brs), 8.58 (1H, brs), 10.46 (1H, brs), 10.88 (1H, brs)/DMSO-d$_6$ |
|---|---|---|---|---|---|
| 781 | ![structure: HN-CH(Et)-CH$_2$OH] | H | 4-F | HCl | m.p.: 199-201<br>$^1$H-NMR: 0.92 (3M, d, J=6.8 Hz), 1.41-1.58 (1H, m), 1.58-1.75 (1H, m), 3.50 (2H, d, J=4.9 Hz), 3.91 (1H, brs), 7.05-7.29 (3M, m), 7.29-7.47 (2H, m), 7.66 (4H, brs), 8.50 (1H, brs), 10.41 (1H, brs), 10.77 (1H, brs)/DMSO-d$_6$ |
| 782 | ![structure: HN-CH(iPr)-CH$_2$OH] | H | 4-F | HCl | m.p.: 205-207<br>$^1$H-NMR: 0.95 (6H, d, J=6.3 Hz), 1.87-2.04 (1H, m), 3.45-3.64 (2H, m), 3.87 (1H, brs), 7.05-7.29 (3M, m), 7.29-7.45 (2H, m), 7.67 (4H, brs), 8.68 (1H, brs), 10.47 (1H, brs), 11.03 (1H, brs)/DMSO-d$_6$ |
| 783 | ![structure: HN-CH(iBu)-CH$_2$OH] | H | 4-F | HCl | m.p.: 185-186<br>$^1$H-NMR: 0.91 (6M, d, J=6.3 Hz), 1.33-1.54 (2H, m), 1.57-1.73 (1H, m), 3.38-3.55 (2H, m), 4.10 (1H, brs), 7.07-7.28 (3H, m), 7.28-7.45 (2H, m), 7.66 (4H, brs), 8.53 (1H, brs), 10.40 (1H, brs), 10.85 (1H, brs)/DMSO-d$_6$ |
| 784 | ![structure: HN-CH(CH$_2$CH$_2$SMe)-CH$_2$OH] | H | 4-F | HCl | m.p.: 161-162<br>$^1$H-NMR: 1.70-1.83 (1H, m), 1.83-1.95 (1H, m), 2.04 (3H, s), 2.45-2.62 (2H, m), 3.51 (2H, d, J=4.4 Hz), 4.10 (1H, brs), 7.05-7.27 (3H, m), 7.27-7.44 (2H, m), 7.66 (4H, brs), 8.44 (1H, brs), 10.31 (1H, brs), 10.64 (1H, brs)/DMSO-d$_6$ |

TABLE 32-continued (continued from Table 31)

| # | Structure | | | | Data |
|---|---|---|---|---|---|
| 785 | [phenyl-CH(CH2OH)-NH- structure] | H | 4-F | HCl | m.p.: 173-174<br>¹H-NMR: 3.70 (2H, d, J=5.8 Hz), 5.06 (1H, brs), 7.04-7.19 (2H, m), 7.19-7.33 (3M, m), 7.33-7.45 (5H, m), 7.51 (2H, brs), 7.67 (2H, brs), 8.92 (1H, brs), 10.18 (1H, brs), 10.50 (1H, brs)/DMSO-$d_6$ |
| 786 | [phenyl-CH(CH2OH)-NH- structure] | H | 4-F | HCl | m.p.: 174-175<br>¹H-NMR: 3.71 (2H, d, J=4.9 Hz), 5.05 (1H, brs), 7.06-7.20 (2H, m), 7.20-7.34 (3H, m), 7.34-7.46 (5H, m), 7.50 (2H, brs), 7.68 (2H, brs), 9.18 (1H, brs), 10.34 (1H, brs), 10.79 (1H, brs)/DMSO-$d_6$ |
| 787 | [phenyl-CH(CH2CH2OH)-NH- structure] | H | 4-F | HCl | m.p.: 179-181<br>¹H-NMR: 1.81-1.95 (1H, m), 1.96-2.09 (1H, m), 3.36-3.53 (2H, m), 5.16 (1H, brs), 7.04-7.38 (5H, m), 7.38-7.45 (5H, m), 7.53 (2H, d, J=5.8 Mz), 7.66 (2H, brs), 9.13 (1H, brs), 10.24 (1H, brs), 10.58 (1H, brs)/DMSO-$d_6$ |
| 788 | [phenyl-CH(CH2CO2Me)-NH- structure] | H | 4-F | HCl | m.p.: 154-156<br>¹H-NMR: 2.80-2.97 (1H, m), 3.04 (1H, dd, J=8.8, 16.1 Hz), 3.58 (3H, s), 5.49 (1H, brs), 7.04-7.24 (3H, m), 7.24-7.40 (5H, m), 7.43 (2H, s), 7.58 (2H, d, J = 5.8 Hz), 7.67 (2H, brs), 8.92 (1H, brs), 10.14 (1H, brs), 10.35 (1H, brs)/DMSO-$d_6$ |

TABLE 33

(continued from Table 32)

| # | R | | | | Data |
|---|---|---|---|---|---|
| 789 | MeONH— | H | 4-F | HCl<br>0.8H$_2$O | m.p.: 140-141<br>¹H-NMR: 3.78 (3H, s), 7.05-7.28 (3H, m), 7.28-7.43 (2H, m), 7.67 (4H, brs), 10.53 (2H, brs), 11.79 (1H. brs)/DMSO-$d_6$ |
| 790 | EtONH— | H | 4-F | HCl<br>0.3H$_2$O<br>0.1AcOEt | m.p.: 141-143<br>¹H-NMR: 1.32 (3H, t, J=6.9 Hz), 4.01 (2H, q, J=6.9 Hz), 7.06-7.26 (3H, m), 7.29-7.44 (2H, m), 7.68 (4H, brs), 10.34 (2H, brs), 11.98 (1H, brs)/DMSO-$d_6$ |
| 791 | Me$_2$NNH— | H | 4-F | HCl | m.p.: 154-156<br>¹H-NMR: 2.64 (6H, s), 7.10-7.30 (3H, m), 7.30-7.46 (2H, m), 7.52 (2H, brs), 7.72 (2H, brs), 10.41 (1H, brs), 10.97 (1H, brs), 11.88 (1H, brs)/DMSO-$d_6$ |
| 792 | BuNHNH— | H | 4-F | HCl | m.p.: 208-209<br>¹H-NMR: 0.91 (3H, brs), 1.23-1.40 (2H, m), 1.60-1.77 (2H, m), 3.76 (2H, brs), 7.05-7.27 (3H, m), 7.27-7.45 (2H, m), 7.45-7.90 (5H, m), 9.99-11.20 (3H, m)/DMSO-$d_6$ |
| 793 | HO(CH$_2$)$_2$NHNH— | H | 4-F | 2.5HCl<br>0.6H$_2$O | m.p.: 208-209<br>¹H-NMR: 3.74 (1H, t, J=5.4 Hz), 3.86 (4H, brs), 7.05-7.28 (3H, m), 7.28-7.45 (2H, m), 7.45-7.90 (5H, m), 10.37 (2H, brs), 10.99 (1H, brs)/DMSO-$d_6$ |
| 794 | [Me-CH(NH-)-CH2CH2CH2-NEt2 structure] | H | 4-F | 2HCl<br>0.5H$_2$O | m.p.: 184-187<br>¹H-NMR: 1.10-1.25 (9H, m), 1.50-1.80 (4H, m), 2.90-3.15 (6H, m), 4.02-4.08 (1H, m), 7.05-7.25 (3H, m), 7.30-7.42 (2H, m), 7.50-7.80 (4H, m), 8.59 (1H, brs), 10.05-10.80 (2H, brs)/DMSO-$d_6$ |
| 795 | [HN-CH2-(2-fluoropyridin-4-yl) structure] | 4-Me | 4-F | HCl | m.p.: 201-204<br>¹H-NMR: 2.20-2.35 (3H, m), 4.62 (2H, brs), 5.56 (1H, brs), 6.95-7.80 (10H, m), 8.21 (1H, d, J=5.4 Hz), 8.86 (1H, brs), 9.80-10.75 (2H, m)/DMSO-$d_6$ |

TABLE 33-continued (continued from Table 32)

| | | | | | |
|---|---|---|---|---|---|
| 796 | HN-CH2-(2-F-pyridin-4-yl) | 4-MeO | 4-F | HCl | m.p.: 212-214<br>$^1$H-NMR: 3.70-3.77 (3H, m), 4.50-4.75 (3H, m), 6.70-6.98 (2H, m), 7.02-7.78 (10H, m), 8.21 (1H, d, J=4.9 Hz), 8.73 (1H, brs), 9.86-10.38 (2H, m)/DMSO-$d_6$ |
| 797 | HN-CH2-(2-F-pyridin-4-yl) | 4-Cl | 4-F | HCl | m.p.: 214-215<br>$^1$H-NMR: 4.10 (1H, brs), 4.61 (2H, brs), 6.98-7.42 (6H, m), 7.43-7.85 (4H, m), 8.21 (1H, d, J=5.3 Hz), 8.49 (1H, brs), 9.60-10.50 (2H, m)/DMSO-$d_6$ |
| 798 | HN-CH2-(2-F-pyridin-4-yl) | 4-CF$_3$ | 4-F | HCl<br>0.2H$_2$O | m.p.: 210-213<br>$^1$H-NMR 4.45-5.10 (3H, m), 6.80-7.24 (3H, m), 7.30-7.39 (1H, m), 7.45-7.85 (5H, m), 7.90-8.05 (1H, m), 8.21 (1H, d, J=5.4 Hz), 8.45-8.72 (1H, m), 9.70-10.50 (2H, m)/DMSO-$d_6$ |
| 799 | HN-CH2-(2-F-pyridin-4-yl) | 3-F | 4-F | HCl | m.p.: 213-215<br>$^1$H-NMR: 4.17 (1H, brs), 4.55-4.70 (2H, m), 6.75-6.90 (1H, m), 7.00-7.90 (9H, m), 8.16-8.22 (1H, m), 8.44 (1H, brs), 9.55-10.20 (2H, m)/DMSO-$d_6$ |
| 800 | HN-CH2-(2-F-pyridin-4-yl) | 3-Me | 4-F | HCl | m.p.: 195-197<br>$^1$H-NMR: 2.10-2.35 (3H, m), 4.64 (2H, brs), 5.76 (1H, brs), 6.80-7.00 (1H, m), 7.01-7.80 (9H, m), 8.21 (1H, d, J=4.9 Hz), 8.87 (1H, brs), 9.90-10.65 (2H, m)/DMSO-$d_6$ |
| 801 | HN-CH2-(2-F-pyridin-4-yl) | 3-MeO | 4-F | HCl | m.p.: 174-175<br>$^1$H-NMR: 3.60-3.80 (3H, m), 4.50-4.74 (2H, m), 5.81 (1H, brs), 6.57-6.78 (1H, m), 7.00-7.80 (9H, m), 8.21 (1H, d, J=3.9 Hz), 8.89 (1H, brs), 9.90-10.70 (2H, m)/DMSO-$d_6$ |

TABLE 34

(continued from Table 33)

| | | | | | |
|---|---|---|---|---|---|
| 802 | HN-CH2-(2-F-pyridin-4-yl) | H | 4-Cl | HCl | m.p.: 179-181<br>$^1$H-NMR: 4.64 (2H, brs), 6.95-7.42 (7H, m), 7.45-7.85 (4H, m), 8.21 (1H, d, J=4.9 Hz), 8.40-8.90 (1H, m), 9.70-10.40 (2H, m)/DMSO-d6 |
| 803 | HN-CH2-furan-2-yl | H | 4-Cl | HCl | m.p.: 187-188<br>$^1$H-NMR: 4.58 (2H, brs), 6.30-6.50 (2H, m), 7.10-7.18 (1H, m), 7.30-7.44 (4H, m), 7.52-7.80 (5H, m), 8.95 (1H, brs), 10.10-10.80 (2H, m)/DMSO-$d_6$ |
| 804 | HN-CH2-(2-F-pyridin-4-yl) | H | 4-Me | HCl<br>0.2H$_2$O | m.p.: 176-177<br>$^1$H-NMR: 1.95 (2H, d, J=17), 4.62 (2H, brs), 6.98-7.78 (11H, m), 7.42-7.80 (4H, m), 8.21 (1H, d, J=5.4 Hz), 8.79 (1H, brs), 9.85-10.50 (2H, m)/DMSO-$d_6$ |
| 805 | HN-CH2-furan-2-yl | H | 4-Me | HCl | m.p.: 173-174<br>$^1$H-NMR: 2.29 (3H, d, J=4.3 Hz), 4.58 (2H, brs), 6.25-6.55 (2H, m), 7.05-7.20 (3H, m), 7.28-7.42 (2H, m), 7.43-7.75 (5H, m), 9.11 (1H, brs), 10.20-11.00 (2H, m)/DMSO-$d_6$ |
| 806 | HN-CH2-(2-F-pyridin-4-yl) | H | 4-MeO | HCl | m.p.: 176-177<br>$^1$H-NMR: 3.75 (3H, d, J=12.7), 4.64 (2H, brs), 6.70-7.00 (2H, m), 7.02-7.78 (9H, m), 8.21 (1H, d, J=5.3 Hz), 9.08 (1H, brs), 9.95-10.75 (2H, m)/DMSO-$d_6$ |
| 807 | HN-CH2-furan-2-yl | H | 4-MeO | HCl | m.p.: 145-148<br>$^1$H-NMR: 3.76 (3H, d, J=2.5 Hz), 4.58 (2H, brs), 6.20-6.54 (2H, m), 6.90-6.98 (2H, m), 7.05-7.18 (1H, m), 7.25-7.42 (2H, m), 7.43-7.75 (5H, m), 9.05 (1H, brs), 10.05-10.85 (2H, m)/DMSO-$d_6$ |

TABLE 34-continued (continued from Table 33)

| 808 | MeO(CH₂)₂NH— | | H | 4-MeO | 1.4HCl | m.p. 169-170<br>¹H-NMR: 3.29 (3H, s), 3.45-3.63 (4H, m), 3.73-3.80 (3H, m), 6.85-7.03 (2H, m), 7.05-7.22 (1H, m), 7.25-7.80 (6H, m), 8.83 (1H, brs), 10.15-11.20 (2H, m)/DMSO-d₆ |
|---|---|---|---|---|---|---|
| 809 | 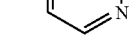 | F | H | 4-CF₃ | HCl<br>0.1H₂O | m.p.: 178-180<br>¹H-NMR: 4.64 (2H, brs), 6.98-7.42 (5H, m), 7.45-8.04 (7H, m), 8.21 (1H, d, J=5.4 Hz), 8.46-8.75 (1H, m), 9.73-10.40 (2H, m)/DMSO-d₆ |
| 810 | 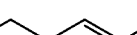 | | H | 4-CF₃ | HCl | m.p.: 157-159<br>¹H-NMR: 4.59 (2H, brs), 6.32-6.46 (2H, m), 7.05-7.16 (1H, m), 7.30-7.40 (2H, m), 7.60-7.75 (5H, m), 7.88-8.04 (2H, m), 8.60-9.00 (1H, m), 10.05-10.70 (2H, m)/DMSO-d₆ |
| 811 | 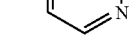 | F | H | 3-F | HCl | m.p.: 204-206<br>¹H-NMR: 4.54-4.70 (2H, m) 5.95 (1H, brs), 6.76-6.92 (1H, m), 6.98-7.95 (10H, m), 8.15-8.25 (1H, m), 8.60 (1H, brs), 9.70-10.40 (2H, m)/DMSO-d₆ |
| 812 | 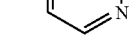 | F | H | 3-Me | HCl<br>0.1H₂O | m.p.: 184-185<br>¹H-NMR: 2.15-2.35 (3H, m), 4.65 (2H, brs), 6.85-7.00 (2H, m) 7.03-7.80 (9H, m), 8.22 (1H, d, J=4.8 Hz), 8.99 (1H, brs), 10.05-10.70 (2H, m)/DMSO-d₆ |
| 813 | 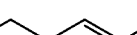 | | H | 3-Me | HCl | m.p.: 144-147<br>¹H-NMR: 2.25-2.35 (3H, m), 4.59 (2H, brs), 6.30-6.50 (2H, m), 6.91-6.98 (1H, m), 7.10-7.25 (2H, m), 7.30-7.75 (7H, m), 8.99 (1H, brs), 10.10-10.75 (2H, m)/DMSO-d₆ |

TABLE 35

(continued from Table 34)

| 814 | 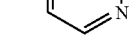 | F | H | 3,4-diF | HCl | m.p.: 199-202<br>¹H-NMR: 4.54-4.72 (2H, m), 6.18 (1H, brs), 6.95-8.15 (10H, m), 8.21 (1H, d, J=4.9 Hz), 8.40-9.00 (1H, m), 9.70-10.50 (2H, m)/DMSO-d₆ |
|---|---|---|---|---|---|---|
| 815 | 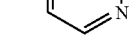 | F | H | 4-F,3-Me | HCl | m.p.: 190-191<br>¹H-NMR: 2.05-2.30 (3H, m), 4.50-4.70 (2H, m), 6.95-7.75 (10 H, m), 8.21 (1H, d, J=4.9 Hz), 8.82 (1H, brs), 9.85-10.50 (2H, m)/DMSO-d₆ |
| 816 |  | | H | 4-F | 0.9HCl<br>H₂O | m.p.: 172-174<br>¹H-NMR: 4.39 (2H, brs), 6.61 (1H, d, J=9.3 Hz), 7.05-7.29 (3H, m), 7.29-7.44 (2H, m), 7.44-7.89 (7H, m), 9.19 (1H, brs), 10.61 (1H, brs), 10.88 (1H, brs)/DMSO-d₆ |
| 817 |  | | H | 4-F | 1.6HCl<br>1.5H₂O | m.p.: 157-158<br>¹H-NMR: 4.47 (2H, brs), 6.45 (1H, d, J=6.9 Hz), 6.54 (1H, s), 7.04-7.26 (4H, m), 7.26-7.34 (1H, m), 7.34-7.44 (1H, m), 7.54 (2H, brs), 7.58 (1H, d, J=6.9 Hz), 7.68 (2H, brs), 9.19 (1H, brs), 10.45 (1H, brs), 10.77 (1H, brs)/DMSO-d₆ |
| 818 |  | | H | 4-F | 1.6HCl<br>0.5H₂O | m.p.: 157-158<br>¹H-NMR: 4.47 (2H, brs), 6.36 (1H, s), 6.44 (1H, d, J=8.8 Hz), 7.14-7.26 (3H, m), 7.26-7.34 (1H, m), 7.34-7.43 (1H, m), 7.43-7.60 (4H, m), 7.68 (2H, brs), 8.99 (1H, brs), 10.41 (1H, brs), 10.74 (1H, brs)/DMSO-d₆ |
| 819 | 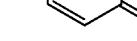 | | H | 4-F | 2HCl<br>0.8H₂O | m.p.: 164-165<br>¹H-NMR: 4.60 (2H, d, J=5.4 Hz), 6.78 (1H, d, J=6.9 Hz), 6.90 (1H, d, J=8.8 Hz), 6.95-7.23 (3H, m), 7.23-7.40 (2H, m), 7.57 (2H, brs), 7.70 (2H, brs), 7.82-7.95 (1H, m), 8.19 (2H, brs), 8.55 (1H, brs), 10.11 (2H, brs), 14.24 (1H, brs)/DMSO-d₆ |

TABLE 35-continued (continued from Table 34)

| 820 | [HN-CH2-(1H-1,2,4-triazol-5-yl)] | H | 4-F | free | m.p.: 223-225<br>$^1$H-NMR: 4.74 (2H, brs), 7.00-7.26 (4H, m), 7.26-7.44 (2H, m), 7.54 (2H, brs), 7.68 (3H, brs), 8.79 (1H, s), 8.97 (1H, brs), 10.35 (1H, brs), 10.61 (1H, brs)/DMSO-$d_6$ |
|---|---|---|---|---|---|
| 821 | [HN-CH2-(1H-imidazol-5-yl)] | H | 4-F | 2HCl<br>0.5H$_2$O | m.p.: 202-203<br>$^1$H-NMR: 4.63 (2H, brs), 7.03-7.26 (3H, m), 7.26-7.45 (2H, m), 7.62 (5H, brs), 8.96 (1H, brs), 9.09 (1H, s), 10.51 (2H, brs), 14.65 (2H, brs)/DMSO-$d_6$ |

TABLE 36

(The numbers 2 to 6 in the formula above represent respective bonding positions of $R^3$ and $R^5$.)

| No | $R^{101}$ | $R^3$ | $R^5$ |
|---|---|---|---|
| 1 | 3-FPy-2-yl | H | H |
| 2 | 3-FPy-2-yl | H | 4-F |
| 3 | 3-FPy-2-yl | 4-F | 4-F |
| 4 | 3-FPy-2-yl | H | 4-MeO |
| 5 | 3-FPy-2-yl | 4-Me | 4-F |
| 6 | 3-FPy-2-yl | 4-MeO | 4-F |
| 7 | 4-FPy-2-yl | H | H |
| 8 | 4-FPy-2-yl | H | 4-F |
| 9 | 4-FPy-2-yl | 4-F | 4-F |
| 10 | 4-FPy-2-yl | H | 4-MeO |
| 11 | 4-FPy-2-yl | 4-Me | 4-F |
| 12 | 4-FPy-2-yl | 4-MeO | 4-F |
| 13 | 5-FPy-2-yl | H | H |
| 14 | 5-FPy-2-yl | H | 4-F |
| 15 | 5-FPy-2-yl | 4-F | 4-F |
| 16 | 3-FPy-4-yl | 4-F | 4-F |
| 17 | 3-FPy-4-yl | H | MeO |
| 18 | 3-FPy-4-yl | 4-Me | 4-F |
| 19 | 2-methylpyrimidin-4-yl | H | H |
| 20 | 2-methylpyrimidin-4-yl | 4-F | 4-F |
| 21 | 2-methylpyrimidin-4-yl | H | 4-MeO |
| 22 | 2-methylpyrimidin-4-yl | 4-Me | 4-F |
| 23 | 2-methylpyrimidin-4-yl | 4-MeO | 4-F |
| 24 | 5-methylpyrimidin-4-yl | H | 4-MeO |
| 25 | 5-methylpyrimidin-4-yl | 4-Me | 4-F |
| 26 | 5-methylpyrimidin-4-yl | 4-MeO | 4-F |
| 27 | 5-FPy-2-yl | H | 4-MeO |
| 28 | 5-FPy-2-yl | 4-Me | 4-F |
| 29 | 5-FPy-2-yl | 4-MeO | 4-F |
| 30 | 6-FPy-2-yl | H | H |
| 31 | 6-FPy-2-yl | 4-F | 4-F |
| 32 | 6-FPy-2-yl | H | 4-MeO |
| 33 | 6-FPy-2-yl | 4-Me | 4-F |
| 34 | 6-FPy-2-yl | 4-MeO | 4-F |
| 35 | 5-FPy-3-yl | H | H |
| 36 | 5-FPy-3-yl | H | 4-F |
| 37 | 5-FPy-3-yl | 4-F | 4-F |
| 38 | 5-FPy-3-yl | H | 4-MeO |
| 39 | 5-FPy-3-yl | 4-Me | 4-F |
| 40 | 5-FPy-3-yl | 4-MeO | 4-F |
| 41 | 2-FPy-3-yl | H | H |
| 42 | 3-FPy-4-yl | 4-MeO | 4-F |
| 43 | 3-FPy-4-yl | H | H |
| 44 | 3-FPy-4-yl | H | 4-F |
| 45 | 4-methylpyrimidin-5-yl | H | H |

TABLE 36-continued

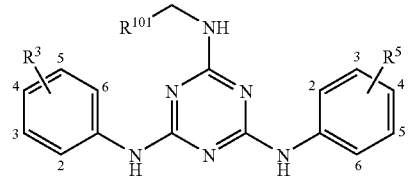

(The numbers 2 to 6 in the formula above represent respective bonding positions of $R^3$ and $R^5$.)

| No | $R^{101}$ | $R^3$ | $R^5$ |
|---|---|---|---|
| 46 | 4-methylpyrimidin-5-yl (pyrimidine, Me at 4) | H | 4-F |
| 47 | 4-methylpyrimidin-5-yl | 4-F | 4-F |
| 48 | 4-methylpyrimidin-5-yl | H | 4-MeO |
| 49 | 4-methylpyrimidin-5-yl | 4-Me | 4-F |
| 50 | 5-methylpyrimidin-2-yl | H | H |
| 51 | 5-methylpyrimidin-2-yl | H | 4-F |
| 52 | 5-methylpyrimidin-2-yl | 4-F | 4-F |
| 53 | 2-FPy-3-yl | H | 4-F |
| 54 | 2-FPy-3-yl | 4-F | 4-F |
| 55 | 2-FPy-3-yl | H | 4-MeO |
| 56 | 2-FPy-3-yl | 4-Me | 4-F |
| 57 | 2-FPy-3-yl | 4-MeO | 4-F |
| 58 | 4-FPy-3-yl | H | H |
| 59 | 4-FPy-3-yl | H | 4-F |
| 60 | 4-FPy-3-yl | 4-F | 4-F |
| 61 | 4-FPy-3-yl | H | 4-MeO |
| 62 | 4-FPy-3-yl | 4-Me | 4-F |
| 63 | 4-FPy-3-yl | 4-MeO | 4-F |
| 64 | 6-FPy-3-yl | H | H |
| 65 | 6-FPy-3-yl | H | 4-F |
| 66 | 6-FPy-3-yl | 4-F | 4-F |
| 67 | 6-FPy-3-yl | H | 4-MeO |
| 68 | 6-FPy-3-yl | 4-Me | 4-F |
| 69 | 6-FPy-3-yl | 4-MeO | 4-F |
| 70 | 2-FPy-4-yl | H | H |
| 71 | 6-methylpyrimidin-4-yl | 4-MeO | 4-F |

TABLE 36-continued

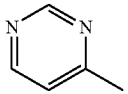

(The numbers 2 to 6 in the formula above represent respective bonding positions of $R^3$ and $R^5$.)

| No | $R^{101}$ | $R^3$ | $R^5$ |
|---|---|---|---|
| 72 | 5-methylpyrimidin-2-yl | H | H |
| 73 | 5-methylpyrimidin-2-yl | H | 4-F |
| 74 | 5-methylpyrimidin-2-yl | 4-F | 4-F |
| 75 | 3-methylpyrazin-2-yl | H | 4-MeO |
| 76 | 3-methylpyrazin-2-yl | 4-Me | 4-F |
| 77 | 3-methylpyrazin-2-yl | 4-MeO | 4-F |
| 78 | 3-methylpyridazin-6-yl | H | H |

TABLE 37

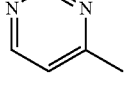

(The numbers 2 to 6 in the formula above represent respective bonding positions of $R^3$ and $R^5$.)

| No | $R^{101}$ | $R^3$ | $R^5$ |
|---|---|---|---|
| 79 | 3-methylpyridazin-6-yl | H | 4-F |

TABLE 37-continued (The numbers 2 to 6 in the formula above represent respective bonding positions of R³ and R⁵.)

| No | R¹⁰¹ | R³ | R⁵ |
|---|---|---|---|
| 80 | pyridazin-3-yl-methyl | 4-F | 4-F |
| 81 | pyridazin-3-yl-methyl | H | 4-MeO |
| 82 | pyridazin-3-yl-methyl | 4-Me | 4-F |
| 83 | pyridazin-3-yl-methyl | 4-MeO | 4-F |
| 84 | pyridazin-4-yl-methyl | H | H |
| 85 | pyridazin-4-yl-methyl | H | 4-F |
| 86 | pyridazin-4-yl-methyl | F | F |
| 87 | pyridazin-4-yl-methyl | H | 4-MeO |
| 88 | pyridazin-4-yl-methyl | 4-Me | 4-F |
| 89 | pyridazin-4-yl-methyl | 4-MeO | 4-F |
| 90 | 4-ethylpyridazin-?-yl-methyl | H | H |
| 91 | 4-ethylpyridazin-?-yl-methyl | H | 4-F |
| 92 | 4-ethylpyridazin-?-yl-methyl | 4-F | 4-F |
| 93 | 5-ethylpyridazin-?-yl-methyl | H | 4-MeO |
| 94 | 5-methylpyridazin-?-yl-methyl | 4-Me | 4-F |
| 95 | 5-methylpyridazin-?-yl-methyl | 4-MeO | 4-F |
| 96 | furan-2-yl-methyl | H | H |
| 97 | furan-2-yl-methyl | 4-F | 4-F |
| 98 | furan-2-yl-methyl | H | 4-MeO |
| 99 | furan-2-yl-methyl | 4-Me | 4-F |
| 100 | furan-2-yl-methyl | 4-MeO | 4-F |
| 101 | furan-3-yl-methyl | H | H |
| 102 | furan-3-yl-methyl | H | 4-F |

TABLE 37-continued

(The numbers 2 to 6 in the formula above represent respective bonding positions of R³ and R⁵.)

| No | R¹⁰¹ | R³ | R⁵ |
|---|---|---|---|
| 103 |  (furyl) | 4-F | 4-F |
| 104 |  (furyl) | 4-Me | 4-F |
| 105 |  (furyl) | 4-MeO | 4-F |
| 106 |  (thiazolyl) | H | H |
| 107 |  (thiazolyl) | H | 4-F |
| 108 |  (thiazolyl) | 4-F | 4-F |
| 109 |  (thiazolyl) | H | 4-MeO |
| 110 |  (thiazolyl) | 4-Me | 4-F |
| 111 | 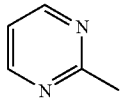 (thiazolyl) | 4-MeO | 4-F |

TABLE 38

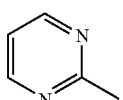

(The numbers 2 to 6 in the formula above represent respective bonding positions of R³ and R⁵.)

| No | R¹⁰¹ | R³ | R⁵ |
|---|---|---|---|
| 112 | 3-FPy-2-yl | H | H |
| 113 | 3-FPy-2-yl | H | 4-F |

TABLE 38-continued

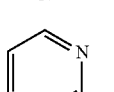

(The numbers 2 to 6 in the formula above represent respective bonding positions of R³ and R⁵.)

| No | R¹⁰¹ | R³ | R⁵ |
|---|---|---|---|
| 114 | 3-FPy-2-yl | 4-F | 4-F |
| 115 | 3-FPy-2-yl | H | 4-MeO |
| 116 | 3-FPy-2-yl | 4-Me | 4-F |
| 117 | 3-FPy-2-yl | 4-MeO | 4-F |
| 118 | 4-FPy-2-yl | H | H |
| 119 | 4-FPy-2-yl | H | 4-F |
| 120 | 4-FPy-2-yl | 4-F | 4-F |
| 121 | 4-FPy-2-yl | H | 4-MeO |
| 122 | 4-FPy-2-yl | 4-Me | 4-F |
| 123 | 4-FPy-2-yl | 4-MeO | 4-F |
| 124 | 5-FPy-2-yl | H | H |
| 125 | 5-FPy-2-yl | H | 4-F |
| 126 | 5-FPy-2-yl | 4-F | 4-F |
| 127 | 3-FPy-4-yl | 4-F | 4-F |
| 128 | 3-FPy-4-yl | H | MeO |
| 129 | 3-FPy-4-yl | 4-Me | 4-F |
| 130 | 2-FPy-4-yl | H | H |
| 131 | 2-FPy-4-yl | H | 4-F |
| 132 | 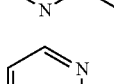 (pyrimidinyl) | H | H |
| 133 | 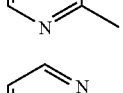 (pyrimidinyl) | 4-F | 4-F |
| 134 | (pyrimidinyl) | H | 4-MeO |
| 135 | (pyrimidinyl) | 4-Me | 4-F |
| 136 | (pyrimidinyl) | 4-MeO | 4-F |
| 137 | 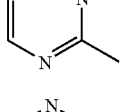 (pyrimidinyl) | H | 4-MeO |
| 138 | 5-FPy-2-yl | H | 4-MeO |
| 139 | 5-FPy-2-yl | 4-Me | 4-F |
| 140 | 5-FPy-2-yl | 4-MeO | 4-F |
| 141 | 6-FPy-2-yl | H | H |
| 142 | 6-FPy-2-yl | 4-F | 4-F |
| 143 | 6-FPy-2-yl | H | 4-MeO |
| 144 | 6-FPy-2-yl | 4-Me | 4-F |
| 145 | 6-FPy-2-yl | 4-MeO | 4-F |
| 146 | 5-FPy-3-yl | H | H |
| 147 | 5-FPy-3-yl | H | 4-F |
| 148 | 5-FPy-3-yl | 4-F | 4-F |

TABLE 38-continued (The numbers 2 to 6 in the formula above represent respective bonding positions of $R^3$ and $R^5$.)

| No | $R^{101}$ | $R^3$ | $R^5$ |
|---|---|---|---|
| 149 | 5-FPy-3-yl | H | 4-MeO |
| 150 | 5-FPy-3-yl | 4-Me | 4-F |
| 151 | 5-FPy-3-yl | 4-MeO | 4-F |
| 152 | 2-FPy-3-yl | H | H |
| 153 | 3-FPy-4-yl | 4-MeO | 4-F |
| 154 | 3-FPy-4-yl | H | H |
| 155 | 3-FPy-4-yl | H | 4-F |
| 156 | 2-FPy-4-yl | 4-F | 4-F |
| 157 | 2-FPy-4-yl | H | 4-MeO |
| 158 | pyrimidin-4-ylmethyl | H | H |
| 159 | pyrimidin-4-ylmethyl | H | 4-F |
| 160 | pyrimidin-4-ylmethyl | 4-F | 4-F |
| 161 | pyrimidin-4-ylmethyl | H | 4-MeO |
| 162 | pyrimidin-4-ylmethyl | 4-Me | 4-F |
| 163 | pyrimidin-5-ylmethyl | H | H |
| 164 | 2-FPy-3-yl | H | 4-F |
| 165 | 2-FPy-3-yl | 4-F | 4-F |
| 166 | 2-FPy-3-yl | H | 4-MeO |
| 167 | 2-FPy-3-yl | 4-Me | 4-F |
| 168 | 2-FPy-3-yl | 4-MeO | 4-F |
| 169 | 4-FPy-3-yl | H | H |
| 170 | 4-FPy-3-yl | H | 4-F |
| 171 | 4-FPy-3-yl | 4-F | 4-F |
| 172 | 4-FPy-3-yl | H | 4-MeO |
| 173 | 4-FPy-3-yl | 4-Me | 4-F |
| 174 | 4-FPy-3-yl | 4-MeO | 4-F |
| 175 | 6-FPy-3-yl | H | H |
| 176 | 6-FPy-3-yl | H | 4-F |
| 177 | 6-FPy-3-yl | 4-F | 4-F |
| 178 | 6-FPy-3-yl | H | 4-MeO |
| 179 | 6-FPy-3-yl | 4-Me | 4-F |
| 180 | 6-FPy-3-yl | 4-MeO | 4-F |
| 181 | 2-FPy-4-yl | H | H |
| 182 | 2-FPy-4-yl | 4-Me | 4-F |
| 183 | 2-FPy-4-yl | 4-MeO | 4-F |
| 184 | pyrimidin-5-ylmethyl | 4-MeO | 4-F |
| 185 | pyrimidin-5-ylmethyl | H | H |
| 186 | pyrimidin-5-ylmethyl | H | 4-F |
| 187 | pyrimidin-5-ylmethyl | 4-F | 4-F |
| 188 | pyrazin-2-ylmethyl | H | 4-MeO |
| 189 | pyrazin-2-ylmethyl | 4-Me | 4-F |

TABLE 39

(The numbers 2 to 6 in the formula above represent respective bonding positions of $R^3$ and $R^5$.)

| No | $R^{101}$ | $R^3$ | $R^5$ |
|---|---|---|---|
| 190 | pyrimidin-5-yl | 4-Me | 4-F |
| 191 | pyrimidin-5-yl | 4-MeO | 4-F |

TABLE 39-continued

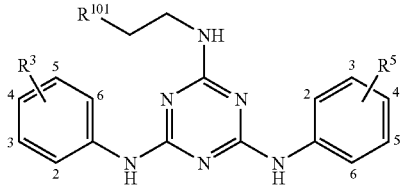

(The numbers 2 to 6 in the formula above represent respective bonding positions of $R^3$ and $R^5$.)

| No | $R^{101}$ | $R^3$ | $R^5$ |
|---|---|---|---|
| 192 | pyridazin-3-yl | H | 4-F |
| 193 | pyridazin-3-yl | 4-F | 4-F |
| 194 | pyridazin-3-yl | H | 4-MeO |
| 195 | pyridazin-3-yl | 4-Me | 4-F |
| 196 | pyridazin-3-yl | 4-MeO | 4-F |
| 197 | pyridazin-4-yl | H | H |
| 198 | pyridazin-4-yl | H | 4-F |
| 199 | pyridazin-4-yl | F | F |
| 200 | pyridazin-4-yl | H | 4-MeO |
| 201 | pyridazin-4-yl | 4-Me | 4-F |
| 202 | pyridazin-4-yl | 4-MeO | 4-F |

TABLE 39-continued

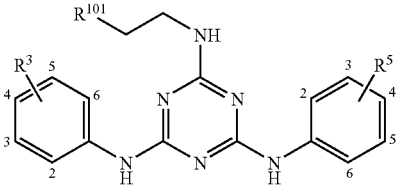

(The numbers 2 to 6 in the formula above represent respective bonding positions of $R^3$ and $R^5$.)

| No | $R^{101}$ | $R^3$ | $R^5$ |
|---|---|---|---|
| 203 | pyrimidin-5-yl | H | 4-F |
| 204 | pyrimidin-5-yl | 4-F | 4-F |
| 205 | pyridazinyl-ethyl | H | H |
| 206 | pyridazinyl-ethyl | H | 4-F |
| 207 | pyridazinyl-ethyl | 4-F | 4-F |
| 208 | pyridazinyl-ethyl | H | 4-MeO |
| 209 | pyridazin-4-yl | 4-Me | 4-F |
| 210 | pyridazin-4-yl | 4-MeO | 4-F |
| 211 | furan-2-yl | H | H |
| 212 | furan-2-yl | 4-F | 4-F |
| 213 | furan-2-yl | H | 4-MeO |
| 214 | furan-2-yl | 4-Me | 4-F |

TABLE 39-continued

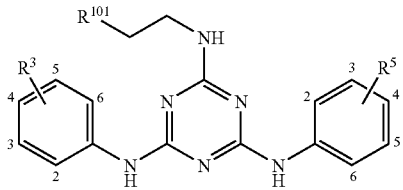

(The numbers 2 to 6 in the formula above represent respective bonding positions of $R^3$ and $R^5$.)

| No | $R^{101}$ | $R^3$ | $R^5$ |
|---|---|---|---|
| 215 | 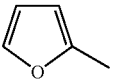 | 4-MeO | 4-F |
| 216 | 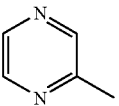 | 4-MeO | 4-F |
| 217 | 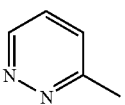 | H | H |
| 218 | 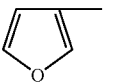 | H | H |
| 219 | 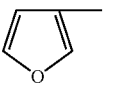 | H | 4-F |
| 220 | 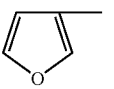 | 4-F | 4-F |
| 221 | 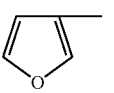 | 4-Me | 4-F |
| 222 | 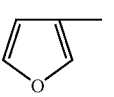 | 4-MeO | 4-F |

TABLE 39-continued

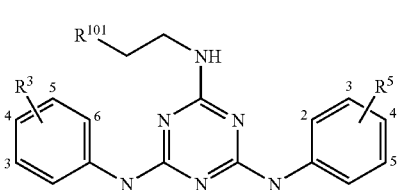

(The numbers 2 to 6 in the formula above represent respective bonding positions of $R^3$ and $R^5$.)

| No | $R^{101}$ | $R^3$ | $R^5$ |
|---|---|---|---|
| 223 | 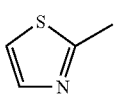 | H | H |
| 224 | 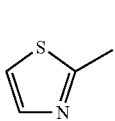 | H | 4-F |
| 225 | 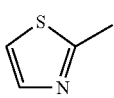 | 4-F | 4-F |
| 226 | 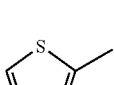 | H | 4-MeO |
| 227 | 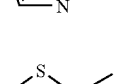 | 4-Me | 4-F |
| 228 | 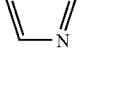 | 4-MeO | 4-F |

The invention claimed is:

1. A 2,4,6-triamino-1,3,5-triazine selected from the group consisting of the following compounds or a pharmaceutically acceptable salt thereof:

N,N'-diphenyl-N"-(4-pyridylmethyl)-1,3,5-triazine-2,4,6-triamine,

N,N'-diphenyl-N"-(pyridin-3-ylmethyl)-1,3,5-triazine-2,4,6-triamine,

N,N'-diphenyl-N"-(pyridin-2-ylmethyl)-1,3,5-triazine-2,4,6-triamine,

N-[(2-fluoropyridin-4-yl)methyl]-N',N"-diphenyl-1,3,5-triazine-2,4,6-triamine,

N-[(2-chloropyridin-4-yl)methyl]-N',N"-diphenyl-1,3,5-triazine-2,4,6-triamine,

N-[(2-isopropylpyridin-4-yl)methyl]-N',N"-diphenyl-1,3,5-triazine-2,4,6-triamine, N,N'-diphenyl-N"-(2-pyridin-4-ylethyl)-1,3,5-triazine-2,4,6-triamine, N-(3,4-difluorophenyl)-N'-[(2-fluoropyridin-4-yl)methyl]-N"-phenyl-1,3,5-triazine-2,4,6-triamine, N-[(2-fluoropyridin-4-yl)methyl]N'-(4-methoxyphenyl)-N"-phenyl-1,3,5-triazine-2,4,6-triamine, N-(4-fluorophenyl)-N'-[(2-fluoropyridin-4-yl)methyl]-N"-(4-methylphenyl)-1,3,5-triazine-2,4,6-triamine, N-[(5-methyl-2-furyl)methyl]-N',N"-diphenyl-1,3,5-triazine-2,4,6-triamine, N,N'-diphenyl-N"-(2-thienylmethyl)-1,3,5-triazine-2,4,6-triamine, N-(2-furylmethyl)-N',N"-diphenyl-1,3,5-triazine-2,4,6-triamine, N-(2-furylmethyl)-N'-(4-methylphenyl)-N"-phenyl-1,3,5-triazine-2,4,6-triamine, N,N'-diphenyl-N"-(pyrimidin-2-ylmethyl)-1,3,5-triazine-2,4,6-triamine, N,N'-bis(4-fluorophenyl)-N"-(pyrimidin-2-ylmethyl)-1,3,5-triazine-2,4,6-triamine, N-(4-fluorophenyl)-N'-phenyl-N"-(pyrimidin-2-ylmethyl)-1,3,5-triazine-2,4,6-triamine, N-(4-fluorophenyl)-N'-(4-methoxyphenyl)-N"-(pyrimidin-2-ylmethyl)-1,3,5-triazine-2,4,6-triamine, N,N'-bis(4-fluorophenyl)-N"-(pryidin-4-ylmethyl)-1,3,5-triazine-2,4,6-triamine, N,N'-bis(4-fluorophenyl)-N"-(pyridin-3-ylmethyl)-1,3,5-triazine-2,4,6-triamine, N,N'-bis(4-fluorophenyl)-N"-(pyridin-2-ylmethyl)-1,3,5-triazine-2,4,6-triamine, N,N'-bis(4-fluorophenyl)-N"-[(2-fluoropyridin-4-yl)methyl]-1,3,5-triazine-2,4,6-triamine, N-(4-fluorophenyl)-N'-[(2-fluoropyridin-4-yl)methyl]-N"-phenyl-1,3,5-triazine-2,4,6-triamine, N-(4-fluorophenyl)-N'-[(2-methylpyridin-4-yl)methyl]-N"-phenyl-1,3,5-triazine-2,4,6-triamine, N-[(2-fluoropyridin-4-yl)methyl]-N'-(4-methylphenyl)-N"-phenyl-1,3,5-triazine-2,4,6-triamine, {4-[({4-anilino-6-[(4-fluorophenyl)amino]-1,3,5-triazin-2-yl}amino)methyl]pyridin-2-yl}methanol, N-(4-fluorophenyl)-N'-(2-furylmethyl)-N"-phenyl-1,3,5-triazine-2,4,6-triamine, N-(4-fluorophenyl)-N'-phenyl-N"-(1,3-thiazol-4-ylmethyl)-1,3,5-triazine-2,4,6-triamine, N-(4-fluorophenyl)-N'-phenyl-N''-(pyrimidin-4-ylmethyl)-1,3,5-triazine-2,4,6-triamine,
N,N'-bis(4-fluorophenyl)-N''-(pyrimidin-4-ylmethyl)-1,3,5-triazine-2,4,6-triamine,
N-(4-fluorophenyl)-N'-[(2-fluoropyridin-4-yl)methyl]-N''-(4-methoxyphenyl)-1,3,5-triazine-2,4,6-triamine,
N-(4-chlorophenyl)-N'-(4-fluorophenyl)-N''-[(2-fluoropyridin-4-yl)methyl]-1,3,5-triazine-2,4,6-triamine,
N-(4-chlorophenyl)-N'-[(2-fluoropyridin-4-yl)methyl]-N''-phenyl-1,3,5-triazine-2,4,6-triamine,
3-{[(4,6-dianilino-1,3,5-triazin-2-yl)amino]methyl}dihydrofuran-2(3H)-one,
N,N'-bis(4-fluorophenyl)-N'-(2-furylmethyl)-1,3,5-triazine-2,4,6-triamine,
N-(4-fluorophenyl)-N'-(phenyl)-N''-(1,3-thiazol-2-ylmethyl)-1,3,5-triazine-2,4,6-triamine,
N-(4-fluorophenyl)-N'-(4-methoxyphenyl)-N''-(pyrimidin-4-ylmethyl)-1,3,5-triazine-2,4,6-triamine,
N-(4-fluorophenyl)-N'-phenyl-N''-(pyridazin-4-ylmethyl)-1,3,5-triazine-2,4,6-triamine,
N,N'-bis(4-fluorophenyl)-N''-(pyridazin-4-ylmethyl)-1,3,5-triazine-2,4,6-triamine,
N-(4-fluorophenyl)-N'-(4-methoxyphenyl)-N''-(pyridazin-4-ylmethyl)-1,3,5-triazine-2,4,6-triamine, and
N-(4-fluorophenyl)-N'-phenyl-N''-(pyridazin-3-ylmethyl)-1,3,5-triazine-2,4,6-triamine.

2. A 2,4,6-triamino-1,3,5-triazine selected from the group consisting of the following compounds or a pharmaceutically acceptable salt thereof:
N,N'-diphenyl-N''-(pyrimidin-2-ylmethyl)-1,3,5-triazine-2,4,6-triamine,
N,N'-bis(4-fluorophenyl)-N''-(pyrimidin-2-ylmethyl)-1,3,5-triazine-2,4,6-triamine,
N-(4-fluorophenyl)-N'-phenyl-N''-(pyrimidin-2-ylmethyl)-1,3,5-triazine-2,4,6-triamine, and
N-(4-fluorophenyl)-N'-(4-methoxyphenyl)-N''-(pyrimidin-2-ylmethyl)-1,3,5-triazine-2,4,6-triamine.

3. A 2,4,6-triamino-1,3,5-triazine selected from the group consisting of the following compounds or a pharmaceutically acceptable salt thereof:
N-(4-fluorophenyl)-N'-phenyl-N''-(pyrimidin-4-ylmethyl)-1,3,5-triazine-2,4,6-triamine,
N,N'-bis(4-fluorophenyl)-N''-(pyrimidin-4-ylmethyl)-1,3,5-triazine-2,4,6-triamine, and
N-(4-fluorophenyl)-N'-(4-methoxyphenyl)-N''-(pyrimidin-4-ylmethyl)-1,3,5-triazine-2,4,6-triamine.

* * * * *

SEQUENCE LISTING

<160> NUMBER OF SEQ ID NOS: 12

<210> SEQ ID NO 1
<211> LENGTH: 3252
<212> TYPE: DNA
<213> ORGANISM: Homo sapiens
<220> FEATURE:
<221> NAME/KEY: CDS
<222> LOCATION: (1)..(3252)

<400> SEQUENCE: 1 atg ccg gcc atg cgg ggc ctc ctg gcg cct cag aac acc ttc ctg gac    48

```
Met Pro Ala Met Arg Gly Leu Leu Ala Pro Gln Asn Thr Phe Leu Asp
1               5                   10                  15 acc atc gct acg cgc ttc gac ggc acg cac agt aac ttc gtg ctg ggc    96
Thr Ile Ala Thr Arg Phe Asp Gly Thr His Ser Asn Phe Val Leu Gly
            20                  25                  30 aac gcc cag gtg gcg ggg ctc ttc ccc gtg gtc tac tgc tct gat ggc   144
Asn Ala Gln Val Ala Gly Leu Phe Pro Val Val Tyr Cys Ser Asp Gly
        35                  40                  45 ttc tgt gac ctc acg ggc ttc tcc cgg gct gag gtc atg cag cgg ggc   192
Phe Cys Asp Leu Thr Gly Phe Ser Arg Ala Glu Val Met Gln Arg Gly
    50                  55                  60 tgt gcc tgc tcc ttc ctt tat ggg cca gac acc agt gag ctc gtc cgc   240
Cys Ala Cys Ser Phe Leu Tyr Gly Pro Asp Thr Ser Glu Leu Val Arg
65                  70                  75                  80 caa cag atc cgc aag gcc ctg gac gag cac aag gag ttc aag gct gag   288
Gln Gln Ile Arg Lys Ala Leu Asp Glu His Lys Glu Phe Lys Ala Glu
                85                  90                  95 ctg atc ctg tac cgg aag agc ggg ctc ccg ttc tgg tgt ctc ctg gat   336
Leu Ile Leu Tyr Arg Lys Ser Gly Leu Pro Phe Trp Cys Leu Leu Asp
            100                 105                 110 gta ata ccc ata aag aat gag aaa ggg gag gtg gct ctc ttc cta gtc   384
Val Ile Pro Ile Lys Asn Glu Lys Gly Glu Val Ala Leu Phe Leu Val
        115                 120                 125 tct cac aag gac atc agc gaa acc aag aac cga ggg ggc ccc gac aga   432
Ser His Lys Asp Ile Ser Glu Thr Lys Asn Arg Gly Gly Pro Asp Arg
    130                 135                 140 tgg aag gag aca ggt ggt ggc cgg cgc cga tat ggc cgg gca cga tcc   480
Trp Lys Glu Thr Gly Gly Gly Arg Arg Arg Tyr Gly Arg Ala Arg Ser
145                 150                 155                 160 aaa ggc ttc aat gcc aac cgg cgg cgg agc cgg gcc gtg ctc tac cac   528
Lys Gly Phe Asn Ala Asn Arg Arg Arg Ser Arg Ala Val Leu Tyr His
                165                 170                 175 ctg tcc ggg cac ctg cag aag cag ccc aag ggc aag cac aag ctc aat   576
Leu Ser Gly His Leu Gln Lys Gln Pro Lys Gly Lys His Lys Leu Asn
            180                 185                 190 aag ggg gtg ttt ggg gag aaa cca aac ttg cct gag tac aaa gta gcc   624
Lys Gly Val Phe Gly Glu Lys Pro Asn Leu Pro Glu Tyr Lys Val Ala
        195                 200                 205 gcc atc cgg aag tcg ccc ttc atc ctg ttg cac tgt ggg gca ctg aga   672
Ala Ile Arg Lys Ser Pro Phe Ile Leu Leu His Cys Gly Ala Leu Arg
    210                 215                 220 gcc acc tgg gat ggc ttc atc ctg ctc gcc aca ctc tat gtg gct gtc   720
Ala Thr Trp Asp Gly Phe Ile Leu Leu Ala Thr Leu Tyr Val Ala Val
225                 230                 235                 240 act gtg ccc tac agc gtg tgt gtg agc aca gca cgg gag ccc agt gcc   768
Thr Val Pro Tyr Ser Val Cys Val Ser Thr Ala Arg Glu Pro Ser Ala
                245                 250                 255 gcc cgc ggc ccg ccc agc gtc tgt gac ctg gcc gtg gag gtc ctc ttc   816
Ala Arg Gly Pro Pro Ser Val Cys Asp Leu Ala Val Glu Val Leu Phe
            260                 265                 270 atc ctt gac att gtg ctg aat ttc cgt acc aca ttc gtg tcc aag tcg   864
Ile Leu Asp Ile Val Leu Asn Phe Arg Thr Thr Phe Val Ser Lys Ser
        275                 280                 285 ggc cag gtg gtg ttt gcc cca aag tcc att tgc ctc cac tac gtc acc   912
Gly Gln Val Val Phe Ala Pro Lys Ser Ile Cys Leu His Tyr Val Thr
    290                 295                 300 acc tgg ttc ctg ctg gat gtc atc gca gcg ctg ccc ttt gac ctg cta   960
Thr Trp Phe Leu Leu Asp Val Ile Ala Ala Leu Pro Phe Asp Leu Leu
305                 310                 315                 320
```

```
cat gcc ttc aag gtc aac gtg tac ttc ggg gcc cat ctg ctg aag acg      1008
His Ala Phe Lys Val Asn Val Tyr Phe Gly Ala His Leu Leu Lys Thr
                325                 330                 335 gtg cgc ctg ctg cgc ctg ctg cgc ctg ctt ccg cgg ctg gac cgg tac      1056
Val Arg Leu Leu Arg Leu Leu Arg Leu Leu Pro Arg Leu Asp Arg Tyr
            340                 345                 350 tcg cag tac agc gcc gtg gtg ctg aca ctg ctc atg gcc gtg ttc gcc      1104
Ser Gln Tyr Ser Ala Val Val Leu Thr Leu Leu Met Ala Val Phe Ala
        355                 360                 365 ctg ctc gcg cac tgg gtc gcc tgc gtc tgg ttt tac att ggc cag cgg      1152
Leu Leu Ala His Trp Val Ala Cys Val Trp Phe Tyr Ile Gly Gln Arg
    370                 375                 380 gag atc gag agc agc gaa tcc gag ctg cct gag att ggc tgg ctg cag      1200
Glu Ile Glu Ser Ser Glu Ser Glu Leu Pro Glu Ile Gly Trp Leu Gln
385                 390                 395                 400 gag ctg gcc cgc cga ctg gag act ccc tac tac ctg gtg ggc cgg agg      1248
Glu Leu Ala Arg Arg Leu Glu Thr Pro Tyr Tyr Leu Val Gly Arg Arg
                405                 410                 415 cca gct gga ggg aac agc tcc ggc cag agt gac aac tgc agc agc agc      1296
Pro Ala Gly Gly Asn Ser Ser Gly Gln Ser Asp Asn Cys Ser Ser Ser
            420                 425                 430 agc gag gcc aac ggg acg ggg ctg gag ctg ctg ggc ggc ccg tcg ctg      1344
Ser Glu Ala Asn Gly Thr Gly Leu Glu Leu Leu Gly Gly Pro Ser Leu
        435                 440                 445 cgc agc gcc tac atc acc tcc ctc tac ttc gca ctc agc agc ctc acc      1392
Arg Ser Ala Tyr Ile Thr Ser Leu Tyr Phe Ala Leu Ser Ser Leu Thr
    450                 455                 460 agc gtg ggc ttc ggc aac gtg tcc gcc aac acg gac acc gag aag atc      1440
Ser Val Gly Phe Gly Asn Val Ser Ala Asn Thr Asp Thr Glu Lys Ile
465                 470                 475                 480 ttc tcc atc tgc acc atg ctc atc ggc gcc ctg atg cac gcg gtg gtg      1488
Phe Ser Ile Cys Thr Met Leu Ile Gly Ala Leu Met His Ala Val Val
                485                 490                 495 ttt ggg aac gtg acg gcc atc atc cag cgc atg tac gcc cgc cgc ttt      1536
Phe Gly Asn Val Thr Ala Ile Ile Gln Arg Met Tyr Ala Arg Arg Phe
            500                 505                 510 ctg tac cac agc cgc acg cgc gac ctg cgc gac tac atc cgc atc cac      1584
Leu Tyr His Ser Arg Thr Arg Asp Leu Arg Asp Tyr Ile Arg Ile His
        515                 520                 525 cgt atc ccc aag ccc ctc aag cag cgc atg ctg gag tac ttc cag gcc      1632
Arg Ile Pro Lys Pro Leu Lys Gln Arg Met Leu Glu Tyr Phe Gln Ala
    530                 535                 540 acc tgg gcg gtg aac aat ggc atc gac acc acc gag ctg ctg cag agc      1680
Thr Trp Ala Val Asn Asn Gly Ile Asp Thr Thr Glu Leu Leu Gln Ser
545                 550                 555                 560 ctc cct gac gag ctg cgc gca gac atc gcc atg cac ctg cac aag gag      1728
Leu Pro Asp Glu Leu Arg Ala Asp Ile Ala Met His Leu His Lys Glu
                565                 570                 575 gtc ctg cag ctg cca ctg ttt gag gcg gcc agc cgc ggc tgc ctg cgg      1776
Val Leu Gln Leu Pro Leu Phe Glu Ala Ala Ser Arg Gly Cys Leu Arg
            580                 585                 590 gca ctg tct ctg gcc ctg cgg ccc gcc ttc tgc acg ccg ggc gag tac      1824
Ala Leu Ser Leu Ala Leu Arg Pro Ala Phe Cys Thr Pro Gly Glu Tyr
        595                 600                 605 ctc atc cac caa ggc gat gcc ctg cag gcc ctc tac ttt gtc tgc tct      1872
Leu Ile His Gln Gly Asp Ala Leu Gln Ala Leu Tyr Phe Val Cys Ser
    610                 615                 620 ggc tcc atg gag gtg ctc aag ggt ggc acc gtg ctc gcc atc cta ggg      1920
Gly Ser Met Glu Val Leu Lys Gly Gly Thr Val Leu Ala Ile Leu Gly
625                 630                 635                 640
```

-continued

| | |
|---|---|
| aag ggc gac ctg atc ggc tgt gag ctg ccc cgg cgg gag cag gtg gta<br>Lys Gly Asp Leu Ile Gly Cys Glu Leu Pro Arg Arg Glu Gln Val Val<br>645 650 655 | 1968 |
| aag gcc aat gcc gac gtg aag ggg ctg acg tac tgc gtc ctg cag tgt<br>Lys Ala Asn Ala Asp Val Lys Gly Leu Thr Tyr Cys Val Leu Gln Cys<br>660 665 670 | 2016 |
| ctg cag ctg gct ggc ctg cac gac agc ctt gcg ctg tac ccc gag ttt<br>Leu Gln Leu Ala Gly Leu His Asp Ser Leu Ala Leu Tyr Pro Glu Phe<br>675 680 685 | 2064 |
| gcc ccg cgc ttc agt cgt ggc ctc cga ggg gag ctc agc tac aac ctg<br>Ala Pro Arg Phe Ser Arg Gly Leu Arg Gly Glu Leu Ser Tyr Asn Leu<br>690 695 700 | 2112 |
| ggt gct ggg gga ggc tct gca gag gtg gac acc agc tcc ctg agc ggc<br>Gly Ala Gly Gly Gly Ser Ala Glu Val Asp Thr Ser Ser Leu Ser Gly<br>705 710 715 720 | 2160 |
| gac aat acc ctt atg tcc acg ctg gag gag aag gag aca gat ggg gag<br>Asp Asn Thr Leu Met Ser Thr Leu Glu Glu Lys Glu Thr Asp Gly Glu<br>725 730 735 | 2208 |
| cag ggc ccc acg gtc tcc cca gcc cca gct gat gag ccc tcc agc ccc<br>Gln Gly Pro Thr Val Ser Pro Ala Pro Ala Asp Glu Pro Ser Ser Pro<br>740 745 750 | 2256 |
| ctg ctg tcc cct ggc tgc acc tcc tca tcc tca gct gcc aag ctg cta<br>Leu Leu Ser Pro Gly Cys Thr Ser Ser Ser Ser Ala Ala Lys Leu Leu<br>755 760 765 | 2304 |
| tcc cca cgt cga aca gca ccc cgg cct cgt cta ggt ggc aga ggg agg<br>Ser Pro Arg Arg Thr Ala Pro Arg Pro Arg Leu Gly Gly Arg Gly Arg<br>770 775 780 | 2352 |
| cca ggc agg gca ggg gct ttg aag gct gag gct ggc ccc tct gct ccc<br>Pro Gly Arg Ala Gly Ala Leu Lys Ala Glu Ala Gly Pro Ser Ala Pro<br>785 790 795 800 | 2400 |
| cca cgg gcc cta gag ggg cta cgg ctg ccc ccc atg cca tgg aat gtg<br>Pro Arg Ala Leu Glu Gly Leu Arg Leu Pro Pro Met Pro Trp Asn Val<br>805 810 815 | 2448 |
| ccc cca gat ctg agc ccc agg gta gta gat ggc att gaa gac ggc tgt<br>Pro Pro Asp Leu Ser Pro Arg Val Val Asp Gly Ile Glu Asp Gly Cys<br>820 825 830 | 2496 |
| ggc tcg gac cag ccc aag ttc tct ttc cgc gtg ggc cag tct ggc ccg<br>Gly Ser Asp Gln Pro Lys Phe Ser Phe Arg Val Gly Gln Ser Gly Pro<br>835 840 845 | 2544 |
| gaa tgt agc agc agc ccc tcc cct gga cca gag agc ggc ctg ctc act<br>Glu Cys Ser Ser Ser Pro Ser Pro Gly Pro Glu Ser Gly Leu Leu Thr<br>850 855 860 | 2592 |
| gtt ccc cat ggg ccc agc gag gca agg aac aca gac aca ctg gac aag<br>Val Pro His Gly Pro Ser Glu Ala Arg Asn Thr Asp Thr Leu Asp Lys<br>865 870 875 880 | 2640 |
| ctt cgg cag gcg gtg aca gag ctg tca gag cag gtg ctg cag atg cgg<br>Leu Arg Gln Ala Val Thr Glu Leu Ser Glu Gln Val Leu Gln Met Arg<br>885 890 895 | 2688 |
| gaa gga ctg cag tca ctt cgc cag gct gtg cag ctt gtc ctg gcg ccc<br>Glu Gly Leu Gln Ser Leu Arg Gln Ala Val Gln Leu Val Leu Ala Pro<br>900 905 910 | 2736 |
| cac agg gag ggt ccg tgc cct cgg gca tcg gga gag ggg ccg tgc cca<br>His Arg Glu Gly Pro Cys Pro Arg Ala Ser Gly Glu Gly Pro Cys Pro<br>915 920 925 | 2784 |
| gcc agc acc tcc ggg ctt ctg cag cct ctg tgt gtg gac act ggg gca<br>Ala Ser Thr Ser Gly Leu Leu Gln Pro Leu Cys Val Asp Thr Gly Ala<br>930 935 940 | 2832 |
| tcc tcc tac tgc ctg cag ccc cca gct ggc tct gtc ttg agt ggg act<br>Ser Ser Tyr Cys Leu Gln Pro Pro Ala Gly Ser Val Leu Ser Gly Thr | 2880 |

-continued

```
                 945                 950                 955                 960
tgg ccc cac cct cgt ccg ggg cct cct ccc ctc atg gca ccc tgg ccc       2928
Trp Pro His Pro Arg Pro Gly Pro Pro Pro Leu Met Ala Pro Trp Pro
                965                 970                 975 tgg ggt ccc cca gcg tct cag agc tcc ccc tgg cct cga gcc aca gct       2976
Trp Gly Pro Pro Ala Ser Gln Ser Ser Pro Trp Pro Arg Ala Thr Ala
                980                 985                 990 ttc tgg acc tcc acc tca gac tca gag ccc cct gcc tca gga gac ctc       3024
Phe Trp Thr Ser Thr Ser Asp Ser Glu Pro Pro Ala Ser Gly Asp Leu
            995                 1000                1005 tgc tct gag ccc agc acc cct gcc tcc cct cct cct tct gag gaa           3069
Cys Ser Glu Pro Ser Thr Pro Ala Ser Pro Pro Pro Ser Glu Glu
    1010                1015                1020 ggg gct agg act ggg ccc gca gag cct gtg agc cag gct gag gct           3114
Gly Ala Arg Thr Gly Pro Ala Glu Pro Val Ser Gln Ala Glu Ala
    1025                1030                1035 acc agc act gga gag ccc cca cca ggg tca ggg ggc ctg gcc ttg           3159
Thr Ser Thr Gly Glu Pro Pro Pro Gly Ser Gly Gly Leu Ala Leu
    1040                1045                1050 ccc tgg gac ccc cac agc ctg gag atg gtg ctt att ggc tgc cat           3204
Pro Trp Asp Pro His Ser Leu Glu Met Val Leu Ile Gly Cys His
    1055                1060                1065 ggc tct ggc aca gtc cag tgg acc cag gaa gaa ggc aca ggg gtc           3249
Gly Ser Gly Thr Val Gln Trp Thr Gln Glu Glu Gly Thr Gly Val
    1070                1075                1080 tga                                                                   3252
```

<210> SEQ ID NO 2
<211> LENGTH: 1083
<212> TYPE: PRT
<213> ORGANISM: Homo sapiens

<400> SEQUENCE: 2

```
Met Pro Ala Met Arg Gly Leu Leu Ala Pro Gln Asn Thr Phe Leu Asp
1               5                   10                  15

Thr Ile Ala Thr Arg Phe Asp Gly Thr His Ser Asn Phe Val Leu Gly
                20                  25                  30

Asn Ala Gln Val Ala Gly Leu Phe Pro Val Val Tyr Cys Ser Asp Gly
            35                  40                  45

Phe Cys Asp Leu Thr Gly Phe Ser Arg Ala Glu Val Met Gln Arg Gly
        50                  55                  60

Cys Ala Cys Ser Phe Leu Tyr Gly Pro Asp Thr Ser Glu Leu Val Arg
65                  70                  75                  80

Gln Gln Ile Arg Lys Ala Leu Asp Glu His Lys Glu Phe Lys Ala Glu
                85                  90                  95

Leu Ile Leu Tyr Arg Lys Ser Gly Leu Pro Phe Trp Cys Leu Leu Asp
            100                 105                 110

Val Ile Pro Ile Lys Asn Glu Lys Gly Glu Val Ala Leu Phe Leu Val
        115                 120                 125

Ser His Lys Asp Ile Ser Glu Thr Lys Asn Arg Gly Gly Pro Asp Arg
    130                 135                 140

Trp Lys Glu Thr Gly Gly Gly Arg Arg Arg Tyr Gly Arg Ala Arg Ser
145                 150                 155                 160

Lys Gly Phe Asn Ala Asn Arg Arg Arg Ser Arg Ala Val Leu Tyr His
                165                 170                 175

Leu Ser Gly His Leu Gln Lys Gln Pro Lys Gly Lys His Lys Leu Asn
            180                 185                 190
```

-continued

```
Lys Gly Val Phe Gly Glu Lys Pro Asn Leu Pro Glu Tyr Lys Val Ala
        195                 200                 205
Ala Ile Arg Lys Ser Pro Phe Ile Leu Leu His Cys Gly Ala Leu Arg
210                 215                 220
Ala Thr Trp Asp Gly Phe Ile Leu Leu Ala Thr Leu Tyr Val Ala Val
225                 230                 235                 240
Thr Val Pro Tyr Ser Val Cys Val Ser Thr Ala Arg Glu Pro Ser Ala
                245                 250                 255
Ala Arg Gly Pro Pro Ser Val Cys Asp Leu Ala Val Glu Val Leu Phe
            260                 265                 270
Ile Leu Asp Ile Val Leu Asn Phe Arg Thr Thr Phe Val Ser Lys Ser
        275                 280                 285
Gly Gln Val Val Phe Ala Pro Lys Ser Ile Cys Leu His Tyr Val Thr
    290                 295                 300
Thr Trp Phe Leu Leu Asp Val Ile Ala Ala Leu Pro Phe Asp Leu Leu
305                 310                 315                 320
His Ala Phe Lys Val Asn Val Tyr Phe Gly Ala His Leu Leu Lys Thr
                325                 330                 335
Val Arg Leu Leu Arg Leu Leu Arg Leu Leu Pro Arg Leu Asp Arg Tyr
            340                 345                 350
Ser Gln Tyr Ser Ala Val Val Leu Thr Leu Leu Met Ala Val Phe Ala
        355                 360                 365
Leu Leu Ala His Trp Val Ala Cys Val Trp Phe Tyr Ile Gly Gln Arg
    370                 375                 380
Glu Ile Glu Ser Ser Glu Ser Glu Leu Pro Glu Ile Gly Trp Leu Gln
385                 390                 395                 400
Glu Leu Ala Arg Arg Leu Glu Thr Pro Tyr Tyr Leu Val Gly Arg Arg
                405                 410                 415
Pro Ala Gly Gly Asn Ser Ser Gly Gln Ser Asp Asn Cys Ser Ser Ser
            420                 425                 430
Ser Glu Ala Asn Gly Thr Gly Leu Glu Leu Leu Gly Gly Pro Ser Leu
        435                 440                 445
Arg Ser Ala Tyr Ile Thr Ser Leu Tyr Phe Ala Leu Ser Ser Leu Thr
    450                 455                 460
Ser Val Gly Phe Gly Asn Val Ser Ala Asn Thr Asp Thr Glu Lys Ile
465                 470                 475                 480
Phe Ser Ile Cys Thr Met Leu Ile Gly Ala Leu Met His Ala Val Val
                485                 490                 495
Phe Gly Asn Val Thr Ala Ile Ile Gln Arg Met Tyr Ala Arg Arg Phe
            500                 505                 510
Leu Tyr His Ser Arg Thr Arg Asp Leu Arg Asp Tyr Ile Arg Ile His
        515                 520                 525
Arg Ile Pro Lys Pro Leu Lys Gln Arg Met Leu Glu Tyr Phe Gln Ala
    530                 535                 540
Thr Trp Ala Val Asn Asn Gly Ile Asp Thr Thr Glu Leu Leu Gln Ser
545                 550                 555                 560
Leu Pro Asp Glu Leu Arg Ala Asp Ile Ala Met His Leu His Lys Glu
                565                 570                 575
Val Leu Gln Leu Pro Leu Phe Glu Ala Ala Ser Arg Gly Cys Leu Arg
            580                 585                 590
Ala Leu Ser Leu Ala Leu Arg Pro Ala Phe Cys Thr Pro Gly Glu Tyr
        595                 600                 605
```

-continued

```
Leu Ile His Gln Gly Asp Ala Leu Gln Ala Leu Tyr Phe Val Cys Ser
    610                 615                 620
Gly Ser Met Glu Val Leu Lys Gly Gly Thr Val Leu Ala Ile Leu Gly
625                 630                 635                 640
Lys Gly Asp Leu Ile Gly Cys Glu Leu Pro Arg Arg Glu Gln Val Val
                645                 650                 655
Lys Ala Asn Ala Asp Val Lys Gly Leu Thr Tyr Cys Val Leu Gln Cys
                660                 665                 670
Leu Gln Leu Ala Gly Leu His Asp Ser Leu Ala Leu Tyr Pro Glu Phe
            675                 680                 685
Ala Pro Arg Phe Ser Arg Gly Leu Arg Gly Glu Leu Ser Tyr Asn Leu
690                 695                 700
Gly Ala Gly Gly Ser Ala Glu Val Asp Thr Ser Ser Leu Ser Gly
705                 710                 715                 720
Asp Asn Thr Leu Met Ser Thr Leu Glu Glu Lys Glu Thr Asp Gly Glu
                725                 730                 735
Gln Gly Pro Thr Val Ser Pro Ala Pro Ala Asp Glu Pro Ser Ser Pro
            740                 745                 750
Leu Leu Ser Pro Gly Cys Thr Ser Ser Ser Ala Ala Lys Leu Leu
            755                 760                 765
Ser Pro Arg Arg Thr Ala Pro Arg Pro Arg Leu Gly Gly Arg Gly Arg
770                 775                 780
Pro Gly Arg Ala Gly Ala Leu Lys Ala Glu Ala Gly Pro Ser Ala Pro
785                 790                 795                 800
Pro Arg Ala Leu Glu Gly Leu Arg Leu Pro Pro Met Pro Trp Asn Val
                805                 810                 815
Pro Pro Asp Leu Ser Pro Arg Val Val Asp Gly Ile Glu Asp Gly Cys
            820                 825                 830
Gly Ser Asp Gln Pro Lys Phe Ser Phe Arg Val Gly Gln Ser Gly Pro
            835                 840                 845
Glu Cys Ser Ser Ser Pro Ser Pro Gly Pro Glu Ser Gly Leu Leu Thr
850                 855                 860
Val Pro His Gly Pro Ser Glu Ala Arg Asn Thr Asp Thr Leu Asp Lys
865                 870                 875                 880
Leu Arg Gln Ala Val Thr Glu Leu Ser Glu Gln Val Leu Gln Met Arg
                885                 890                 895
Glu Gly Leu Gln Ser Leu Arg Gln Ala Val Gln Leu Val Leu Ala Pro
            900                 905                 910
His Arg Glu Gly Pro Cys Pro Arg Ala Ser Gly Glu Gly Pro Cys Pro
        915                 920                 925
Ala Ser Thr Ser Gly Leu Leu Gln Pro Leu Cys Val Asp Thr Gly Ala
    930                 935                 940
Ser Ser Tyr Cys Leu Gln Pro Ala Gly Ser Val Leu Ser Gly Thr
945                 950                 955                 960
Trp Pro His Pro Arg Pro Gly Pro Pro Leu Met Ala Pro Trp Pro
                965                 970                 975
Trp Gly Pro Pro Ala Ser Gln Ser Ser Pro Trp Pro Arg Ala Thr Ala
            980                 985                 990
Phe Trp Thr Ser Thr Ser Asp Ser  Glu Pro Pro Ala Ser  Gly Asp Leu
        995                 1000                1005
Cys Ser  Glu Pro Ser Thr Pro  Ala Ser Pro Pro   Ser Glu Glu
    1010            1015                1020
Gly Ala  Arg Thr Gly Pro Ala  Glu Pro Val Ser Gln  Ala Glu Ala
```

```
                1025                1030                1035
Thr Ser Thr Gly Glu Pro Pro Gly Ser Gly Gly Leu Ala Leu
        1040                1045                1050

Pro Trp Asp Pro His Ser Leu Glu Met Val Leu Ile Gly Cys His
        1055                1060                1065

Gly Ser Gly Thr Val Gln Trp Thr Gln Glu Gly Thr Gly Val
        1070                1075                1080
```

<210> SEQ ID NO 3
<211> LENGTH: 40
<212> TYPE: DNA
<213> ORGANISM: Artificial Sequence
<220> FEATURE:
<223> OTHER INFORMATION: primer sequence

<400> SEQUENCE: 3
attcgacgtc gatctttttt ccgtaaactc aataccaggc                    40

<210> SEQ ID NO 4
<211> LENGTH: 20
<212> TYPE: DNA
<213> ORGANISM: Mus sp.

<400> SEQUENCE: 4
gcgggcatca aggagtcaag                                          20

<210> SEQ ID NO 5
<211> LENGTH: 20
<212> TYPE: DNA
<213> ORGANISM: Mus sp.

<400> SEQUENCE: 5
ctcctgtccc tcccgttgac                                          20

<210> SEQ ID NO 6
<211> LENGTH: 29
<212> TYPE: DNA
<213> ORGANISM: Artificial Sequence
<220> FEATURE:
<223> OTHER INFORMATION: primer sequence

<400> SEQUENCE: 6
acgcgtcgac ctgcccgtgc tcctgagtg                                29

<210> SEQ ID NO 7
<211> LENGTH: 29
<212> TYPE: DNA
<213> ORGANISM: Artificial Sequence
<220> FEATURE:
<223> OTHER INFORMATION: primer sequence

<400> SEQUENCE: 7
acgcgtcgac ccaagctctg aaaaaccag                                29

<210> SEQ ID NO 8
<211> LENGTH: 36
<212> TYPE: DNA
<213> ORGANISM: Artificial Sequence
<220> FEATURE:
<223> OTHER INFORMATION: primer sequence

<400> SEQUENCE: 8
ggggtaccgc ggccgcgggg atccagacat gataag                        36

```
<210> SEQ ID NO 9
<211> LENGTH: 20
<212> TYPE: DNA
<213> ORGANISM: Homo sapiens

<400> SEQUENCE: 9
cgaggcaagg aacacagaca                                                    20

<210> SEQ ID NO 10
<211> LENGTH: 18
<212> TYPE: DNA
<213> ORGANISM: Homo sapiens

<400> SEQUENCE: 10
ggggctgcag gcagtagg                                                      18

<210> SEQ ID NO 11
<211> LENGTH: 20
<212> TYPE: DNA
<213> ORGANISM: Homo sapiens

<400> SEQUENCE: 11
agtcacttcg ccaggctgtg                                                    20

<210> SEQ ID NO 12
<211> LENGTH: 18
<212> TYPE: DNA
<213> ORGANISM: Homo sapiens

<400> SEQUENCE: 12
ggggctgcag gcagtagg                                                      18
```